US009273283B2

(12) United States Patent
Sentman

(10) Patent No.: US 9,273,283 B2
(45) Date of Patent: *Mar. 1, 2016

(54) METHOD OF PRODUCING T CELL RECEPTOR-DEFICIENT T CELLS EXPRESSING A CHIMERIC RECEPTOR

(75) Inventor: Charles L. Sentman, West Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/459,664

(22) Filed: Apr. 30, 2012

(65) Prior Publication Data

US 2012/0302466 A1 Nov. 29, 2012

Related U.S. Application Data

(63) Continuation-in-part of application No. 13/502,978, filed as application No. PCT/US2010/054846 on Oct. 29, 2010.

(60) Provisional application No. 61/255,980, filed on Oct. 29, 2009.

(51) Int. Cl.
*C12N 15/00* (2006.01)
*C12N 5/0783* (2010.01)
*A61K 39/00* (2006.01)

(52) U.S. Cl.
CPC ....... *C12N 5/0636* (2013.01); *A61K 2039/5156* (2013.01); *C12N 2501/515* (2013.01)

(58) Field of Classification Search
None
See application file for complete search history.

(56) References Cited

U.S. PATENT DOCUMENTS

| | | | |
|---|---|---|---|
| 5,359,046 A | 10/1994 | Capon et al. |
| 5,415,874 A | 5/1995 | Bender et al. |
| 5,552,300 A | 9/1996 | Makrides et al. |
| 5,667,967 A | 9/1997 | Steinman et al. |
| 5,686,281 A | 11/1997 | Roberts |
| 5,712,149 A | 1/1998 | Roberts |
| 5,830,755 A | 11/1998 | Nishimura et al. |
| 5,851,828 A | 12/1998 | Seed et al. |
| 6,103,521 A | 8/2000 | Capon et al. |
| 6,284,240 B1 | 9/2001 | Seed et al. |
| 6,319,494 B1 | 11/2001 | Capon et al. |
| 6,407,221 B1 | 6/2002 | Capon et al. |
| 6,410,319 B1 | 6/2002 | Raubitschek et al. |
| 6,464,978 B1 | 10/2002 | Brostoff et al. |
| 6,753,162 B1 | 6/2004 | Seed et al. |
| 6,770,749 B2 | 8/2004 | Ellenhorn et al. |
| 6,953,576 B2 | 10/2005 | Zhang et al. |
| 6,984,382 B1 | 1/2006 | Groner et al. |
| 7,049,136 B2 | 5/2006 | Seed et al. |
| 7,052,906 B1 | 5/2006 | Lawson et al. |
| 7,070,995 B2 | 7/2006 | Jensen |
| 7,094,599 B2 | 8/2006 | Seed et al. |
| 7,446,179 B2 | 11/2008 | Jensen et al. |
| 7,446,190 B2 | 11/2008 | Sadelain et al. |
| 7,456,263 B2 | 11/2008 | Sherman et al. |
| 7,514,537 B2 | 4/2009 | Jensen |
| 7,569,357 B2 | 8/2009 | Kranz et al. |
| 7,608,410 B2 | 10/2009 | Dunn et al. |
| 7,618,817 B2 | 11/2009 | Campbell |
| 7,655,461 B2 | 2/2010 | Finn et al. |
| 7,763,243 B2 | 7/2010 | Lum et al. |
| 7,820,174 B2 | 10/2010 | Wang et al. |
| 7,994,298 B2 | 8/2011 | Zhang et al. |
| 8,026,097 B2 | 9/2011 | Campana et al. |
| 8,252,914 B2 | 8/2012 | Zhang et al. |
| 8,283,446 B2 | 10/2012 | Jakobsen et al. |
| 8,399,645 B2 | 3/2013 | Campana et al. |
| 8,465,743 B2 | 6/2013 | Rosenberg et al. |
| 8,519,100 B2 | 8/2013 | Jakobsen et al. |
| 8,945,868 B2 * | 2/2015 | Collingwood et al. ...... 435/69.1 |
| 8,956,828 B2 | 2/2015 | Bonini et al. |
| 2001/0007152 A1 | 7/2001 | Sherman et al. |
| 2002/0045241 A1 | 4/2002 | Schendel |
| 2002/0137697 A1 | 9/2002 | Eshhar et al. |
| 2003/0060444 A1 | 3/2003 | Finney et al. |

(Continued)

FOREIGN PATENT DOCUMENTS

| | | |
|---|---|---|
| DE | 4408999 | 9/1995 |
| DE | 19540515 | 6/1997 |

(Continued)

OTHER PUBLICATIONS

Trickett et al., Journal of Immunological Methods 275 (2003) 251-255.*
Cooper, Methods 37 (2005) 331-340.*
Stoss et al., Brain Research Protocols 4_1999. 383-394.*
Wilson et al., Biochimie 91 (2009) 1342-1345.*
Barber et al. (Experimental Hematology 2008;36:1318-1328).*
Schumacher (Nat Rev Immunol. Jul. 2002;2(7):512-9).*
Eagle et al. (Curr Immunol Rev. Feb. 2009 ; 5(1): 22-34).*
Basu et al. (Clinical Immunology (2008) 129, 325-332).*
Call et al., Molecular Immunology 40 (2004) 1295-1305.*
Polio et al. (Proc Natl Acad Sci U S A. Jul. 17, 2001;98(15):8744-9).*
Gascoigne (J. Biol. Chem. 1990, 265:9296-9301).*
Surh et al. (Immunological Reviews 2006 vol. 211: 154-163).*
Maloy et al., Nature Immunology vol. 6 No. 11 Nov. 2005, pp. 1071-1072.*

(Continued)

*Primary Examiner* — Zachary Skelding
(74) *Attorney, Agent, or Firm* — Robin L. Teskin; LeClairRyan, A Professional Corporation

(57) ABSTRACT

The invention is directed to modified T cells, methods of making and using isolated, modified T cells, and methods of using these isolated, modified T cells to address diseases and disorders. In one embodiment, this invention broadly relates to TCR-deficient T cells, isolated populations thereof, and compositions comprising the same. In another embodiment of the invention, these TCR-deficient T cells are designed to express a functional non-TCR receptor. The invention also pertains to methods of making said TCR-deficient T cells, and methods of reducing or ameliorating, or preventing or treating, diseases and disorders using said TCR-deficient T cells, populations thereof, or compositions comprising the same.

30 Claims, 3 Drawing Sheets

(56) References Cited

U.S. PATENT DOCUMENTS

| | | |
|---|---|---|
| 2003/0077249 A1 | 4/2003 | Bebbington et al. |
| 2003/0082719 A1 | 5/2003 | Schumacher et al. |
| 2003/0093818 A1 | 5/2003 | Belmont et al. |
| 2003/0219463 A1 | 11/2003 | Falkenburg et al. |
| 2004/0038886 A1 | 2/2004 | Finney et al. |
| 2004/0115198 A1 | 6/2004 | Spies et al. |
| 2004/0259196 A1 | 12/2004 | Zipori et al. |
| 2005/0048055 A1 | 3/2005 | Newell et al. |
| 2005/0129671 A1 | 6/2005 | Cooper et al. |
| 2005/0238626 A1 | 10/2005 | Yang et al. |
| 2006/0093605 A1 | 5/2006 | Campana et al. |
| 2006/0166314 A1 | 7/2006 | Voss et al. |
| 2006/0247420 A1 | 11/2006 | Coukos et al. |
| 2006/0263334 A1 | 11/2006 | Finn et al. |
| 2006/0269529 A1 | 11/2006 | Niederman et al. |
| 2007/0066802 A1 | 3/2007 | Geiger |
| 2007/0077241 A1 | 4/2007 | Spies et al. |
| 2007/0116690 A1 | 5/2007 | Yang et al. |
| 2008/0199424 A1 | 8/2008 | Yang Lili et al. |
| 2008/0292549 A1 | 11/2008 | Jakobsen et al. |
| 2008/0292602 A1 | 11/2008 | Jakobsen et al. |
| 2009/0053184 A1 | 2/2009 | Morgan et al. |
| 2009/0202501 A1 | 8/2009 | Zhang et al. |
| 2009/0226404 A1 | 9/2009 | Schuler et al. |
| 2009/0304657 A1 | 12/2009 | Morgan et al. |
| 2009/0324566 A1 | 12/2009 | Shiku et al. |
| 2010/0009863 A1 | 1/2010 | Himmler et al. |
| 2010/0015113 A1 | 1/2010 | Restifo et al. |
| 2010/0029749 A1 | 2/2010 | Zhang et al. |
| 2010/0055117 A1 | 3/2010 | Krackhardt et al. |
| 2010/0104556 A1 | 4/2010 | Blankenstein et al. |
| 2010/0105136 A1 | 4/2010 | Carter et al. |
| 2010/0135974 A1 | 6/2010 | Eshhar et al. |
| 2010/0143315 A1 | 6/2010 | Voss et al. |
| 2010/0178276 A1 | 7/2010 | Sadelain et al. |
| 2010/0189728 A1 | 7/2010 | Schendel et al. |
| 2010/0273213 A1 | 10/2010 | Mineno et al. |
| 2011/0158957 A1 | 6/2011 | Bonini et al. |
| 2011/0213288 A1* | 9/2011 | Choi et al. .................. 604/6.08 |
| 2012/0252742 A1 | 10/2012 | Kranz et al. |
| 2012/0294857 A1 | 11/2012 | Sentman et al. |
| 2012/0302466 A1 | 11/2012 | Sentman et al. |
| 2012/0321667 A1 | 12/2012 | Sentman |
| 2013/0011375 A1 | 1/2013 | Chen |
| 2013/0323214 A1 | 12/2013 | Gottschalk et al. |
| 2014/0004132 A1 | 1/2014 | Brenner et al. |
| 2014/0328812 A1 | 11/2014 | Campana et al. |
| 2014/0341869 A1 | 11/2014 | Campana et al. |
| 2014/0349402 A1* | 11/2014 | Cooper et al. ................. 435/455 |

FOREIGN PATENT DOCUMENTS

| | | |
|---|---|---|
| DE | 10259713 | 8/2004 |
| EP | 0340793 | 8/1995 |
| EP | 0 842 194 | 5/1998 |
| EP | 0499555 | 5/2000 |
| EP | 0574512 | 5/2003 |
| EP | 1226244 | 7/2004 |
| EP | 0871495 | 6/2005 |
| EP | 1075517 | 7/2006 |
| EP | 1932537 | 6/2008 |
| EP | 1765860 | 10/2008 |
| EP | 2186825 | 5/2010 |
| EP | 1791865 | 7/2010 |
| JP | H05176760 | 7/1993 |
| WO | 9118019 | 11/1991 |
| WO | 9215322 | 9/1992 |
| WO | 9424282 | 10/1994 |
| WO | 9615238 | 5/1996 |
| WO | 96/23814 | 8/1996 |
| WO | 9613584 | 9/1996 |
| WO | 9818809 | 7/1998 |
| WO | 9841613 | 9/1998 |
| WO | 0031239 | 2/2000 |
| WO | 0014257 | 3/2000 |
| WO | 1092291 | 6/2001 |
| WO | 2004056845 | 8/2004 |
| WO | WO 2006036445 A2 * | 4/2006 |
| WO | 2006103429 | 5/2006 |
| WO | 2006060878 | 6/2006 |
| WO | 2008153029 A1 | 12/2008 |
| WO | 2009059804 | 5/2009 |
| WO | 2009091826 | 7/2009 |
| WO | 2010012829 | 4/2010 |
| WO | 2010025177 | 4/2010 |
| WO | 2010058023 | 5/2010 |
| WO | 2010088160 | 5/2010 |
| WO | 2010037395 | 8/2010 |
| WO | 2010107400 | 9/2010 |
| WO | 2011059836 A3 | 9/2011 |
| WO | 2012050374 | 4/2012 |
| WO | 2013166051 A1 | 11/2013 |

OTHER PUBLICATIONS

Schneider et al. (JEM, vol. 204, No. 4, Apr. 16, 2007, 735-745).*
Kowolik et al., Cancer Res 2006; 66(22): 10995-1004.*
Yang et al., International Immunology, vol. 19, No. 9, pp. 1083-1093 (2007).*
Sadelain et al., Current Opinion in Immunology 2009, 21:215-223.*
Alegre, M. et al., "Effect of a Single Amino Acid Mutation on the Activating and Immunosuppressive Properties of a "Humanized" OKT3 Monoclonal Antibody", The Journal of Immunology, 1992, 148(11): 3461-3468.
Bridgeman, J.S. et al., "The Optimal Antigen Response of Chimeric Antigen Receptors Harboring the CD3ζ Transmembrane Domain Is Dependent upon Incorporation of the Receptor into the Endogenous TCR/CD3 Complex", The Journal of Immunology, 2010, 184: 6938-6949.
Cooper, L. et al., "Manufacturing of gene-modified cytotoxic T lymphocytes for autologous cellular therapy for lymphoma", Cytotherapy, 2006, 8(2): 105-117.
Cooper, L. et al., "Enhanced antilymphoma efficacy of CD19-redirected influenza MP1-specific CTLs by cotransfer of T cells modified to present influenza MP1", Blood, 2005, 105(4): 1622-1631.
Ehlers, S. et al., "αβ T Cell Receptor-positive Cells and Interferon-γ, but not Inducible Nitric Oxide Synthase, Are Critical for Ganuloma Necrosis in a Mouse Model of Mycobacteria-induced Pulmonary Immunopathology", Journal of Experimental Medicine, 2001, 194(12): 1847-1859.
Llano, M. et al., "Rapid, Controlled and Intensive Lentiviral Vector-Based RNAi", HIV Protocols, Methods in Molecular Biology, 2009, 485: 257-270.
Madrenas, J. et al., "Thymus-Independent Expression of a Truncated T Cell Receptor-α mRNA in Murine Kidney", The Journal of Immunology, 1992, 148(2): 612-619.
Merriam-Webster dictionary definition for "isolated", downloaded Oct. 14, 2014, pp. 1-2.
Pardoll, D., "Tumor reactive T cells get a boost", Nature Biotechnology, 2002, 20(12): 1207-8.
Roberts, S. et al., "T-cell αβ+ and γδ+ deficient mice display abnormal but distinct phenotypes toward a natural, widespread infection of the intestinal epithelium", Proc. Natl. Acad. Sci. USA, 1996, 93: 11774-11779.
Rubin, D. et al., "Altered Enteroendocrine Cell Expression in T Cell Receptor Alpha Chain Knock-Out Mice", Microscopy Research and Technique, 2000, 51: 112-120.
Scherr, M. et al., "Knock-Down of Gene Expression in Hematopoietic Cells", Methods in Molecular Biology, 2009, 506: 207-209.
Schwab, R. et al., "Requirements for T Cell Activation by OKT3 Monoclonal Antibody: Role of Modulation of T3 Molecules and Interleukin 1", The Journal of Immunology, 1985, 135(3): 1714-1718.
Stanley, P., lab wiki, "Transfection of Cells with DNA", Aug. 13, 2009, pp. 1-4.
Szczepanik, M. et al., "γδ T Cells from Tolerized αβ T Cell Receptor (TCR)-deficient Mice Inhibit Contact Sensitivity-Effector T Cells In

(56) References Cited

OTHER PUBLICATIONS

Vivo, and Their Interferon-γ Production In Vitro", Journal of Experimental Medicine, 1996, 184: 2129-2139.
Wormley, F. et al., "Resistance of T-Cell Receptor δ-Chain-Deficient Mice to Experimental Candida albicans Vaginitis", Infection and Immunity, 2001, 69(11): 7162-7164.
Alajez NM 'MHC-Unrestricted MUC1-Specific T Cell Receptor for Cancer Immunotherapy/Gene Therapy' (2003) MHC-Unrestricted MUC1-Specific T Cell Receptor for Cancer Immunotherapy/Gene Therapy.Doctoral Dissertation, University of Pittsburgh.
Alajez NM, et al. 'Therapeutic potential of a tumor-specific, MHC-unrestricted T-cell receptor expressed on effector cells of theinnate and the adaptive immune system through bone marrow transduction and immune reconstitution.' Blood. Jun. 15, 2005; 105(12):4583-9. Epub Mar. 3, 2005.
Alli R, et al. 'Retrogenic Modeling of Experimental Allergic Encephalomyelitis Associates T Cell Frequency but Not TCR Functional Affinity with Pathogenicity' J lmmunol. Jul. 1, 2008; 181(1):136-45.
Almåsbak H, et al. 'Non-MHC-dependent redirected T cells against tumor cells.' Methods Mol Biol. 2010;629:453-93. doi: 10.1007/978-1-60761-657-3_28.
Beecham EJ, et al. 'Dynamics of tumor cell killing by human T lymphocytes armed with an anti-carcinoembryonic antigen chimeric immunoglobulin T-cell receptor.' J Immunother. May-Jun. 2000; 23(3):332-43.
Bell LM, et al. 'Cytoplasmic tail deletion of T cell receptor (TCR) beta-chain results in its surface expression as glycosylphosphatidylinositol-anchored polypeptide on mature T cells in the absence of TCR-alpha.' J Biol Chem. Sep. 9, 1994; 269(36):22758-63.
Berry LJ, et al. 'Adoptive immunotherapy for cancer: the next generation of gene-engineered immune cells.' Tissue Antigens. Oct. 2009; 74(4):277-89. doi: 10.1111/j.1399-0039.2009.01336.
Bialer G, et al. 'Selected murine residues endow human TCR with enhanced tumor recognition' J Immunol. Jun. 1, 2010; 184(11):6232-41. doi: 10.4049/jimmunol.0902047. Epub Apr. 28, 2010.
Billadeau DD, et al. 'NKG2D-DAP10 triggers human NK cell-mediated killing via a Syk-independent regulatory pathway.' Nat Immunol. Jun. 2003; 4(6):557-64. Epub May 11, 2003.
Chmielewski M, et al. 'CD28 cosignalling does not affect the activation threshold in a chimeric antigen receptor-redirected T-cell attack.' Gene Ther. Jan. 2011; 18(1):62-72. doi: 10.1038/gt.2010.127. Epub Oct. 14, 2010.
Cohen CJ, et al. 'Enhanced Antitumor Activity of Murine-Human Hybrid T-Cell Receptor (TCR) in Human Lymphocytes Is Associated with Improved Pairing and TCR/CD3 Stability' Cancer Res. Sep. 1, 2006; 66(17):8878-86.
Dail P, et al. 'In vivo cervical cancer growth inhibition by genetically engineered cytotoxic T cell' Cancer Immunol Immunother. Jan. 2005; 54(1):51-60.
Danielian S, et al. 'Both T cell receptor (TcR)-CD3 complex and CD2 increase the tyrosine kinase activity of p56lck. CD2 can mediate TcR-CD3-independent and CD45-dependent activation of p56lck.' Eur J Immunol. Nov. 1992; 22(11):2915-21.
Donnadieu et al., 'Reconstitution of CD3 zeta coupling to calcium mobilization via genetic complementation.' J Biol. Chem. 269:32828-34 (1994).
Dennehy KM, et al. 'Mitogenic CD28 Signals Require the Exchange Factor Vav1 to Enhance TCR Signaling at the SLP-76-Vav-Itk Signalosome' J Immunol. Feb. 1, 2007; 178(3):1363-71.
D'Oro U, et al. 'Regulation of constitutive TCR internalization by the zeta-chain.' J Immunol. Dec. 1, 2002; 169(11):6269-78.
Duplay P, et al. 'An activated epidermal growth factor receptor/Lck chimera restores early T cell receptor-mediated calcium response in a CD45-deficient T cell line.' J Biol Chem. Jul. 26, 1996; 271(30):17896-902.
Eshhar Z, et al. 'Specific activation and targeting of cytotoxic lymphocytes through chimeric single chains consisting of antibody-binding domains and the gamma or zeta subunits of the immunoglobulin and T-cell receptors.' Proc Nat! Acad Sci U S A. Jan. 15, 1993; 90(2):720-4.
Favier B, et al. 'TCR dynamics on the surface of living T cells' Int Immunol. Dec. 2001; 13(12):1525-32.
Finney HM, et al. 'Chimeric receptors providing both primary and costimulatory signaling in T cells from a single gene product.' J Immunol. Sep. 15, 1998; 161(6):2791-7.
Frankel Tl, et al. 'Both CD4 and CD8 T Cells Mediate Equally Effective in Vivo Tumor Treatment When Engineered with a Highly Avid TCR Targeting Tyrosinase' J Immunol. Jun. 1, 2010; 184(11):5988-98. doi:10.4049/jimmuno1.1000189. Epub Apr 28, 2010.
Fujihashi K, et al. 'gamma/delta T cell-deficient mice have impaired mucosal immunoglobulin a response' J Exp Med. Apr. 1, 1996; 183(4):1929-35.
Garrity D, et al. 'The activating NKG2D receptor assembles in the membrane with two signaling dimers into a hexameric structure.' Proc Natl Acad Sci U S A. May 24, 2005; 102(21):7641-6. Epub May 13, 2005.
Geiger TL, et al. 'The TCR zeta-chain immunoreceptor tyrosine-based activation motifs are sufficient for the activation and differentiation of primary T lymphocytes.' J Immunol. May 15, 1999; 162(10):5931-9.
Geiger TL, et al. 'Integrated src kinase and costimulatory activity enhances signal transduction through single-chain chimeric receptors in T lymphocytes' Blood. Oct. 15, 2001; 98(8):2364-71.
Gouaillard C, et al. 'Evolution of T cell receptor (TCR) αβheterodimer assembly with the CD3 complex' Eur J Immunol. Dec. 2001; 31(12):3798-805.
Hawkins RE, et al. 'Development of adoptive cell therapy for cancer: a clinical perspective.' Hum Gene Ther. Jun. 2010; 21(6):665-72. doi: 10.1089/hum.2010.086.
Haynes NM, et al. 'Redirecting Mouse CTL Against Colon Carcinoma: Superior Signaling Efficacy of Single-Chain Variable Domain Chimeras Containing TCR-ζ vs FcεRI-γ' J Immunol. Jan. 1, 2001; 166(1):182-7.
Horng T, et al. 'NKG2D signaling is coupled to the interleukin 15 receptor signaling pathway.' Nat Immunol. Dec. 2007; 8(12):1345-52. Epub Oct. 21, 2007.
lmai C, et al. 'Chimeric receptors with 4-1BB signaling capacity provoke potent cytotoxicity against acute lymphoblastic leukemia.' Leukemia. Apr. 2004; 18(4):676-84.
Ides C, et al. 'CD45 ectodomain controls interaction with GEMs and Lck activity for optimal TCR signaling.' Nat Immunol. Feb. 2003; 4(2):189-97. Epub Dec. 23, 2002.
Itohara S, et al. 'T cell receptor delta gene mutant mice: independent generation of alpha beta T cells and programmed rearrangements of gamma delta TCR genes.' Cell. Feb. 12, 1993; 72(3):337-48.
Joyce DE, et al. 'Functional interactions between the thrombin receptor and the T-cell antigen receptor in human T-cell lines' Blood. Sep. 1, 1997; 90(5):1893-901.
Kieback E, et al. 'Enhanced T cell receptor gene therapy for cancer.' Expert Opin Biol Ther. May 2010; 10(5):749-62. doi: 10.1517/14712591003689998.
Kieback E, et al. 'A safeguard eliminates T cell receptor gene-modified autoreactive T cells after adoptive transfer' Proc Natl Acad Sci U S A. Jan. 15, 2008; 105(2):623-8. doi: 10.1073/pnas.0710198105. Epub Jan. 8, 2008.
Kreiβ et al., 'Contrasting contributions of complementarity-determining region 2 and hypervariable region 4 of rat BV8S2+ (Vbeta8.2) TCR to the recognition of myelin basic protein and different types of bacterial superantigens.' Int Immunol. 16(5):655-663 (2004).
Koya RC, et al. 'Kinetic phases of distribution and tumor targeting by T cell receptor engineered lymphocytes inducing robust antitumor responses.' Proc Natl Acad Sci U S A. Aug. 10, 2010; 107(32):14286-91. doi: 10.1073/pnas.1008300107. Epub Jul. 12, 2010.
Leisegang M, et al. 'T-Cell Receptor Gene—Modified T Cells with Shared Renal Cell Carcinoma Specificity for Adoptive T-Cell Therapy' Clin Cancer Res. Apr. 15, 2010; 16(8):2333-43. doi: 10.1158/1078-0432.CCR-09-2897. Epub Apr. 6, 2010.

(56) References Cited

OTHER PUBLICATIONS

Liang X, et al. 'A Single TCRα-Chain with Dominant Peptide Recognition in the Allorestricted HER2/neu-Specific T Cell Repertoire' J Immunol. Feb. 1, 2010; 184(3):1617-29. doi: 10.4049/jimmunol.0902155. Epub Dec. 30, 2009.

Lin WY, et al. 'Developmental dissociation of T cells from B, NK, and myeloid cells revealed by MHC class II-specific chimeric immune receptors bearing TCR-zeta or FcR-gamma chain signaling domains.' Blood. Oct. 15, 2002; 100(8):3045-8.

Losch FO, et al. 'Activation of T cells via tumor antigen specific chimeric receptors: the role of the intracellular signaling domain.' Int J Cancer. Jan. 20, 2003; 103(3):399-407.

Maher J, et al. 'Human T-lymphocyte cytotoxicity and proliferation directed by a single chimeric TCRzeta /CD28 receptor.' Nat Biotechnol. Jan. 2002; 20(1):70-5.

Mallevaey T, et al. 'T Cell Receptor CDR2b and CDR3b Loops Collaborate Functionally to Shape the iNKT Cell Repertoire' Immunity. Jul. 17, 2009; 31(1):60-71. doi: 10.1016/j.immuni, May 10, 2009.

Marie-Cardine A, et al. 'SHP2-interacting Transmembrane Adaptor Protein (SIT), A Novel Disulfide-linked Dimer Regulating Human T Cell Activation' J Exp Med. Apr. 19, 1999; 189(8):1181-94.

McFarland HI, et al. 'Signaling through MHC in transgenic mice generates a population of memory phenotype cytolytic cells that lack TCR.' Blood. Jun. 1, 2003; 101(11):4520-8. Epub Feb. 13, 2003.

Mekala DJ, et al. 'IL-10-dependent suppression of experimental allergic encephalomyelitis by Th2-differentiated, anti-TCRredirected T lymphocytes.' J Immunol. Mar. 15, 2005; 174(6):3789-97.

Meresse B, et al. 'Coordinated induction by IL15 of a TCR-independent NKG2D signaling pathway converts CTL into lymphokine-activated killer cells in celiac disease.' Immunity. Sep. 2004; 21(3):357-66.

Milone MC, et al. 'Chimeric receptors containing CD137 signal transduction domains mediate enhanced survival of T cells and increased antileukemic efficacy in vivo.' Mol Ther. Aug. 2009; 17(8):1453-64. doi: 10.1038/mt.2009.83. Epub Apr. 21, 2009.

Mizoguchi A, et al. 'Role of appendix in the development of inflammatory bowel disease in TCR-alpha mutant mice.' J Exp Med. Aug. 1, 1996; 184(2):707-15.

Moeller M, et al. 'A functional role for CD28 costimulation in tumor recognition by single-chain receptor-modified T cells.' Cancer Gene Ther. May 2004; 11(5):371-9.

Moisini I, et al. 'Redirecting Therapeutic T Cells against Myelin-Specific T Lymphocytes Using a Humanized Myelin Basic Protein-HLA-DR2-ζ Chimeric Receptor' J Immunol. Mar. 1, 2008; 180(5):3601-11.

Mombaerts P, et al. 'Mutations in T-cell antigen receptor genes alpha and beta block thymocyte development at different stages.' Nature. Nov. 19, 1992; 360(6401):225-31.

Motmans K, et al. 'Enhancing the tumor-specifity of human T cells by the expression of chimericimmunoglobulin/T cell receptor genes.' Immunotechnology, Nov. 1996;2(4): 303-304(2).

Nguyen P, et al. 'Antigen-specific targeting of CD8+ T cells with receptor-modified T lymphocytes.' Gene Ther. Apr. 2003; 10(7):594-604.

Nguyen P, et al. 'Discrete TCR repertoires and CDR3 features distinguish effector and Foxp3+ regulatory T lymphocytes in myelin oligodendrocyte glycoprotein-induced experimental allergic encephalomyelitis.' J Immunol. Oct. 1, 2010; 185(7):3895-904. doi: 10.4049/jimmunol.1001550. Epub Sep. 1, 2010.

Okamoto et al., 'Improved expression and reactivity of transduced tumor-specific TCRs in human lymphocytes by specific silencing of endogenous TCR.' Cancer Res 69:9003-11 (2009).

Nguyen P, et al. 'Identification of a murine CD28 dileucine motif that suppresses single-chain chimeric T-cell receptor expression and function.' Blood. Dec. 15, 2003; 102(13):4320-5. Epub Aug. 28, 2003.

Qian D, et al. 'Dominant-negative zeta-associated protein 70 inhibits T cell antigen receptor signaling.' J Exp Med. Feb. 1, 1996; 183(2):611-20.

Rivera A, et al. 'Host stem cells can selectively reconstitute missing lymphoid lineages in irradiation bone marrow chimeras.' Blood. Jun. 1, 2003; 101(11):4347-54. Epub Feb. 13, 2003.

Rossig C, et al. 'Targeting of G(D2)-positive tumor cells by human T lymphocytes engineered to express chimeric T-cell receptor genes' Int J Cancer. Oct. 15, 2001; 94(2):228-36.

Sadelain M. 'T-cell engineering for cancer immunotherapy.' Cancer J. Nov.-Dec. 2009; 15(6):451-5. doi: 10.1097/PPO.0b013e3181c51f37.

Schirrmann T, et al. 'Human natural killer cell line modified with a chimeric immunoglobulin T-cell receptor gene leads to tumor growth inhibition in vivo' Cancer Gene Ther. Apr. 2002; 9(4):390-8.

Schmitt TM, et al. 'T cell receptor gene therapy for cancer.' Hum Gene Ther. Nov. 2009; 20(11):1240-8. doi: 10.1089/hum.2009.146.

Sommermeyer D, et al. 'Designer T cells by T cell receptor replacement' Eur J Immunol. Nov. 2006; 36(11):3052-9.

Spaapen R 'Rebuilding human leukocyte antigen class II-restricted.' Novel strategies for identification and therapeutic application of minor histocompatibility antigens 13 (2009): 79.

Spaapen R, et al. 'Rebuilding Human Leukocyte Antigen Class II—Restricted Minor Histocompatibility Antigen Specificity in Recall Antigen-Specific T Cells by Adoptive T Cell Receptor Transfer: Implications for Adoptive Immunotherapy' Clin Cancer Res. Jul. 1, 2007; 13(13):4009-15.

Sturmhofel K, et al. 'Antigen-independent, integrin-mediated T cell activation.' J Immunol. Mar. 1, 1995; 154(5):2104-11.

Sugita M, et al. 'Failure of Trafficking and Antigen Presentation by CD1 in AP-3-Deficient Cells' Immunity. May 2002; 16(5):697-706.

Symes J, et al. 'Genetic Modification of T Lymphocytes for Cancer Therapy' Gene Therapy and Cancer Research Focus (2008): 163.

Udyavar A, et al. 'Rebalancing immune specificity and function in cancer by T-cell receptor gene therapy.' Arch Immunol Ther Exp (Warsz). Oct. 2010; 58(5):335-46. doi: 10.10071s00005-010-0090-1. Epub Aug. 1, 2010.

Udyavar A, et al. 'Subtle affinity-enhancing mutations in a myelin oligodendrocyte glycoprotein-specific TCR alter specificity and generate new self-reactivity' J Immunol. Apr. 1, 2009; 182(7):4439-47. doi: 10.4049/jimmunol.0804377.

Verneris MR, et al. 'Role of NKG2D signaling in the cytotoxicity of activated and expanded CD8+ T cells.' Blood. Apr. 15, 2004; 103(8):3065-72. Epub Nov. 20, 2003.

Voss RH, et al. 'Molecular design of the Cαβ interface favors specific pairing of introduced TCRαβ in human T cells' J Immunol. Jan. 1, 2008; 180(1):391-401.

Wang J, et al. 'Optimizing adoptive polyclonal T cell immunotherapy of lymphomas, using a chimeric T cell receptor possessing CD28 and CD137 costimulatory domains.' Hum Gene Ther. Aug. 2007; 18(8):712-25.

Weiss A, et al. 'Regulation of protein tyrosine kinase activation by the T-cell antigen receptor zeta chain.' Cold Spring Harb Symp Quant Biol. 1992;57:107-16.

Williams BL, et al. 'Genetic evidence for differential coupling of Syk family kinases to the T-cell receptor: reconstitution studies in a ZAP-70-deficient Jurkat T-cell line.' Mol Cell Biol. Mar. 1998; 18(3):1388-99.

Wu J, et al. 'An activating immunoreceptor complex formed by NKG2D and DAP10.' Science. Jul. 30, 1999; 285(5428):730-2.

Xu H, et al. 'A kinase-independent function of Lck in potentiating antigen-specific T cell activation.' Cell. Aug. 27, 1993; 74(4):633-43.

Yachi PP, et al. 'Altered Peptide Ligands Induce Delayed CD8-T Cell Receptor Interaction—a Role for CD8 in Distinguishing Antigen Quality' Immunity. Aug. 2006; 25(2):203-11. Epub Jul. 27, 2006.

Zhang T, et al. 'Generation of antitumor responses by genetic modification of primary human T cells with a chimeric NKG2D receptor.' Cancer Res. Jun. 1, 2006; 66(11):5927-33.

Zhao Y, et al. 'A Herceptin-Based Chimeric Antigen Receptor with Modified Signaling Domains Leads to Enhanced Survival of Transduced T Lymphocytes and Antitumor Activity' J Immunol. Nov. 1, 2009; 183(9):5563-74. doi: 10.4049/jimmunol.0900447.

(56) References Cited

OTHER PUBLICATIONS

Yu C, et al. 'Inhibitory signaling potential of a TCR-like molecule in lamprey.' Eur J Immunol. Feb. 2009; 39(2):571-9. doi: 10.1002/eji.200838846.

Lustgarten J, et al. "Specific elimination of IgE production using T cell lines expressing chimeric T cell receptor genes," Eur J Immunol. Oct. 1995; 25(10):2985-91.

Chae WJ, et al. "Qualitatively differential regulation of T cell activation and apoptosis by T cell receptor zeta chain ITAMs and their tyrosine residues," Int Immunol. Sep. 2004; 16(9):1225-36.

Hwang S, et al. "Reduced TCR signaling potential impairs negative selection but does not result in autoimmune lisease," J Exp Med. Sep. 24, 2012; 209(10)1781-95.

Liu CP, et al. "Abnormal T cell development in CD3-zeta-/-mutant mice and identification of a novel T cell population in the intestine," Embo J. Dec. 1993; 12(12):4863-75.

Love Pe, et al. "T cell development in mice that lack the zeta chain of the T cell antigen receptor complex," Science. Aug. 13, 1993; 261(5123):918-21.

Bitton N, et al. "Gene therapy approaches to Hiv-infection: immunological strategies: use of T bodies and universal receptors to redirect cytolytic T-cells," Front Biosci. Apr. 1, 1999; 4:D386-93.

Boon T, et al. "Human tumor antigens recognized by T lymphocytes," J Exp Med. Mar. 1, 1996; 183(3):725-9.

Call ME, et al. "Common themes in the assembly and architecture of activating immune receptors," Nat Rev Immunol. Nov. 2007; 7(11):841-50.

Call ME, et al. "The T cell receptor: critical role of the membrane environment in receptor assembly and function," Annu Rev Immunol. 2005;23:101-25.

Eshhar Z., "The T-Body Aporoach: Redirecting T Cells with Antibody Specificity," Therapeutic Antibodies 2008, vol. 181, pp. 329-342.

Fujisaki H, et al. "Replicative potential of human natural killer cells," Br J Haematol. Jun. 2009; 145(5):606-13.

Gonzalez S, et al. "Amplification of RNAi—targeting HLA mRNAs," Mol Ther. May 2005; 11(5):811-8.

Hege KM, et al. "Systemic T cell-independent tumor immunity after transplantation of universal receptor-modified bone marrow into Scid mice," J Exp Med. Dec. 1, 1996; 184(6):2261-9.

Hege KM, et al. "T-cell gene therapy," Curr Opin Biotechnol. Dec. 1996; 7(6):629-34.

Ho Wy, et al. "Adoptive immunotherapy: engineering T cell responses as biologic weapons for tumor mass destruction," Cancer Cell. May 2003; 3(5):431-7.

Imai C, et al. "Genetic modification of T cells for cancer therapy," J Biol Regul Homeost Agents. Jan.-Mar. 2004; 18(1):62-71.

Maher J, et al. "Targeting cytotoxic T lymphocytes for cancer immunotherapy," Br J Cancer. Aug. 31, 2004; 91(5):817-21.

Mitsuyasu RT, et al. "Prolonged survival and tissue trafficking following adoptive transfer of CD4zeta gene-modified autologous CD4(+) and CD8(+) T cells in human immunodeficiency virus-infected subjects," Blood. Aug. 1, 2000; 96(3):785-93.

Morris EC, et al. "Prospects for immunotherapy of malignant disease," Clin Exp Immunol. Jan. 2003; 131(1):1-7.

Morris K, et al. "Enhancing siRNA effects in T cells for adoptive immunotherapy," Hematology. Dec. 2005; 10(6):461-7.

Ribas A, et al. "Current developments in cancer vaccines and cellular immunotherapy," J Clin Oncol. Jun. 15, 2003; 21(12):2415-32.

Roberts MR, et al. "Antigen-specific cytolysis by neutrophils and NK cells expressing chimeric immune receptors bearing zeta or gamma signaling domains," J Immunol. Jul. 1, 1998; 161(1):375-84.

Roberts MR, et al. "Targeting of human immunodeficiency virus-infected cells by CD8+ T lymphocytes armed with universal T-cell receptors," Blood. Nov. 1, 1994; 84(9):2878-89.

Rosenberg SA "Progress in human tumour immunology and immunotherapy," Nature. May 17, 2001; 411(6835):380-4.

Tran AC, et al. "Chimeric zeta-receptors direct human natural killer (NK) effector function to permit killing of NK-resistant tumor cells and HIV-infected T lymphocytes," J Immunol. Jul. 15, 1995; 155(2):1000-9.

Walker RE, et al. "Long-term in vivo survival of receptor-modified syngeneic T cells in patients with human immunodeficiency virus infection," Blood. Jul. 15, 2000; 96(2):467-74.

Yang OO, et al. "Lysis of HIV-1-infected cells and inhibition of viral replication by universal receptor T cells," Proc Natl Acad Sci U S A. Oct. 14, 1997; 94(21):11478-83.

Yee C, et al. "Adoptive T cell therapy using antigen-specific CD8+ T cell clones for the treatment of patients with metastatic melanoma: in vivo persistence, migration, and antitumor effect of transferred T cells," Proc Nati Acad Sci U S A. Dec. 10, 2002; 99(25):16168-73.

Zhang T, et al. "Chimeric NK-receptor-bearing T cells mediate antitumor immunotherapy," Blood. Sep. 1, 2005; 106(5):1544-51.

* cited by examiner

SEQUENCE LISTING

```
<160> NUMBER OF SEQ ID NOS: 101

<210> SEQ ID NO 1
<211> LENGTH: 25
<212> TYPE: DNA
<213> ORGANISM: Artificial Sequence
<220> FEATURE:
<223> OTHER INFORMATION: TCR-beta shRNA sequence

<400> SEQUENCE: 1
agtgcgagga gattcggcag cttat                                        25

<210> SEQ ID NO 2
<211> LENGTH: 25
<212> TYPE: DNA
<213> ORGANISM: Artificial Sequence
<220> FEATURE:
<223> OTHER INFORMATION: TCR-beta shRNA sequence

<400> SEQUENCE: 2
gcgaggagat tcggcagctt atttc                                        25

<210> SEQ ID NO 3
<211> LENGTH: 25
<212> TYPE: DNA
<213> ORGANISM: Artificial Sequence
<220> FEATURE:
<223> OTHER INFORMATION: TCR-beta shRNA sequence

<400> SEQUENCE: 3
ccaccatcct ctatgagatc ttgct                                        25

<210> SEQ ID NO 4
<211> LENGTH: 25
<212> TYPE: DNA
<213> ORGANISM: Artificial Sequence
<220> FEATURE:
<223> OTHER INFORMATION: TCR-beta shRNA sequence

<400> SEQUENCE: 4
tcctctatga gatcttgcta gggaa                                        25

<210> SEQ ID NO 5
<211> LENGTH: 25
<212> TYPE: DNA
<213> ORGANISM: Artificial Sequence
<220> FEATURE:
<223> OTHER INFORMATION: TCR-alpha shRNA sequence

<400> SEQUENCE: 5
```

```
tctatggctt caactggcta gggtg                                          25

<210> SEQ ID NO 6
<211> LENGTH: 25
<212> TYPE: DNA
<213> ORGANISM: Artificial Sequence
<220> FEATURE:
<223> OTHER INFORMATION: TCR-alpha shRNA sequence

<400> SEQUENCE: 6
caggtagagg ccttgtccac ctaat                                          25

<210> SEQ ID NO 7
<211> LENGTH: 25
<212> TYPE: DNA
<213> ORGANISM: Artificial Sequence
<220> FEATURE:
<223> OTHER INFORMATION: TCR-alpha shRNA sequence

<400> SEQUENCE: 7
gcagcagaca ctgcttctta cttct                                          25

<210> SEQ ID NO 8
<211> LENGTH: 25
<212> TYPE: DNA
<213> ORGANISM: Artificial Sequence
<220> FEATURE:
<223> OTHER INFORMATION: TCR-alpha shRNA sequence

<400> SEQUENCE: 8
gacactgctt cttacttctg tgcta                                          25

<210> SEQ ID NO 9
<211> LENGTH: 25
<212> TYPE: DNA
<213> ORGANISM: Artificial Sequence
<220> FEATURE:
<223> OTHER INFORMATION: CD3-epsilon shRNA sequence

<400> SEQUENCE: 9
cctctgcctc ttatcagttg gcgtt                                          25

<210> SEQ ID NO 10
<211> LENGTH: 25
<212> TYPE: DNA
<213> ORGANISM: Artificial Sequence
<220> FEATURE:
<223> OTHER INFORMATION: CD3-epsilon shRNA sequence

<400> SEQUENCE: 10
gagcaaagtg gttattatgt ctgct                                          25

<210> SEQ ID NO 11
<211> LENGTH: 25
<212> TYPE: DNA
<213> ORGANISM: Artificial Sequence
<220> FEATURE:
<223> OTHER INFORMATION: CD3-epsilon shRNA sequence

<400> SEQUENCE: 11
aagcaaacca gaagatgcga acttt                                          25

<210> SEQ ID NO 12
<211> LENGTH: 25
<212> TYPE: DNA
```

```
<213> ORGANISM: Artificial Sequence
<220> FEATURE:
<223> OTHER INFORMATION: CD3-epsilon shRNA sequence

<400> SEQUENCE: 12
gacctgtatt ctggcctgaa tcaga                                              25

<210> SEQ ID NO 13
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 13
ggcctctgcc tcttatcagt t                                                  21

<210> SEQ ID NO 14
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 14
gcctctgcct cttatcagtt g                                                  21

<210> SEQ ID NO 15
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 15
gcctcttatc agttggcgtt t                                                  21

<210> SEQ ID NO 16
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 16
aggatcacct gtcactgaag g                                                  21

<210> SEQ ID NO 17
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 17
ggatcacctg tcactgaagg a                                                  21

<210> SEQ ID NO 18
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 18
gaattggagc aaagtggtta t                                                  21
```

<210> SEQ ID NO 19
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 19
ggagcaaagt ggttattatg t                                         21

<210> SEQ ID NO 20
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 20
gcaaaccaga agatgcgaac t                                         21

<210> SEQ ID NO 21
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 21
acctgtattc tggcctgaat c                                         21

<210> SEQ ID NO 22
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 22
gcctgaatca gagacgcatc t                                         21

<210> SEQ ID NO 23
<211> LENGTH: 29
<212> TYPE: DNA
<213> ORGANISM: Artificial Sequence
<220> FEATURE:
<223> OTHER INFORMATION: CD3-epsilon shRNA sequence

<400> SEQUENCE: 23
ctgaaatact atggcaacac aatgataaa                                 29

<210> SEQ ID NO 24
<211> LENGTH: 29
<212> TYPE: DNA
<213> ORGANISM: Artificial Sequence
<220> FEATURE:
<223> OTHER INFORMATION: CD3-epsilon shRNA sequence

<400> SEQUENCE: 24
aaacataggc agtgatgagg atcacctgt                                 29

<210> SEQ ID NO 25
<211> LENGTH: 29
<212> TYPE: DNA
<213> ORGANISM: Artificial Sequence
<220> FEATURE:

```
<223> OTHER INFORMATION: CD3-epsilon shRNA sequence

<400> SEQUENCE: 25
attgtcatag tggacatctg catcactgg                                           29

<210> SEQ ID NO 26
<211> LENGTH: 29
<212> TYPE: DNA
<213> ORGANISM: Artificial Sequence
<220> FEATURE:
<223> OTHER INFORMATION: CD3-epsilon shRNA sequence

<400> SEQUENCE: 26
ctgtattctg gcctgaatca gagacgcat                                           29

<210> SEQ ID NO 27
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 27
gatacctata gaggaacttg a                                                   21

<210> SEQ ID NO 28
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 28
gacagagtgt ttgtgaattg c                                                   21

<210> SEQ ID NO 29
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 29
gaacactgct ctcagacatt a                                                   21

<210> SEQ ID NO 30
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 30
ggacccacga ggaatatata g                                                   21

<210> SEQ ID NO 31
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 31
ggtgtaatgg gacagatata t                                                   21
```

```
<210> SEQ ID NO 32
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 32
gcaagttcat tatcgaatgt g                                              21

<210> SEQ ID NO 33
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 33
ggctggcatc attgtcactg a                                              21

<210> SEQ ID NO 34
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 34
gctggcatca ttgtcactga t                                              21

<210> SEQ ID NO 35
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 35
gcatcattgt cactgatgtc a                                              21

<210> SEQ ID NO 36
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 36
gctttgggag tcttctgctt t                                              21

<210> SEQ ID NO 37
<211> LENGTH: 29
<212> TYPE: DNA
<213> ORGANISM: Artificial Sequence
<220> FEATURE:
<223> OTHER INFORMATION: CD3-delta shRNA sequence

<400> SEQUENCE: 37
tggaacatag cacgtttctc tctggcctg                                      29

<210> SEQ ID NO 38
<211> LENGTH: 29
<212> TYPE: DNA
<213> ORGANISM: Artificial Sequence
<220> FEATURE:
<223> OTHER INFORMATION: CD3-delta shRNA sequence
```

```
<400> SEQUENCE: 38
ctgctctcag acattacaag actggacct                                    29

<210> SEQ ID NO 39
<211> LENGTH: 29
<212> TYPE: DNA
<213> ORGANISM: Artificial Sequence
<220> FEATURE:
<223> OTHER INFORMATION: CD3-delta shRNA sequence

<400> SEQUENCE: 39
accgtggctg gcatcattgt cactgatgt                                    29

<210> SEQ ID NO 40
<211> LENGTH: 29
<212> TYPE: DNA
<213> ORGANISM: Artificial Sequence
<220> FEATURE:
<223> OTHER INFORMATION: CD3-delta shRNA sequence

<400> SEQUENCE: 40
tgatgctcag tacagccacc ttggaggaa                                    29

<210> SEQ ID NO 41
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 41
ggctatcatt cttcttcaag g                                            21

<210> SEQ ID NO 42
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 42
gcccagtcaa tcaaaggaaa c                                            21

<210> SEQ ID NO 43
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 43
ggttaaggtg tatgactatc a                                            21

<210> SEQ ID NO 44
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 44
ggttcggtac ttctgacttg t                                            21

<210> SEQ ID NO 45
<211> LENGTH: 21
```

```
<212> TYPE: DNA
<213> ORGANISM: Artificial Sequence
<220> FEATURE:
<223> OTHER INFORMATION: CD3-gamma shRNA sequence

<400> SEQUENCE: 45
gaatgtgtca gaactgcatt g                                              21

<210> SEQ ID NO 46
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 46
gcagccacca tatctggctt t                                              21

<210> SEQ ID NO 47
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 47
ggctttctct ttgctgaaat c                                              21

<210> SEQ ID NO 48
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 48
gctttctctt tgctgaaatc g                                              21

<210> SEQ ID NO 49
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 49
gccaccttca aggaaaccag t                                              21

<210> SEQ ID NO 50
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 50
gaaaccagtt gaggaggaat t                                              21

<210> SEQ ID NO 51
<211> LENGTH: 29
<212> TYPE: DNA
<213> ORGANISM: Artificial Sequence
<220> FEATURE:
<223> OTHER INFORMATION: CD3-gamma shRNA sequence

<400> SEQUENCE: 51
```

```
ggctttctct ttgctgaaat cgtcagcat                                              29
```

<210> SEQ ID NO 52
<211> LENGTH: 29
<212> TYPE: DNA
<213> ORGANISM: Artificial Sequence
<220> FEATURE:
<223> OTHER INFORMATION: CD3-gamma shRNA sequence

<400> SEQUENCE: 52

```
aggatggagt tcgccagtcg agagcttca                                              29
```

<210> SEQ ID NO 53
<211> LENGTH: 29
<212> TYPE: DNA
<213> ORGANISM: Artificial Sequence
<220> FEATURE:
<223> OTHER INFORMATION: CD3-gamma shRNA sequence

<400> SEQUENCE: 53

```
cctcaaggat cgagaagatg accagtaca                                              29
```

<210> SEQ ID NO 54
<211> LENGTH: 29
<212> TYPE: DNA
<213> ORGANISM: Artificial Sequence
<220> FEATURE:
<223> OTHER INFORMATION: CD3-gamma shRNA sequence

<400> SEQUENCE: 54

```
tacagccacc ttcaaggaaa ccagttgag                                              29
```

<210> SEQ ID NO 55
<211> LENGTH: 17
<212> TYPE: PRT
<213> ORGANISM: Artificial Sequence
<220> FEATURE:
<223> OTHER INFORMATION: Immunoreceptor tyrosine-based activation motif
      (ITAM)
<220> FEATURE:
<221> NAME/KEY: VARIANT
<222> LOCATION: (1)..(1)
<223> OTHER INFORMATION: Xaa may be Asp or Glu
<220> FEATURE:
<221> NAME/KEY: VARIANT
<222> LOCATION: (2)..(3)
<223> OTHER INFORMATION: Xaa may be any amino acid
<220> FEATURE:
<221> NAME/KEY: VARIANT
<222> LOCATION: (5)..(6)
<223> OTHER INFORMATION: Xaa may be any amino acid
<220> FEATURE:
<221> NAME/KEY: VARIANT
<222> LOCATION: (7)..(7)
<223> OTHER INFORMATION: Xaa may be Ile or Leu
<220> FEATURE:
<221> NAME/KEY: VARIANT
<222> LOCATION: (8)..(13)
<223> OTHER INFORMATION: Xaa may be any amino acid
<220> FEATURE:
<221> NAME/KEY: VARIANT
<222> LOCATION: (15)..(16)
<223> OTHER INFORMATION: Xaa may be any amino acid
<220> FEATURE:
<221> NAME/KEY: VARIANT
<222> LOCATION: (17)..(17)
<223> OTHER INFORMATION: Xaa may be Ile or Leu

<400> SEQUENCE: 55

```
Xaa Xaa Xaa Tyr Xaa Xaa Xaa Xaa Xaa Xaa Xaa Xaa Xaa Tyr Xaa Xaa
1               5                   10                  15
```

Xaa

<210> SEQ ID NO 56
<211> LENGTH: 18
<212> TYPE: PRT
<213> ORGANISM: Artificial Sequence
<220> FEATURE:
<223> OTHER INFORMATION: Immunoreceptor tyrosine-based activation motif
      (ITAM)
<220> FEATURE:
<221> NAME/KEY: VARIANT
<222> LOCATION: (1)..(1)
<223> OTHER INFORMATION: Xaa may be Asp or Glu
<220> FEATURE:
<221> NAME/KEY: VARIANT
<222> LOCATION: (2)..(3)
<223> OTHER INFORMATION: Xaa may be any amino acid
<220> FEATURE:
<221> NAME/KEY: VARIANT
<222> LOCATION: (5)..(6)
<223> OTHER INFORMATION: Xaa may be any amino acid
<220> FEATURE:
<221> NAME/KEY: VARIANT
<222> LOCATION: (7)..(7)
<223> OTHER INFORMATION: Xaa may be Ile or Leu
<220> FEATURE:
<221> NAME/KEY: VARIANT
<222> LOCATION: (8)..(14)
<223> OTHER INFORMATION: Xaa may be any amino acid
<220> FEATURE:
<221> NAME/KEY: VARIANT
<222> LOCATION: (16)..(17)
<223> OTHER INFORMATION: Xaa may be any amino acid
<220> FEATURE:
<221> NAME/KEY: VARIANT
<222> LOCATION: (18)..(18)
<223> OTHER INFORMATION: Xaa may be Ile or Leu

<400> SEQUENCE: 56

Xaa Xaa Xaa Tyr Xaa Xaa Xaa Xaa Xaa Xaa Xaa Xaa Xaa Xaa Tyr Xaa
1               5                   10                  15

Xaa Xaa

<210> SEQ ID NO 57
<211> LENGTH: 19
<212> TYPE: PRT
<213> ORGANISM: Artificial Sequence
<220> FEATURE:
<223> OTHER INFORMATION: Immunoreceptor tyrosine-based activation motify
      (ITAM)
<220> FEATURE:
<221> NAME/KEY: VARIANT
<222> LOCATION: (1)..(1)
<223> OTHER INFORMATION: Xaa may be Asp or Glu
<220> FEATURE:
<221> NAME/KEY: VARIANT
<222> LOCATION: (2)..(3)
<223> OTHER INFORMATION: Xaa may be any amino acid
<220> FEATURE:
<221> NAME/KEY: VARIANT
<222> LOCATION: (5)..(6)
<223> OTHER INFORMATION: Xaa may be any amino acid
<220> FEATURE:
<221> NAME/KEY: VARIANT
<222> LOCATION: (7)..(7)
<223> OTHER INFORMATION: Xaa may be Ile or Leu
<220> FEATURE:
<221> NAME/KEY: VARIANT
<222> LOCATION: (8)..(16)
<223> OTHER INFORMATION: Xaa may be any amino acid
<220> FEATURE:
<221> NAME/KEY: VARIANT
<222> LOCATION: (17)..(18)
<223> OTHER INFORMATION: Xaa may be any amino acid

```
<220> FEATURE:
<221> NAME/KEY: VARIANT
<222> LOCATION: (19)..(19)
<223> OTHER INFORMATION: Xaa may be Ile or Leu

<400> SEQUENCE: 57

Xaa Xaa Xaa Tyr Xaa Xaa Xaa Xaa Xaa Xaa Xaa Xaa Xaa Xaa Xaa Tyr
1               5                   10                  15

Xaa Xaa Xaa

<210> SEQ ID NO 58
<211> LENGTH: 1575
<212> TYPE: DNA
<213> ORGANISM: Homo sapien

<400> SEQUENCE: 58
tgaggacata tctaaatttt ctagttttat agaaggcttt tatccacaag aatcaagatc      60
ttccctctct gagcaggaat cctttgtgca ttgaagactt tagattcctc tctgcggtag     120
acgtgcactt ataagtattt gatggggtgg attcgtggtc ggaggtctcg acacagctgg     180
gagatgagtg aatttcataa ttataacttg gatctgaaga agagtgattt ttcaacacga     240
tggcaaaagc aaagatgtcc agtagtcaaa agcaaatgta gagaaaatgc atctccattt     300
tttttctgct gcttcatcgc tgtagccatg ggaatccgtt tcattattat ggtagcaata     360
tggagtgctg tattcctaaa ctcattattc aaccaagaag ttcaaattcc cttgaccgaa     420
agttactgtg gcccatgtcc taaaaactgg atatgttaca aaataactg ctaccaattt      480 tttgatgaga gtaaaaactg gtatgagagc caggcttctt gtatgtctca aaatgccagc     540
cttctgaaag tatacagcaa agaggaccag gatttactta aactggtgaa gtcatatcat     600
tggatgggac tagtacacat tccaacaaat ggatcttggc agtgggaaga tggctccatt     660
ctctcaccca acctactaac aataattgaa atgcagaagg gagactgtgc actctatgcc     720
tcgagcttta aaggctatat agaaaactgt tcaactccaa atacatacat ctgcatgcaa     780
aggactgtgt aaagatgatc aaccatctca ataaaagcca ggaacagaga agagattaca     840
ccagcggtaa cactgccaac cgagactaaa ggaaacaaac aaaaacagga caaaatgacc     900
aaagactgtc agatttctta gactccacag gaccaaacca tagaacaatt tcactgcaaa     960
catgcatgat tctccaagac aaaagaagag agatcctaaa ggcaattcag atatccccaa    1020
ggctgcctct cccaccacaa gcccagagtg gatgggctgg gggagggtg ctgttttaat     1080 ttctaaaggt aggaccaaca cccaggggat cagtgaagga agagaaggcc agcagatcag    1140
tgagagtgca accccaccct ccacaggaaa ttgcctcatg ggcagggcca cagcagagag    1200
acacagcatg ggcagtgcct tccctgcctg tgggggtcat gctgccactt ttaatgggtc    1260
ctccacccaa cggggtcagg gaggtggtgc tgccctagtg ggccatgatt atcttaaagg    1320
cattattctc cagccttaag atcttaggac gtttcctttg ctatgatttg tacttgcttg    1380
agtcccatga ctgtttctct tcctctcttt cttccttttg gaatagtaat atccatccta    1440
tgtttgtccc actattgtat tttggaagca cataacttgt ttggtttcac aggttcacag    1500
ttaagaagga attttgcctc tgaataaata gaatcttgag tctcatgcaa aaaaaaaaa     1560 aaaaaaaaaa aaaaa                                                    1575

<210> SEQ ID NO 59
<211> LENGTH: 6098
<212> TYPE: DNA
<213> ORGANISM: Homo sapien
```

<400> SEQUENCE: 59

```
gcagttatca tagagcacag tccctcacat cacacagctg cagagatgag taaacaaaga      60
ggaaccttct cagaagtgag tctggcccag gacccaaagc ggcagcaaag gaaacctaaa     120
ggcataaaa gctccatttc aggaaccgaa caggaaatat tccaagtaga attaaatctt     180
caaaatcctt ccctgaatca tcaagggatt gataaaatat atgactgcca aggtaaaaca     240
ttaaatatat cttcaatatt attgttctag gatgtgcagt tgaatgcaga agggtgagga     300
aagattaggg aatattttgc acttgtgaga atcggagttc ataattggga tctaaaattc     360
taatatgaaa tcagaagact aattttattc gggcattgtt caactgtaat ctgcggtcca     420
ctcatggaac attatattta ctgaaaatga aatggtatat tctgagagaa agattactag     480
agtagatgta gatttagagg ccagagttta tcattatgtt tccctgtgca tgtgggttct     540
ctagtatgta attctctagt atgtaatcct aatcaactct ctatctcccc tctctcagtg     600
cctctatttc tctccctgca ggtttactgc cacctccaga gaagctcact gccgaggtcc     660
taggaatcat ttgcattgtc ctgatggcca ctgtgttaaa aacaatagtt cttattcctt     720
gtaagcatat tcttgaaaga ttagaaggga acgttttact ttaatgcttg gaagtgcctc     780
aaaatatttc atactgttga agaatagaac tcttatttta ctgtttcttt caaagatcta     840
ttacttcatt tatttttata gaaaagtta attttattaa agattgtccc cattttaaat     900
aacacacaaa gtttcaaagt aagaaactaa actcattatg gtttatctaa atattacttt     960
ttataaaat cattttaatt tttctgttac agtcctggaa cagaacaatt cttccccaaa    1020
tacaagaacc cagaaaagta cattttatt ttcaaagttc tgatattagt acaatttgga    1080
accaaaagta atatggttat tctgaatttt tcacaacata ataacaaaa tcattgtaga    1140
gaacatgtgt ttatttttg tgtgtaatct atatatatgt atatacatac acacacaaag    1200
atattttctg atttcataat tcaaaggcat gctatagaag aaaagtattt agaaaaacaa    1260
attaatttt gaaagtggtt acatcaaata ctacaagaga tggtgaagtt tgtgctaaag    1320
tcttttaaaaa tgtttatttc aaaggtctat tactttatat atttttatag aaaaagttaa    1380
ttttattaaa gattctcccc atttaaaata acacacaaag tttcaaagta agaaactaaa    1440
ctcgttatgg ttcatctaga tatcagtttt tataaaaatc attttaattt ttctattaca    1500
gtcctggagc agaacaattc ttccccgaat acaagaacgc agaaaggtac attttttattt    1560
tcaatgttct gatattagta caatttatat tttgtgtctg ttttaaggca tgtaaaagaa    1620
tagtggcatt tttgcagaaa ataagccata aattcagcca taaatatttg taagaaaga    1680
ttatgaggca gcatttcctt ttctccagtg agtagaaata ctcacttaaa atcattctac    1740
cctctttctc ccaattaaca gaggtttcct actgctgtga gatgatacca aataaataat    1800
tttactattc taaaaaagca gttgtgtatc agcgatgttc aacacatgtg tagagtgtat    1860
ttttgtttgt tcatttgctt tatatgggaa cacaattagg gaggagaggc taacccttgt    1920
ctgtgcatgt gtgtatgact gactcagtta ttaaaaatat acatttataa gcctgtaagg    1980
atgcgtaaat atgttaagca catatatgtt tatactgttg aaatatgtga actaatttc    2040
attttaaaa attcatattg gtctaaatag taattcatat ctttattagc acgtcattgt    2100
ggccattgtc ctgaggagtg gattacatat tccaacagtt gttattacat tggtaaggaa    2160
agaagaactt gggaagagag tttgctggcc tgtacttcga agaactccag tctgctttct    2220
atagataatg aagaagaaat ggtaagatgt aaatgtttca aacattttat gaaaagcttc    2280
```

```
cttcagtgaa taatacattt gtagaaaaca tccatatgtg tgtacatata tttatctcat    2340
atattttcaa gtgtatgtaa tattcaattg attgacttaa taatgttttt aaagttatat    2400
actgctaatg tacatttatt ttcagttttt gttttcaag gaaaaccatg cttctataag     2460
tgctttgaat ccacaataaa ttttgctatc taattttatc gggcatgata tcatctggtc    2520
atgcagattg atcacaaagt gaatgaatgc atgtgataca agtcagatca tgaaataaaa    2580
gtttccagct ctagcagttc caccoctgtg tatgccctca tcacttatcc tgactcctct    2640
ccaaaacgca gtcttgactt ttaatattat aaataatgat tgcctgttct tgaatttatt    2700
tatataaagg gaatcaaaca gtgtgaattt catgtctttt tcaatcctat ctgatatttg    2760
tgcaattcct ccatattatt gcagttatca gtagtatgtt actgttcact gctgtactat    2820
gtacaaagaa cagtaagaat ccattgagtc cttgtctctg gatggggaag tgggtctcat    2880
gccctcaggg acaaagagga ccctaggtgg tttacggtgc actgttagtc atgggtccc    2940 tttgctgatc ctcctcatcc acagccatcc tggtgtctct tggtatgaga aggaagcact    3000
ttctctagct ccatattggt agcaggtctc ctggtagatc atccttgcca gtggcaccag    3060
ccttgcctgg tattgtggag gggactctcc ttcgataccc tcctcctatt gccaggttgg    3120
gtgtagggaa acagcaggcc taggtcacct tcttctgtcg tgtggaggac ttaacatgct    3180
cacttggaca cttggttgat ccctgatgct agggtcccag acaatttcat ctttctcttt    3240 ccaccttta gagttctcca ttgcttttgt cttttcattaa tcccagagtt tatagttgtt    3300
tttagtaggg agtagcagag agagacgagt ctacaccacc tggccaggac ccctgttatt    3360
ccgcaaaaac cgaatcggat aaaaattgag ggcttatcta gttaaagaat ggtgtggtac    3420
ccagaaaacc caatctgtag cttccatgtc atctatttct gaatgacaac ccctcaattc    3480
ccttctaaat ctccaactct gagaaatata gcacaaaaat agattgattt agtcacagta    3540
tctggagaaa tgaatgcaca gtatcaggaa acttattaaa acccttcctg tgtttattct    3600
gttaattgga gtaactatta cattgcaaga attaaaatgt ctttattaac atgagaataa    3660
gaatgaaagt actaagtata aacgttgaag agttcattta aataaaaaat tcaaacatttt   3720 atgaaagttt ttggcactgc aaatagtggt tttcaacttt aatatattgt ttttgtaatg    3780
ttttcataat tattatttaa gtgaaaatta tttcttttct tttagaaatt tctggccagc    3840
attttacctt cctcatggat tggtgtgttt cgtaacagca gtcatcatcc atgggtgaca    3900
ataaatggtt tggctttcaa acataagtaa gttcttttgt atggcgctat ataaaaaata    3960
tatataaagg ataaattcag aagaataata tgaataaatt tatgtggaat cattgacatg    4020
aagaaagatg tggaaagtta gtgaaatgtt gatataaata ttttacaata gaccatagta    4080
gtccatatat ttcaaccgct cattggtctg ctagtaaccct tcttggttat cagatggacc    4140
aggggtgtcc catctttggc ttctgtgggc cacgttagaa gacgaatagt cttggcccac    4200
acatagaata cactaacact aacgatagct gacgagctaa aaaaaaaaaa aaatcacaga    4260
atgttttaag aaagtttacg tatttgtgtt gggccgcatt caaagctgtc ctgggtcacg    4320
tgcggcccat gggcagcgag ttggacaacc tcgagctgga ctatcaggga actgcagtgc    4380 ttgttttat taaaaagcca cgcttacttt tttacttaag aatatcctca aagcacaata    4440
atagtgctgt tggcatattg ctataatttt tttattacta gttattgttg tcaatctctt    4500
attgtgccta atttataaat taaactttat cacagttatg aatgtgtaga gaaaacataa    4560
tctctctata ggttctgcac tatctgccat ttcaggcatc cactgggtc ttgaaacata     4620 tccctcgtgg atgaagaggg actactctgt tgagtgttca gaataatgac tcttactaat    4680
```

```
attatgaaaa atttaattac ccttttccat gaaattcttt tcttacagta catggaaaat    4740
gctttcgtct catgaatcat ttgcttaaaa tgtaacagaa tatggatttt tctccattac    4800
aggataaaag actcagataa tgctgaactt aactgtgcag tgctacaagt aaatcgactt    4860
aaatcagccc agtgtggatc ttcaatgata tatcattgta agcataagct ttagaagtaa    4920
agcatttgcg tttacagtgc atcagataca ttttatattt cttaaaatag aaatattatg    4980
attgcataaa tctgaaaatg aattatgtta tttgctctaa tacaaaaatt ctaaatcaat    5040
tattgaaata ggatgcacac aattactaaa gtacagacat cctagcattt gtgtcgggct    5100
cattttgctc aacatggtat ttgtggtttt cagcctttct aaaagttgca tgttatgtga    5160
gtcagcttat aggaagtacc aagaacagtc aaacccatgg agacagaaag tagaatagtg    5220
gttgccaatg tctcagggag gttgaaatag gagatgacca ctaattgata gaacgtttct    5280
ttgtgtcgtg atgaaaactt tctaaatttc agtaatggtg atggttgtaa ctttgcgaat    5340
atactaaaca tcattgattt ttaatcattt taagtgcatg aaatgtatgc tttgtacatg    5400
acacttcaat aaagctatcc agaaaaaaaa aagcctctga tgggattgtt tatgactgca    5460
tttatctcta aagtaatttt aaagattagc ttctttataa tattgacttt tctaatcagt    5520
ataaagtgtt tccttcaatg tactgtgtta tctttaattt ctctctcttg tattttgtat    5580
tttgggggat tgaagtcata cagaaatgta ggtattttac attatgctt ttgtaaatgg     5640 catcctgatt ctaaaattcc ctttagtaat ttttgttgtt ataaatagaa atacaactga    5700
tgtctgcatt ttgatttat atctacttat tccactgatt ttatatattt aaatctatta     5760
tgtcaactat tgatttattt ctgggtgttc tatataacga gcaatttat ctgcaaatga     5820 tcacactttt atttttttta atccatgtgc tataacttag ttttattttc atttatttc     5880 actggctaag gttttatacc catagttgaa tagaaggcac aatcaaagtt ctttgtggat    5940
catatgcatc attttctggt tttggcaaaa aatacttcaa catgttatac atatttaaaa    6000
agcttggtgt tttttgcatc ctatctttct catatcgaag cagttttata atcctatttt    6060
ctaatagatt ttatcaattg taacaatttt tattaatt                            6098
```

<210> SEQ ID NO 60
<211> LENGTH: 3000
<212> TYPE: DNA
<213> ORGANISM: Homo sapien
<300> PUBLICATION INFORMATION:
<308> DATABASE ACCESSION NUMBER: AF072845
<309> DATABASE ENTRY DATE: 1998-06-22
<313> RELEVANT RESIDUES IN SEQ ID NO: (1)..(3000)

<400> SEQUENCE: 60

```
aattcccagc cctggagctg gcattccagt gggaggccac tctcagtttc acttggtgac      60
ctttcacagc actgaccatg ttggccctat ttctcccctg cttgcttgct tttctatttt    120
attttattat tacattttta ttgttagaga gagggtctca ttctgtcgcc caggctggag    180
tgcagtggca aagtggtgag atctcggctc actgcaacct ccacttgcct cagtctccca    240
agtagctggg attacaggag cctgacacca tgcccgggta attttttgtat ttttgtagag    300 acggggtttc accatattgg cttgaactcc tgatctcagg tgatccccc accttggcct     360 cccaaagtgc tgggattaca ggcatgagcc actgcggtgg cctctcccct gctttcaaga    420
tgccatgctc tcagggtcc cctccctctt tctccatttc cctggcaaag ttcctcctct     480
tcccccattc agtgtgtgtt gtgataggg cagaatcctg tctgcactca cttccttggt     540
```

```
gatctcaccc agtcttgtgg ctttaagtac catccataag ccatcaaccc ccaaatttac    600
atctccagac cagccttatc ccctgaactc ctaaatgcag tgaggttatt cagcatctcc    660
acagggagat tgtcaggcat tccaaccct gtatgcccaa acctcgtcac tttccccgca     720
aacccacttc cctacctttc atctctgcca gcagacactc ccatcttctc agcgtttcat    780
gccagaaggc ttggctgtct aggatccctc tcaaacacac ccacattcat ttaatcagca    840
aattttcttg ccctacctc caaaatattt ccagatctcc ctagcctgca cacccttgcc     900
acctgtcatt cccacttgga ccaggccagc agcctccctg gtctctctga ccctccccct    960
gagttcgttc accaaaggca gtaacggaga caccccctca acacacacag gaagcagatg   1020
gccttgacac cagcagggtg catccgcta ttgctacttc tctgctcccc cacagttcct    1080
ctggacttct ctggaccaca gtcctctgcc agaccctgc cagacccag tccaccatga     1140
tccatctggg tcacatcctc ttcctgcttt tgctcccagg tgaagccagt ggttacaggg   1200
gatggtaggc agagcgtttg tgagatgggt gcttgggtga cgtctgcagg gacgggtgat   1260
gaaagtgggg ttcttctccc tgcacccctt cccttctggg agatccattc tgcttcaggg   1320
cctgggtcct tggggggcgga aggggggtgag acagggagtt ctggaggggc tgcctgttag  1380
cgtcccttc tcatgctggg gtctctgctg ccacttccaa tttcttgtca ctctccatgt   1440
ctctgggagt ccccttccca tgtggtcctg ttccatctct ccagcctgga gattacttct   1500
caggacacta cctttccttc tctacacccct atttttggt ttgtttattt tgagatgggg   1560
tcttgctctg ttgtccaggc tggagtgcag tggcacaatc acggctcacg cagccttga    1620
cttcctgggc tcaggtgatc ctcccagctc agcctcccga gtaactggga ttacaggtgt   1680
gaaccaacac ttccagctaa tttttgtatt tcttgtagag acgaggtctc actatgttgc   1740
ccaggctggt ctcgaactcc tgggctcaag cgatcttcct gcctcggcct cccaaagtgc   1800
tgggatgaca ggcgtgagcc acggtgccag gctgagcatt ctgttttgtg gaccttctct   1860
ccaccctcat ccaccttctt tctctttcca cagtggctgc agctcagacg actccaggag   1920
agagatcatc actccctgcc ttttaccctg gcacttcagg tatcacttcc accccagaag   1980
cttggccaga ggctcccaga acaccccagt ggttctccag gtcaccatcc cacctcccgt   2040
ccccaaatca gaggatccgt gtccttctcc gagtcccaga atcagcgacc cccagcctgt   2100
gttcaggagc accccgtgtg cccgccgcac agccccgagg gtcctgggac accccagcct   2160
ctctgcatct gtctcccgtt tcattcccca agcgcaactc caaggaacct gggacccgcc   2220
ccctcgcagg ggacttcctc tctgcctgtg gccaaagcac agcccccagga cgcagagctt   2280
gagttgtctc cctgttccgg cccccactct ccaggctctt gttccggatg tgggtccctc   2340
tctctgccgc tcctggcagg cctcgtggct gctgatgcgg tggcatcgct gctcatcgtg   2400
ggggcggtgt tcctgtgcgc acgcccacgc cgcagccccg cccaaggtga gggcggagat   2460
gggcggggcc tggaaggtgt atagtgtccc taggagggg gtcccaggga gggggccctt    2520
ggggaagccc tggaggaggt gctggggaaa ccctggggga ggtgcctggg gaaccctg     2580
aggaaacccc tgaagcaggg ggtccccagg gaagtggaga tatgggtggt caagcttcat   2640
gctttctctc ccctatcccc agaagatggc aaagtctaca tcaacatgcc aggcaggggc   2700
tgaccctcct gcagcttgga cctttgactt ctgaccctct catcctggat ggtgtgtggt   2760
ggcacaggaa ccccgcccc aacttttgga ttgtaataaa acaattgaaa cacctgtagt    2820
cgtattcttt ctcaaagaac cccagagttc ccaaagcctc cctcccatga actgtttctg   2880
gatccaaggc cccctcagaa cccccacatg tccccatccc atcagcccaa ggatctggca   2940
```

```
taatgttttt gtgcttcatg tttattttag gagagtattg gggagcggtc tggtctctca    3000
```

<210> SEQ ID NO 61
<211> LENGTH: 604
<212> TYPE: DNA
<213> ORGANISM: Homo sapien
<300> PUBLICATION INFORMATION:
<308> DATABASE ACCESSION NUMBER: AF019562
<309> DATABASE ENTRY DATE: 1997-08-14
<313> RELEVANT RESIDUES IN SEQ ID NO: (1)..(604)

<400> SEQUENCE: 61

```
ccacgcgtcc gcgctgcgcc acatcccacc ggcccttaca ctgtggtgtc cagcagcatc     60
cggcttcatg gggggacttg aaccctgcag caggctcctg ctcctgcctc tcctgctggc    120
tgtaagtggt ctccgtcctg tccaggccca ggcccagagc gattgcagtt gctctacggt    180
gagcccgggc gtgctggcag ggatcgtgat gggagacctg gtgctgacag tgctcattgc    240
cctggccgtg tacttcctgg gccggctggt ccctcggggg cgaggggctg cggaggcagc    300
gacccggaaa cagcgtatca ctgagaccga gtcgccttat caggagctcc agggtcagag    360
gtcggatgtc tacagcgacc tcaacacaca gaggccgtat tacaaatgag cccgaatcat    420
gacagtcagc aacatgatac ctggatccag ccattcctga gcccaccct gcacctcatt    480
ccaactccta ccgcgataca gacccacaga gtgccatccc tgagagacca gaccgctccc    540
caatactctc ctaaaataaa catgaagcac aaaaaaaaaa aaaaaaaaa aaaaaaaaa     600
aaaa                                                                 604
```

<210> SEQ ID NO 62
<211> LENGTH: 1677
<212> TYPE: DNA
<213> ORGANISM: Homo sapien
<300> PUBLICATION INFORMATION:
<308> DATABASE ACCESSION NUMBER: NM_198053
<309> DATABASE ENTRY DATE: 2010-08-01
<313> RELEVANT RESIDUES IN SEQ ID NO: (1)..(1677)

<400> SEQUENCE: 62

```
gtcctccact tcctggggag gtagctgcag aataaaacca gcagagactc cttttctcct     60
aaccgtcccg ccaccgctg cctcagcctc tgcctcccag cctctttctg agggaaagga    120
caagatgaag tggaaggcgc ttttcaccgc ggccatcctg caggcacagt tgccgattac    180
agaggcacag agctttggcc tgctggatcc caaactctgc tacctgctgg atggaatcct    240
cttcatctat ggtgtcattc tcactgcctt gttcctgaga gtgaagttca gcaggagcgc    300
agacgccccc gcgtaccagc agggccagaa ccagctctat aacgagctca atctaggacg    360
aagagaggag tacgatgttt tggacaagag acgtggccgg gaccctgaga tggggggaaa    420
gccgcagaga aggaagaacc ctcaggaagg cctgtacaat gaactgcaga agataagat    480
ggcggaggcc tacagtgaga ttgggatgaa aggcgagcgc cggagggggca aggggcacga    540
tggcctttac caggggtctca gtacagccac caaggacacc tacgacgccc ttcacatgca    600
ggccctgccc cctcgctaac agccagggga tttcaccact caaaggccag acctgcagac    660
gcccagatta tgagacacag gatgaagcat ttacaaccccg gttcactctt tcagccact    720
gaagtattcc cctttatgta caggatgctt tggttatatt tagctccaaa ccttcacaca    780
cagactgttg tccctgcact cttttaaggga gtgtactccc agggcttacg gccctggcct    840
tgggccctct ggtttgccgg tggtgcaggt agacctgtct cctggcggtt cctcgttctc    900
```

| | |
|---|---|
| cctgggaggc gggcgcactg cctctcacag ctgagttgtt gagtctgttt tgtaaagtcc | 960 |
| ccagagaaag cgcagatgct agcacatgcc ctaatgtctg tatcactctg tgtctgagtg | 1020 |
| gcttcactcc tgctgtaaat ttggcttctg ttgtcacctt cacctccttt caaggtaact | 1080 |
| gtactgggcc atgttgtgcc tccctggtga gagggccggg cagaggggca gatggaaagg | 1140 |
| agcctaggcc aggtgcaacc agggagctgc aggggcatgg gaaggtgggc gggcagggga | 1200 |
| gggtcagcca gggcctgcga gggcagcggg agcctccctg cctcaggcct ctgtgccgca | 1260 |
| ccattgaact gtaccatgtg ctacagggc cagaagatga acagactgac cttgatgagc | 1320 |
| tgtgcacaaa gtggcataaa aaacatgtgg ttacacagtg tgaataaagt gctgcggagc | 1380 |
| aagaggaggc cgttgattca cttcacgctt tcagcgaatg acaaaatcat ctttgtgaag | 1440 |
| gcctcgcagg aagacccaac acatgggacc tataactgcc cagcggacag tgcaggaca | 1500 |
| ggaaaaaccc gtcaatgtac taggatactg ctgcgtcatt acagggcaca ggccatggat | 1560 |
| ggaaaacgct ctctgctctg cttttttct actgttttaa tttatactgg catgctaaag | 1620 |
| ccttcctatt ttgcataata aatgcttcag tgaaaaaaaa aaaaaaaaaa aaaaaaa | 1677 |

<210> SEQ ID NO 63
<211> LENGTH: 591
<212> TYPE: DNA
<213> ORGANISM: Homo sapien
<300> PUBLICATION INFORMATION:
<308> DATABASE ACCESSION NUMBER: M33195
<309> DATABASE ENTRY DATE: 1993-04-27
<313> RELEVANT RESIDUES IN SEQ ID NO: (1)..(591)

<400> SEQUENCE: 63

| | |
|---|---|
| cagaacggcc gatctccagc ccaagatgat tccagcagtg gtcttgctct tactccttt | 60 |
| ggttgaacaa gcagcggccc tgggagagcc tcagctctgc tatatcctgg atgccatcct | 120 |
| gtttctgtat ggaattgtcc tcaccctcct ctactgtcga ctgaagatcc aagtgcgaaa | 180 |
| ggcagctata accagctatg agaaatcaga tggtgtttac acgggcctga gcaccaggaa | 240 |
| ccaggagact tacgagactc tgaagcatga aaaccacca cagtagcttt agaatagatg | 300 |
| cggtcatatt cttctttggc ttctggttct tccagccctc atggttggca tcacatatgc | 360 |
| ctgcatgcca ttaacaccag ctggccctac ccctataatg atcctgtgtc ctaaattaat | 420 |
| atacaccagt ggttcctcct ccctgttaaa gactaatgct cagatgctgt ttacggatat | 480 |
| ttatattcta gtctcactct cttgtcccac ccttcttctc ttccccattc ccaactccag | 540 |
| ctaaaatatg ggaagggaga accccccaata aaactgccat ggactggact c | 591 |

<210> SEQ ID NO 64
<211> LENGTH: 1687
<212> TYPE: DNA
<213> ORGANISM: Homo sapiens

<400> SEQUENCE: 64

| | |
|---|---|
| tgctttctca aaggccccac agtcctccac ttcctgggga ggtagctgca gaataaaacc | 60 |
| agcagagact cctttttctcc taaccgtccc ggccaccgct gcctcagcct ctgcctccca | 120 |
| gcctctttct gagggaaagg acaagatgaa gtggaaggcg cttttcaccg cggccatcct | 180 |
| gcaggcacag ttgccgatta cagaggcaca gagctttggc ctgctggatc ccaaactctg | 240 |
| ctacctgctg gatggaatcc tcttcatcta tggtgtcatt ctcactgcct tgttcctgag | 300 |
| agtgaagttc agcaggagcg cagacgcccc cgcgtaccag cagggccaga accagctcta | 360 |
| taacgagctc aatctaggac gaagagagga gtacgatgtt ttggacaaga gacgtggccg | 420 |

```
ggaccctgag atgggggaa  agccgagaag gaagaaccct caggaaggcc tgtacaatga   480
actgcagaaa gataagatgg cggaggccta cagtgagatt gggatgaaag gcagcgccg    540
gaggggcaag gggcacgatg gcctttacca gggtctcagt acagccacca aggacaccta   600
cgacgccctt cacatgcagg ccctgccccc tcgctaacag ccaggggatt tcaccactca   660
aaggccagac ctgcagacgc ccagattatg agacacagga tgaagcattt acaacccggt   720
tcactcttct cagccactga agtattcccc tttatgtaca ggatgctttg gttatattta   780
gctccaaacc ttcacacaca gactgttgtc cctgcactct ttaagggagt gtactcccag   840
ggcttacggc cctggccttg ggccctctgg tttgccggtg gtgcaggtag acctgtctcc   900
tggcggttcc tcgttctccc tgggaggcgg gcgcactgcc tctcacagct gagttgttga   960
gtctgttttg taaagtcccc agagaaagcg cagatgctag cacatgccct aatgtctgta  1020
tcactctgtg tctgagtggc ttcactcctg ctgtaaattt ggcttctgtt gtcaccttca  1080
cctcctttca aggtaactgt actgggccat gttgtgcctc cctggtgaga gggccgggca  1140
gaggggcaga tggaaaggag cctaggccag gtgcaaccag ggagctgcag ggcatggga   1200
aggtgggcgg gcaggggagg gtcagccagg gcctgcgagg gcagcgggag cctccctgcc  1260
tcaggcctct gtgccgcacc attgaactgt accatgtgct acaggggcca aagatgaac   1320
agactgacct tgatgagctg tgcacaaagt ggcataaaaa acatgtggtt acacagtgtg  1380
aataaagtgc tgcggagcaa gaggaggccg ttgattcact tcacgctttc agcgaatgac  1440
aaaatcatct ttgtgaaggc ctcgcaggaa gacccaacac atgggaccta taactgccca  1500
gcggacagtg gcaggacagg aaaaacccgt caatgtacta ggatactgct gcgtcattac  1560
agggcacagg ccatggatgg aaaacgctct ctgctctgct ttttttctac tgtttaatt   1620
tatactggca tgctaaagcc ttcctattt  gcataataaa tgcttcagtg aaaatgcaaa  1680
aaaaaaa                                                            1687
```

<210> SEQ ID NO 65
<211> LENGTH: 163
<212> TYPE: PRT
<213> ORGANISM: Homo sapiens

<400> SEQUENCE: 65

```
Met Lys Trp Lys Ala Leu Phe Thr Ala Ala Ile Leu Gln Ala Gln Leu
1               5                   10                  15

Phe Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140
```

Ser Thr Ala Thr Lys Asp Thr Tyr Asp Ala Leu His Met Gln Ala Leu
145                 150                 155                 160

Pro Pro Arg

<210> SEQ ID NO 66
<211> LENGTH: 255
<212> TYPE: DNA
<213> ORGANISM: Homo sapiens

<400> SEQUENCE: 66
catcgctggt gctccaacaa aaaaaatgct gcggtaatgg accaagagtc tgcaggaaac     60
agaacagcga atagcaagga ctctgatgaa caagaccctc aggaggtgac atacacacag    120
ttgaatcact gcgttttcac acagagaaaa atcactcacc cttctcagag gcccaagaca    180
cccccaacag atatcatcat gtacacggaa cttccaaatg ctgagtccag atccaaagtt    240
gtctcctgcc catga                                                     255

<210> SEQ ID NO 67
<211> LENGTH: 84
<212> TYPE: PRT
<213> ORGANISM: Homo sapiens

<400> SEQUENCE: 67

His Arg Trp Cys Ser Asn Lys Lys Asn Ala Ala Val Met Asp Gln Glu
1               5                   10                  15

Ser Ala Gly Asn Arg Thr Ala Asn Ser Glu Asp Ser Asp Glu Gln Asp
            20                  25                  30

Pro Gln Glu Val Thr Tyr Thr Gln Leu Asn His Cys Val Phe Thr Gln
        35                  40                  45

Arg Lys Ile Thr Arg Pro Ser Gln Arg Pro Lys Thr Pro Pro Thr Asp
    50                  55                  60

Ile Ile Val Tyr Thr Glu Leu Pro Asn Ala Glu Ser Arg Ser Lys Val
65                  70                  75                  80

Val Ser Cys Pro

<210> SEQ ID NO 68
<211> LENGTH: 97
<212> TYPE: DNA
<213> ORGANISM: Artificial Sequence
<220> FEATURE:
<223> OTHER INFORMATION: CD3-zeta shRNA sequence

<400> SEQUENCE: 68
tgctgttgac agtgagcgac ctcttgccag gatatttatt tagtgaagcc acagatgtaa     60
ataaatatcc tggcaagagg gtacctactg cctcgga                             97

<210> SEQ ID NO 69
<211> LENGTH: 97
<212> TYPE: DNA
<213> ORGANISM: Artificial Sequence
<220> FEATURE:
<223> OTHER INFORMATION: CD3-zeta shRNA sequence

<400> SEQUENCE: 69
tgctgttgac agtgagcgac cctcttgcca ggatatttat tagtgaagcc acagatgtaa     60
taaatatcct ggcaagaggg ctgcctactg cctcgga                             97

<210> SEQ ID NO 70

```
<211> LENGTH: 97
<212> TYPE: DNA
<213> ORGANISM: Artificial Sequence
<220> FEATURE:
<223> OTHER INFORMATION: CD3-zeta shRNA sequence

<400> SEQUENCE: 70
tgctgttgac agtgagcgac ctcagtatcc tggatctgaa tagtgaagcc acagatgtat      60
tcagatccag gatactgagg gtgcctactg cctcgga                              97

<210> SEQ ID NO 71
<211> LENGTH: 97
<212> TYPE: DNA
<213> ORGANISM: Artificial Sequence
<220> FEATURE:
<223> OTHER INFORMATION: CD3-zeta shRNA sequence

<400> SEQUENCE: 71
tgctgttgac agtgagcgcg gatggaatcc tcttcatcta tagtgaagcc acagatgtat      60
agatgaagag gattccatcc atgcctactg cctcgga                              97

<210> SEQ ID NO 72
<211> LENGTH: 528
<212> TYPE: DNA
<213> ORGANISM: Homo sapiens

<400> SEQUENCE: 72
atgaaaaacg tgttcccacc cgaggtcgct gtgtttgagc catcagaagc agagatctcc      60
cacacccaaa aggccacact ggtgtgcctg gccacaggct tctacccgga ccacgtggag     120
ctgagctggt gggtgaatgg aaggaggtg cacagtgggg tcagcacaga cccgcagccc     180
ctcaaggagc agcccgccct caatgactcc agatactgcc tgagcagccg cctgagggtc     240
tcggccacct tctggcagaa ccccgcaac cacttccgct gtcaagtcca gttctacggg     300
ctctcggaga tgacgagtg gacccaggat agggccaaac ctgtcaccca gatcgtcagc     360
gccgaggcct ggggtagagc agactgtggc ttcacctccg agtcttacca gcaagggtc     420 ctgtctgcca ccatcctcta tgagatcttg ctagggaagg ccaccttgta tgccgtgctg     480
gtcagtgccc tcgtgctgat ggccatggtc aagagaaagg atttctaa                  528

<210> SEQ ID NO 73
<211> LENGTH: 175
<212> TYPE: PRT
<213> ORGANISM: Homo sapiens

<400> SEQUENCE: 73

Met Lys Asn Val Phe Pro Pro Glu Val Ala Val Phe Glu Pro Ser Glu
1               5                   10                  15

Ala Glu Ile Ser His Thr Gln Lys Ala Thr Leu Val Cys Leu Ala Thr
                20                  25                  30

Gly Phe Tyr Pro Asp His Val Glu Leu Ser Trp Trp Val Asn Gly Leu
            35                  40                  45

Glu Val His Ser Gly Val Ser Thr Asp Pro Gln Pro Leu Lys Glu Gln
        50                  55                  60

Pro Ala Leu Asn Asp Ser Arg Tyr Cys Leu Ser Ser Arg Leu Arg Val
65                  70                  75                  80

Ser Ala Thr Phe Trp Gln Asn Pro Arg Asn His Phe Arg Cys Gln Val
                85                  90                  95

Gln Phe Tyr Gly Leu Ser Glu Asn Asp Glu Trp Thr Gln Asp Arg Ala
```

```
                100               105                110
Lys Pro Val Thr Gln Ile Val Ser Ala Glu Ala Trp Gly Arg Ala Asp
            115                 120                 125

Cys Gly Phe Thr Ser Glu Ser Tyr Gln Gln Gly Val Leu Ser Ala Thr
        130                 135                 140

Ile Leu Tyr Glu Ile Leu Leu Gly Lys Ala Thr Leu Tyr Ala Val Leu
145                 150                 155                 160

Val Ser Ala Leu Val Leu Met Ala Met Val Lys Arg Lys Asp Phe
                165                 170                 175

<210> SEQ ID NO 74
<211> LENGTH: 168
<212> TYPE: DNA
<213> ORGANISM: Homo sapiens

<400> SEQUENCE: 74
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtc tcattctcac tgccttgttc ctgagagtga agttcagc                  168

<210> SEQ ID NO 75
<211> LENGTH: 56
<212> TYPE: PRT
<213> ORGANISM: Homo sapiens

<400> SEQUENCE: 75

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser
    50                  55

<210> SEQ ID NO 76
<211> LENGTH: 189
<212> TYPE: DNA
<213> ORGANISM: Homo sapiens

<400> SEQUENCE: 76
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtg tcattctcac tgccttgttc ctgagagtga agttcagcag gagcgcagac     180
gcccccgcg                                                             189

<210> SEQ ID NO 77
<211> LENGTH: 63
<212> TYPE: PRT
<213> ORGANISM: Homo sapiens

<400> SEQUENCE: 77

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
```

```
                  35                  40                  45
Leu Phe Leu Arg Val Lys Phe Ser Arg Ser Ala Asp Ala Pro Ala
         50                  55                  60
```

<210> SEQ ID NO 78
<211> LENGTH: 214
<212> TYPE: DNA
<213> ORGANISM: Homo sapiens

<400> SEQUENCE: 78

```
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtg tcattctcac tgccttgttc ctgagagtga agttcagcag agcgcagac      180 gcccccgcgt accagcaggg ccagaaccca gctc                                  214
```

<210> SEQ ID NO 79
<211> LENGTH: 71
<212> TYPE: PRT
<213> ORGANISM: Homo sapiens

<400> SEQUENCE: 79

```
Met Lys Trp Lys Ala Leu Phe Thr Ala Ala Ile Leu Gln Ala Gln Leu
1               5                  10                  15
Pro Ile Thr Glu Ala Gln Ser Phe Gly Leu Leu Asp Pro Lys Leu Cys
             20                  25                  30
Tyr Leu Leu Asp Gly Ile Leu Phe Ile Tyr Gly Val Ile Leu Thr Ala
         35                  40                  45
Leu Phe Leu Arg Val Lys Phe Ser Arg Ser Ala Asp Ala Pro Ala Tyr
     50                  55                  60
Gln Gln Gly Gln Asn Pro Ala
65                  70
```

<210> SEQ ID NO 80
<211> LENGTH: 423
<212> TYPE: DNA
<213> ORGANISM: Homo sapiens

<400> SEQUENCE: 80

```
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtg tcattctcac tgccttgttc ctgagagtga agttcagcca tcgctggtgc     180
tccaacaaaa aaaatgctgc ggtaatggac caagagtctg caggaaacag aacagcgaat     240
agcgaggact ctgatgaaca agaccctcag gaggtgacat acacacagtt gaatcactgc     300
gttttcacac agagaaaaat cactcgaaat tctcagaggc caagacaccc ccaacagat     360 atcatcatgt acacggaact tccaaatgct gagtccagat ccaaagttgt ctcctgccca     420
tga                                                                    423
```

<210> SEQ ID NO 81
<211> LENGTH: 140
<212> TYPE: PRT
<213> ORGANISM: Homo sapiens

<400> SEQUENCE: 81

```
Met Lys Trp Lys Ala Leu Phe Thr Ala Ala Ile Leu Gln Ala Gln Leu
1               5                  10                  15
```

```
Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser His Arg Trp Cys Ser Asn Lys Lys
50                  55                  60

Asn Ala Ala Val Met Asp Gln Glu Ser Ala Gly Asn Arg Thr Ala Asn
65                  70                  75                  80

Ser Glu Asp Ser Asp Glu Gln Asp Pro Gln Val Thr Tyr Thr Gln
                85                  90                  95

Leu Asn His Cys Val Phe Thr Gln Arg Lys Ile Thr Arg Pro Ser Gln
                100                 105                 110

Arg Pro Lys Thr Pro Pro Thr Asp Ile Ile Val Tyr Thr Glu Leu Pro
            115                 120                 125

Asn Ala Glu Ser Arg Ser Lys Val Val Ser Cys Pro
            130                 135                 140
```

<210> SEQ ID NO 82
<211> LENGTH: 444
<212> TYPE: DNA
<213> ORGANISM: Homo sapiens

<400> SEQUENCE: 82

```
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtg tcattctcac tgccttgttc ctgagagtga agttcagcag agcgcagac     180
gcccccgcgc atcgctggtg ctccaacaaa aaaaatgctg cggtaatgga ccaagagtct     240
gcaggaaaca gaacagcgaa tagcgaggac tctgatgaac aagaccctca ggaggtgaca     300
tacacacagt tgaatcactg cgttttcaca cagagaaaaa tcactcgccc ttctcagagg     360
cccaagacac ccccaacaga tatcatcgtg tacacggaac ttccaaatgc tgagtccaga     420
tccaaagttg tctcctgccc atga                                             444
```

<210> SEQ ID NO 83
<211> LENGTH: 147
<212> TYPE: PRT
<213> ORGANISM: Homo sapiens

<400> SEQUENCE: 83

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala His
50                  55                  60

Arg Trp Cys Ser Asn Lys Lys Asn Ala Ala Val Met Asp Gln Glu Ser
65                  70                  75                  80

Ala Gly Asn Arg Thr Ala Asn Ser Glu Asp Ser Asp Glu Gln Asp Pro
                85                  90                  95

Gln Glu Val Thr Tyr Thr Gln Leu Asn His Cys Val Phe Thr Gln Arg
                100                 105                 110

Lys Ile Thr Arg Pro Ser Gln Arg Pro Lys Thr Pro Pro Thr Asp Ile
            115                 120                 125
```

Ile Val Tyr Thr Glu Leu Pro Asn Ala Glu Ser Arg Ser Lys Val Val
            130                 135                 140

Ser Cys Pro
145

<210> SEQ ID NO 84
<211> LENGTH: 471
<212> TYPE: DNA
<213> ORGANISM: Homo sapiens

<400> SEQUENCE: 84
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtg tcattctcac tgccttgttc ctgagagtga agttcagcag agcgcagac      180 gcccccgcgt accagcaggg ccagaaccag ctccatcgct ggtgctccaa caaaaaaaat     240
gctgcggtaa tggaccaaga gtctgcagga aacagaacag cgaatagcga ggactctgat     300
gaacaagacc ctcaggaggt gacatacaca cagttgaatc actgcgtttt cacacagaga     360
aaaatcactc gcccttctca gaggcccaag acaccccccaa cagatatcat cgtgtacacg     420
gaacttccaa atgctgagtc cagatccaaa gttgtctcct gcccatgagc a              471

<210> SEQ ID NO 85
<211> LENGTH: 155
<212> TYPE: PRT
<213> ORGANISM: Homo sapiens

<400> SEQUENCE: 85

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Pro Ala His Arg Trp Cys Ser Asn Lys Lys Asn
65                  70                  75                  80

Ala Ala Val Met Asp Gln Glu Ser Ala Gly Asn Arg Thr Ala Asn Ser
                85                  90                  95

Glu Asp Ser Asp Glu Gln Asp Pro Gln Glu Val Thr Tyr Thr Gln Leu
            100                 105                 110

Asn His Cys Val Phe Thr Gln Arg Lys Ile Thr Arg Pro Ser Gln Arg
        115                 120                 125

Pro Lys Thr Pro Pro Thr Asp Ile Ile Val Tyr Thr Glu Leu Pro Asn
    130                 135                 140

Ala Glu Ser Arg Ser Lys Val Val Ser Cys Pro
145                 150                 155

<210> SEQ ID NO 86
<211> LENGTH: 618
<212> TYPE: DNA
<213> ORGANISM: Homo sapiens

<400> SEQUENCE: 86
atgaagtgga aggcgctttt caccgcggcc atcctgcagg cacagttgcc gattacagag      60

| | | |
|---|---|---|
| gcacagagct ttggcctgct ggatcccaaa ctctgctacc tgctggatgg aatcctcttc | 120 | |
| atgtatggtg tcattctcac tgccttgttc ctgagagtga agttcagcag gagcgcagac | 180 | |
| gcccccgcgt tccagcaggg ccagaaccag ctctataacg agctcaatct aggacgaaga | 240 | |
| gaggagtacg atgttttgga caagagacgt ggccgggacc ctgagatggg gggaaagccg | 300 | |
| agccggaaga accctcagga aggcctgtac aatgaactgc agaaagataa gatggcggag | 360 | |
| gcccatcgct ggtgctccaa caaaaaaaat gctgcggtaa tggaccaaga gtctgcagga | 420 | |
| aacagaacag cgaatagcga ggactctgat gaacaagacc ctcaggaggt gacatacaca | 480 | |
| cagttgaatc actgcgtttt cacacagaga aaaatcactc gcccttctca gaggcccaag | 540 | |
| acaccccccaa cagatatcat cgtgtacacg gaacttccaa atgctgagtc cagatccaaa | 600 | |
| gttgtctcct gcccatga | 618 | |

<210> SEQ ID NO 87
<211> LENGTH: 205
<212> TYPE: PRT
<213> ORGANISM: Homo sapiens

<400> SEQUENCE: 87

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Phe
    50                  55                  60

Gln Gln Gly Gln Asn Gln Leu Tyr Asn Glu Leu Asn Leu Gly Arg Arg
65                  70                  75                  80

Glu Gly Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala His Arg Trp Cys Ser Asn Lys
        115                 120                 125

Lys Asn Ala Ala Val Met Asp Gln Glu Ser Ala Gly Asn Arg Thr Ala
    130                 135                 140

Asn Ser Glu Asp Ser Asp Glu Gln Asp Pro Gln Glu Val Thr Tyr Thr
145                 150                 155                 160

Gln Leu Asn His Cys Val Phe Thr Gln Arg Lys Ile Thr Arg Pro Ser
                165                 170                 175

Gln Arg Pro Lys Thr Pro Pro Thr Asp Ile Ile Val Tyr Thr Glu Leu
            180                 185                 190

Pro Asn Ala Glu Ser Arg Ser Lys Val Val Ser Cys Pro
        195                 200                 205

<210> SEQ ID NO 88
<211> LENGTH: 708
<212> TYPE: DNA
<213> ORGANISM: Homo sapiens

<400> SEQUENCE: 88

| | | |
|---|---|---|
| atgaagtgga aggcgctttt caccgcggcc atcctgcagg cacagttgcc gattacagag | 60 | |
| gcacagagct ttggcctgct ggatcccaaa ctctgctacc tgctggatgg aatcctcttc | 120 | |

```
atctatggtg tcattctcac tgccttgttc ctgagagtga agttcagcag gagcgcagac    180
gaaaaagcgt accagcaggg ccagaaccag ctctataacg agctcaatct aggacgaaga    240
gaggagtacg atgttttgga caagagacgt ggccgggacc ctgagatggg gggaaagccg    300
agaaggaaga accctcagga aggcctgtac aatgaactgc agaaagataa gatggcggag    360
gccttcagtg agattgggat gaaaggcgag cgccggaggg gcaaggggca cgatggcctt    420
taccagggtc tcagtacagc caccaaggac acccatcgct ggtgctccaa caaaaaaaat    480
gctgcggtaa tggaccaaga gtctgcagga acagaacag cgaatagcga ggactctgat    540
gaacaagacc ctcaggaggt gacatacaca cagttgaatc actgcgtttt cacacagaga    600
aaaatcactc gcccttctca gaggcccaag acacccccaa cagatatcat cgtgtacacg    660
gaacttccaa atgctgagtc cagatccaaa gttgtctcct gcccatga               708
```

<210> SEQ ID NO 89
<211> LENGTH: 235
<212> TYPE: PRT
<213> ORGANISM: Homo sapiens

<400> SEQUENCE: 89

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
            85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Phe Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr His Arg Trp Cys Ser Asn Lys Lys Asn
145                 150                 155                 160

Ala Ala Val Met Asp Gln Glu Ser Ala Gly Asn Arg Thr Ala Asn Ser
            165                 170                 175

Glu Asp Ser Asp Glu Gln Asp Pro Gln Glu Val Thr Tyr Thr Gln Leu
        180                 185                 190

Asn His Cys Val Phe Thr Gln Arg Lys Ile Thr Arg Pro Ser Glu Arg
    195                 200                 205

Pro Lys Thr Pro Pro Thr Asp Ile Ile Val Tyr Thr Glu Leu Pro Asn
        210                 215                 220

Ala Glu Ser Arg Ser Lys Val Val Ser Cys Pro
225                 230                 235
```

<210> SEQ ID NO 90
<211> LENGTH: 492
<212> TYPE: DNA
<213> ORGANISM: Homo sapiens

<400> SEQUENCE: 90

```
atgaagtgga aggcgctttt caccgcggcc atcctgcagg cacagttgcc gattacagag      60
gcacagagct ttggcctgct ggatcccaaa ctctgctacc tgctggctgg aatcctcttc     120
atctatggtg tcattctcac tgccttgttc ctgagagtga agttcagcag agcgcagac      180
gcccccgcgt accagcaggg ccagaaccag ctctataacg agctcaatct aggacgaaga     240
gaggagtacg atgttttgga caagagacgt ggccgggacc ctgagatggg gggaaagccg     300
agaaggaaga accctcagga aggcctgtac aatgaactgc agaaagataa gatggcggag     360
gcctacagtg agattgggat gaaaggcgag cgccggaggg gcaaggggca cgatggcctt     420
taccagggtc tcagtacagc caccaaggac acctacgacg cccttcacat gcaggccctg     480
cccccctcgct aa                                                        492
```

<210> SEQ ID NO 91
<211> LENGTH: 163
<212> TYPE: PRT
<213> ORGANISM: Homo sapiens

<400> SEQUENCE: 91

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Ala Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg
```

<210> SEQ ID NO 92
<211> LENGTH: 492
<212> TYPE: DNA
<213> ORGANISM: Homo sapiens

<400> SEQUENCE: 92

```
atgaagtgga aggcgctttt caccgcggcc atcctgcagg cacagtggcc gattacagag      60
gcacagagct ttggcctgct ggatcccaaa ctctgctacc tgctggatgg aatcctcttc     120
atctatggtg tcattctcac tgccttgttc ctgagagtga agttcagcag agcgcagac      180
gcccccgcgt tccagcaggg ccagaaccag ctctataacg agctcaatct aggacgaaga     240
gaggagtacg atgttttgga caagagacgt ggccgggacc ctgagatggg gggaaagccg     300
agaaggaaga accctcagga aggcctgtac aatgaactgc agaaagataa gatggcggag     360
```

```
gcctacagtg agattgggat gaaaggcgag cgccggaggg gcaaggggca cgatggcctt      420
taccagggtc tcagtacagc caccaaggac acctacgacg cccttcacat gcaggccctg      480 cccctcgct aa                                                            492
```

<210> SEQ ID NO 93
<211> LENGTH: 163
<212> TYPE: PRT
<213> ORGANISM: Homo sapiens

<400> SEQUENCE: 93

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Phe Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg
```

<210> SEQ ID NO 94
<211> LENGTH: 492
<212> TYPE: DNA
<213> ORGANISM: Homo sapiens

<400> SEQUENCE: 94

```
atgaagtgga aggcgctttt caccgcggcc atcctgcagg cacagttgcc gattacagag       60
gcacagagct ttggcctgct ggatcccaaa ctctgctacc tgctggatgg aatcctcttc      120
atctatggtg tcattctcac tgccttgttc ctgagagtga agttcagcag gagcgcagac      180
gcccccgcgt tccagcaggg ccagaaccag ctctataacg agctcaatct aggacgaaga      240
gaggagtacg atgttttgga caagagacgt ggccgggacc ctgagatggg gggaaagccg      300
agaaggaaga accctcagga aggcctgtac aatgaactgc agaaagataa gatggcggag      360
gccttcagtg agattgggat gaaaggcgag cgccggaggg gcaaggggca cgatggcctt      420
taccagggtc tcagtacagc caccaaggac acctacgacg cccttcacat gcaggccctg      480 cccctcgct aa                                                            492
```

<210> SEQ ID NO 95
<211> LENGTH: 163
<212> TYPE: PRT
<213> ORGANISM: Homo sapiens

<400> SEQUENCE: 95

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Phe Asp Val Leu Asp Lys Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Phe Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg

<210> SEQ ID NO 96
<211> LENGTH: 465
<212> TYPE: DNA
<213> ORGANISM: Homo sapiens

<400> SEQUENCE: 96
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtg tcattctcac tgccttgttc ctgagagtga agttcagcag gagcgcagac     180
gccccccgcgt tccagcaggg ccagaaccag ctctataacg agctcaatct aggacgaaga     240
gaggagtacg atgttttgga cagagacgt ggccgggacc ctgagatggg gggaaagccg      300
agaaggaaga accctcagga aggcctgtac aatgaactgc agaaagataa gatggcggag     360
gccttcagtg agattgggat gaaaggcgag cgccggaggg gcaaggggca cgatggcctt     420
taccagggtc tcagtacagc caccaaggac accttcgacg cccct                    465

<210> SEQ ID NO 97
<211> LENGTH: 155
<212> TYPE: PRT
<213> ORGANISM: Homo sapiens

<400> SEQUENCE: 97

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg

```
                65                  70                  75                  80
Glu Glu Phe Asp Val Leu Asp Lys Arg Arg Gly Arg Asp Pro Glu Met
                        85                  90                  95

Gly Gly Lys Pro Arg Arg Lys Asn Pro Gln Glu Gly Leu Tyr Asn Glu
                100                 105                 110

Leu Gln Lys Asp Lys Met Ala Glu Ala Phe Ser Glu Ile Gly Met Lys
                115                 120                 125

Gly Glu Arg Arg Gly Lys Gly His Asp Gly Leu Tyr Gln Gly Leu
        130                 135                 140

Ser Thr Ala Thr Lys Asp Thr Phe Asp Ala Leu
145                 150                 155

<210> SEQ ID NO 98
<211> LENGTH: 363
<212> TYPE: DNA
<213> ORGANISM: Homo sapiens

<400> SEQUENCE: 98
atgaagtgga aggcgctttt caccgcggcc atcctgcagg cacagttgcc gattacagag    60
gcacagagct ttggcctgct ggatcccaaa ctctgctacc tgctggatgg aatcctcttc   120
atctatggtg tcattctcac tgccttgttc ctgagagtga agttcagcag gagcgcagac   180 gccccgcgt tccagcaggg ccagaaccag ctctataacg agctcaatct aggacgaaga   240
gaggagtacg atgttttgga caagagacgt ggccgggacc ctgagatggg gggaaagccg   300
agaaggaaga accctcagga aggcctgtac aatgaactgc agaaagataa gatggcggag   360
gcc                                                                  363

<210> SEQ ID NO 99
<211> LENGTH: 121
<212> TYPE: PRT
<213> ORGANISM: Homo sapiens

<400> SEQUENCE: 99

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Phe
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                        85                  90                  95

Gly Gly Lys Pro Arg Arg Lys Asn Pro Gln Glu Gly Leu Tyr Asn Glu
                100                 105                 110

Leu Gln Lys Asp Lys Met Ala Glu Ala
                115                 120

<210> SEQ ID NO 100
<211> LENGTH: 453
<212> TYPE: DNA
<213> ORGANISM: Homo sapiens

<400> SEQUENCE: 100
```

```
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtg tcattctcac tgccttgttc ctgagagtga agttcagcag gagcgcagac     180
gcccccgcgt accagcaggg ccagaaccag ctctataacg agctcaatct aggacgaaga     240
gaggagtacc atgttttgga caagagacgt ggccgggacc ctgagatggg gggaaagccg     300
agaaggaaga accctcagga aggcctgtac aatgaactgc agaaagataa gatggcggag     360
gccttcagtg agattgggat gaaggagcg cgccggaggg gcaaggggca cgatggcctt     420
taccagggtc tcagtacagc caccaaggac acc                                 453
```

<210> SEQ ID NO 101
<211> LENGTH: 151
<212> TYPE: PRT
<213> ORGANISM: Homo sapiens

<400> SEQUENCE: 101

```
Met Lys Trp Lys Ala Leu Phe Thr Ala Ala Ile Leu Gln Ala Gln Leu
  1               5                  10                  15

Pro Ile Thr Glu Ala Gln Ser Phe Gly Leu Leu Asp Pro Lys Leu Cys
             20                  25                  30

Tyr Leu Leu Asp Gly Ile Leu Phe Ile Tyr Gly Val Ile Leu Thr Ala
         35                  40                  45

Leu Phe Leu Arg Val Lys Phe Ser Arg Ser Ala Asp Ala Pro Ala Tyr
     50                  55                  60

Gln Gln Gly Gln Asn Gln Leu Tyr Asn Glu Leu Asn Leu Gly Arg Arg
 65                  70                  75                  80

Glu Glu Tyr Asp Val Leu Asp Lys Arg Arg Gly Arg Asp Pro Glu Met
                 85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Phe Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr
145                 150
```

METHOD OF PRODUCING T CELL RECEPTOR-DEFICIENT T CELLS EXPRESSING A CHIMERIC RECEPTOR

CROSS-REFERENCE TO RELATED APPLICATIONS

This application is a Continuation-in-part Application of U.S. patent application Ser. No. 13/502,978, filed Apr. 19, 2012, which is a national stage application of International Patent Application No. PCT/US2010/54846, filed on Oct. 29, 2010, which claims the benefit of priority to U.S. provisional patent application No. 61/255,980, filed Oct. 29, 2009, the disclosures of which are herein incorporated by reference in their entireties.

This invention was made with government support under contract number CA 130911 awarded by the National Institutes of Health. The government has certain rights in the invention.

SEQUENCE LISTING

The sequence listing in the filed named "76840o000104v2" having a size of 67,800 bytes that was created Aug. 13, 2012 is hereby incorporated by reference in its entirety.

BACKGROUND OF THE INVENTION

1. Field of the Invention

The invention is directed to TCR-deficient T cells, methods of making and using TCR-deficient T cells, and methods of using these TCR-deficient T cells to address diseases and disorders. In one embodiment, the invention broadly relates to TCR-deficient T cells, isolated populations thereof, and compositions comprising the same. In another embodiment of the invention, said TCR-deficient T cells are further designed to express a functional non-TCR receptor. The invention also pertains to methods of making said TCR-deficient T cells, and methods of reducing or ameliorating, or preventing or treating, diseases and disorders using said TCR-deficient T cells, populations thereof, or compositions comprising the same.

2. Description of Related Art

The global burden of cancer doubled between 1975 and 2000, and cancer is expected to become the leading cause of death worldwide by 2010. According to the American Cancer Society, it is projected to double again by 2020 and to triple by 2030. Thus, there is a need for more effective therapies to treat various forms of cancer. Ideally, any cancer therapy should be effective (at killing cancerous cells), targeted (i.e. selective, to avoid killing healthy cells), permanent (to avoid relapse and metastasis), and affordable. Today's standards of care for most cancers fall short in some or all of these criteria.

Cellular immunotherapy has been shown to result in specific tumor elimination and has the potential to provide specific and effective cancer therapy (Ho, W. Y. et al. 2003. *Cancer Cell* 3:1318-1328; Morris, E. C. et al. 2003. *Clin. Exp. Immunol.* 131:1-7; Rosenberg, S. A. 2001. *Nature* 411:380-384; Boon, T. and P. van der Bruggen. 1996. *J. Exp. Med.* 183:725-729). T cells have often been the effector cells of choice for cancer immunotherapy due to their selective recognition and powerful effector mechanisms. T cells recognize specific peptides derived from internal cellular proteins in the context of self-major histocompatability complex (MHC) using their T cell receptors (TCR).

It is recognized in the art that the TCR complex associates in precise fashion by the formation of dimers and association of these dimers (TCR-alpha/beta, CD3-gamma/epsilon, CD3-delta/epsilon, and CD3-zeta dimer) into one TCR complex that can be exported to the cell surface. The inability of any of these complexes to form properly will inhibit TCR assembly and expression (Call, M. E. et al., (2007) Nature Rev. Immunol., 7:841-850; Call, M. E. et al., (2005) Annu. Rev. Immunol., 23:101-125).

Particular amino acid residues in the respective TCR chains have been identified as important for proper dimer formation and TCR assembly. In particular, for TCR-alpha, these key amino acids in the transmembrane portion are arginine (for association with CD3-zeta) and lysine (for association with the CD3-epsilon/delta dimer). For TCR-beta, the key amino acid in the transmembrane portion is a lysine (for association with CD3-epsilon/gamma dimer). For CD3-gamma, the key amino acid in the transmembrane portion is a glutamic acid. For CD3-delta, the key amino acid in the transmembrane portion is an aspartic acid. For CD3-epsilon, the key amino acid in the transmembrane portion is an aspartic acid. For CD3-zeta, the key amino acid in the transmembrane portion is an aspartic acid (Call, M. E. et al., (2007) Nature Rev. Immunol., 7:841-850; Call, M. E. et al., (2005) Annu. Rev. Immunol., 23:101-125).

Peptides derived from altered or mutated proteins in tumors can be recognized by specific TCRs. Several key studies have led to the identification of antigens associated with specific tumors that have been able to induce effective cytotoxic T lymphocyte (CTL) responses in patients (Ribas, A. et al. 2003. *J. Clin. Oncol.* 21:2415-2432). T cell effector mechanisms include the ability to kill tumor cells directly and the production of cytokines that activate other host immune cells and change the local tumor microenvironment. Theoretically, T cells could identify and destroy a tumor cell expressing a single mutated peptide. Adoptive immunotherapy with CTL clones specific for MARTI or gp100 with low dose IL-2 has been effective in reduction or stabilization of tumor burden in some patients (Yee, C. et al. 2002. *Proc. Natl. Acad. Sci. USA* 99:16168-16173). Other approaches use T cells with a defined anti-tumor receptor. These approaches include genetically modifying CTLs with new antigen-specific T cell receptors that recognize tumor peptides and MHC, chimeric antigen receptors (CARS) derived from single chain antibody fragments (scFv) coupled to an appropriate signaling element, or the use of chimeric NK cell receptors (Ho, W. Y. et al. 2003. Cancer Cell 3:431-437; Eshhar, Z. et al. 1993. Proc. Natl. Acad. Sci. USA 90:720-724; Maher, J. and E. T. Davies. 2004. Br. J. Cancer 91:817-821; Zhang, T. et al. 2005. *Blood* 106:1544-1551).

Cell-based therapies are used in patients who have failed conventional chemotherapy or radiation treatments, or have relapsed, often having attempted more than one type of therapy. The immune cells from patients with advanced cancer, who may have gone through rounds of chemotherapy, do not respond as robustly as healthy individuals. Moreover, cancer patients are often elderly and may suffer from other diseases that may limit the potential of their immune cells to become primed effector cells, even after in vitro activation and expansion. In addition, each cancer patient must provide a sufficient number of their own immune cells in order for them to be engineered to express a new immune receptor. Because each therapy must be custom made for the patient, this process requires weeks from the time the decision to undertake such therapy is made; meanwhile, the cancer continues to grow. U.S. patent application publication no. US 2002/0039576 discloses a method for modulating T cell activity, where the T cells used have a phenotype of CD3+-αβ-TcR+CD4−CD8−CD28−NK1.1−. U.S. patent application publication no. US 2006/0166314 discloses use of mutated T cells to treat cancer where the T cells are ones with a T cell response-mediating MDM2 protein-specific αβ-T cell receptor.

Cancer is not the only disease wherein T cell manipulation could be effective therapy. It is known that active T cell receptors on T cells are critical to the response of the body to stimulate immune system activity. For example, it has been shown that T cell receptor diversity plays a role in graft-versus-host-disease (GVHD), in particular chronic GVHD (Anderson et al. (2004) *Blood* 104:1565-1573). In fact, administration of T cell receptor antibodies has been shown to reduce the symptoms of acute GVHD (Maeda et al. (2005) *Blood* 106:749-755).

There remains a need for more effective T cell-based therapies for the treatment of certain diseases and disorders, and methods of treatment based on the design of new types of T cells.

BRIEF SUMMARY OF THE INVENTION

In one embodiment, this invention broadly relates to isolated, modified T cells that do not express a functional T cell receptor (TCR). In this embodiment, the T cells are TCR-deficient in the expression of a functional TCR. In another embodiment of the invention, TCR-deficient T cells are engineered to express a functional non-TCR receptor, such as, for example, a chimeric receptor. These cells also function as a platform to allow the expression of other targeting receptors, e.g., receptors that may be useful in specific diseases, while retaining the effector functions of T cells, albeit without a functioning TCR.

The invention contemplates populations of TCR-deficient T cells, and compositions comprising the same. The invention also contemplates methods of making said TCR-deficient T cells, and methods of reducing or ameliorating, or preventing or treating, diseases and disorders using said TCR-deficient T cells, populations thereof, or therapeutic compositions comprising the same. In one embodiment, this composition can be used to treat cancer, infection, one or more autoimmune disorders, radiation sickness, or to prevent or treat graft versus host disease (GVHD) or transplantation rejection in a subject undergoing transplant surgery.

DETAILED DESCRIPTION OF PREFERRED EMBODIMENTS

Definitions

Figure 1:
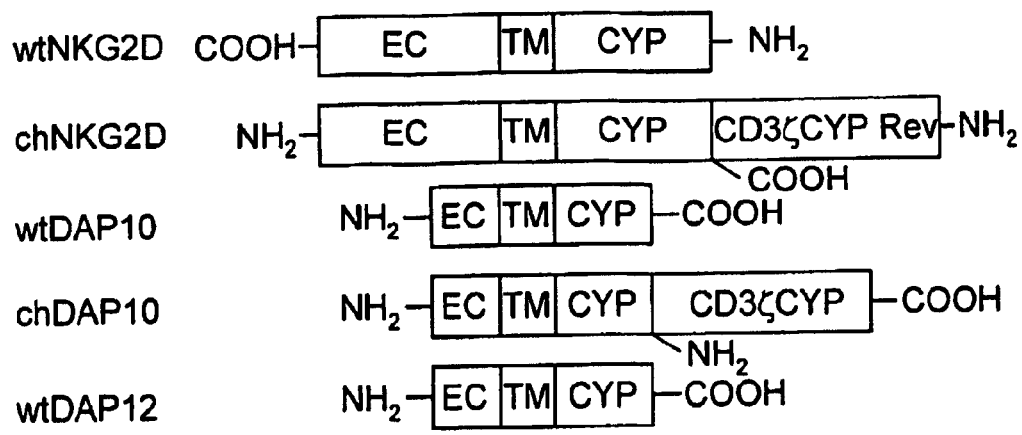
FIG. 1 illustrates chimeric NK receptors described herein. Extracellular (EC), transmembrane (TM), and cytoplasmic (Cyp) portions are indicated. Wild-type (WT) and chimeric (CH) forms of the receptors are indicated, wherein $NH_2$ denotes the N-terminus and COOH denotes the C-terminus.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

In the context of the present invention, by a "TCR-deficient T cell", or a similar phrase is intended an isolated T cell(s) that lacks expression of a functional TCR, is internally capable of inhibiting its own TCR production, and further wherein progeny of said T cell(s) may also be reasonably expected to be internally capable of inhibiting their own TCR production. Internal capability is important in the context of therapy where TCR turnover timescales (~hours) are much faster than demonstrable efficacy timescales (days-months), i.e., internal capability is required to maintain the desired phenotype during the therapeutic period. This may e.g., be accomplished by different means as described infra, e.g., by engineering a T cell such that it does not express any functional TCR on its cell surface, or by engineering the T cell such that it does not express one or more of the subunits that comprise a functional TCR and therefore does not produce a functional TCR or by engineering a T cell such that it produces very little functional TCR on its surface, or which expresses a substantially impaired TCR, e.g by engineering the T cell to express mutated or truncated forms of one or more of the subunits that comprise the TCR, thereby rendering the T cell incapable of expressing a functional TCR or resulting in a cell that expresses a substantially impaired TCR. The different subunits that comprise a functional TCR are described infra. Whether a cell expresses a functional TCR may be determined using known assay methods such as are known in the art described herein. By a "substantially impaired TCR" applicants mean that this TCR will not substantially elicit an adverse immune reaction in a host, e.g., a GVHD reaction.

As described in detail infra, optionally these TCR-deficient cells may be engineered to comprise other mutations or transgenes that e.g., mutations or transgenes that affect T cell growth or proliferation, result in expression or absence of expression of a desired gene or gene construct, e.g., another receptor or a cytokine or other immunomodulatory or therapeutic polypeptide or a selectable marker such as a dominant selectable marker gene, e.g., DHFR or neomycin transferase.

"Allogeneic T cell" refers to a T cell from a donor having a tissue HLA type that matches the recipient. Typically, matching is performed on the basis of variability at three or more loci of the HLA gene, and a perfect match at these loci is preferred. In some instances allogeneic transplant donors may be related (usually a closely HLA matched sibling), syngeneic (a monozygotic 'identical' twin of the patient) or unrelated (donor who is not related and found to have very close degree of HLA matching). The HLA genes fall in two categories (Type I and Type II). In general, mismatches of the Type-I genes (i.e. HLA-A, HLA-B, or HLA-C) increase the risk of graft rejection. A mismatch of an HLA Type II gene (i.e. HLA-DR, or HLA-DQB1) increases the risk of graft-versus-host disease.

In the context of the present invention, a "bank of tissue matched TCR-deficient T cells" refers to different compositions each containing T cells of a specific HLA allotype which are rendered TCR-deficient according to the invention. Ideally this bank will comprise compositions containing T cells of a wide range of different HLA types that are representative of the human population. Such a bank of engineered TCR-deficient T cells will be useful as it will facilitate the availability of T cells suitable for use in different recipients such as, e.g., cancer patients. The invention provides methods of producing a bank of TCR-deficient T cells having different HLA haplotypes. The methods comprise obtaining a pool of isolated T cells having a defined HLA haplotype, which is determined by standard typing procedures (e.g., antibodies, PCR, or DNA sequencing), and expressing a TCR Inhibitory Molecule (TIM) in these T cells that destabilizes the TCR complex by reducing or blocking expression of components of the TCR complex. This is done for T cells obtained from a variety of different individuals with different HLA haplotypes. This collection of different donor T cells that express TIMs comprise the TCR-deficient T cell bank. The T cell bank comprises different T cell pools that each contain TCR-deficient T cells of a specific HLA type. Preferably, the T cell bank comprises a variety of different HLA types, e.g., at least 10 different HLA tissue types, at least 50 different HLA tissue types, at least 100 different HLA tissue types. In one embodiment, the T cell bank comprises T cells of at least 10 different HLA tissue types. In another embodiment, the T cell bank comprises T cells of at least 100 different HLA tissue types.

In the context of the present invention, a "therapeutically effective amount" is identified by one of skill in the art as being an amount of TCR-deficient T cells that, when administered to a patient, alleviates the signs and or symptoms of the disease (e.g., cancer, infection or GVHD). The actual amount to be administered can be determined based on studies done either in vitro or in vivo where the functional TCR-deficient T cells exhibit pharmacological activity against disease. For example, the functional TCR-deficient T cells may inhibit tumor cell growth either in vitro or in vivo and the amount of functional TCR-deficient T cells that inhibits such growth is identified as a therapeutically effective amount.

A "pharmaceutical composition" refers to a chemical or biological composition suitable for administration to a mammal. Such compositions may be specifically formulated for administration via one or more of a number of routes, including but not limited to buccal, intraarterial, intracardial, intracerebroventricular, intradermal, intramuscular, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, liquid, gel, drops, or other means of administration.

As used herein, a nucleic acid construct or nucleic acid sequence is intended to mean a DNA molecule which can be transformed or introduced into a T cell and be transcribed and translated to produce a product (e.g., a chimeric receptor or a suicide protein).

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

The invention contemplates compositions and methods for reducing or ameliorating, or preventing or treating, diseases or conditions such as cancer, infectious disease, GVHD, transplantation rejection, one or more autoimmune disorders, or radiation sickness. In a non-limiting embodiment, the compositions are based on the concept of providing an allogeneic source of isolated human T cells, namely TCR-deficient T cells, that can be manufactured in advance of patient need and inexpensively. The ability to create a single therapeutic product at a single site using processes that are well controlled is attractive in terms of both cost and quality considerations. The change from an autologous to an allogeneic source for T cells offers significant advantages. For example, it has been estimated that a single healthy donor could supply T cells sufficient to treat dozens of patients after transduction and expansion.

According to the present invention, modified allogeneic T cells are produced that do not express functional T cell receptors (TCRs). It is to be understood that some, or even all, of the TCR subunits/dimers may be expressed on the cell surface, but that the T cell does not express enough functional TCR to induce an undesirable reaction in the host. Without functional TCRs on their surface, the allogeneic T cells fail to mount an undesired immune response to host cells. As a result, these TCR-deficient T cells fail to cause GVHD, for example, as they cannot recognize the host MHC molecules. Additionally, these TCR-deficient T cells can be engineered to simultaneously express functional, non-TCR, disease-specific receptors.

As is well known to one of skill in the art, various methods are readily available for isolating allogeneic T cells from a subject. For example, using cell surface marker expression or using commercially available kits (e.g., ISOCELL™ from Pierce, Rockford, Ill.).

For cancer therapy, the approach encompasses producing an isolated pool of TCR-deficient T effector cells, e.g., of a desired tissue allotype that do not express a functional form of their endogenous TCR or which express substantially reduced levels of endogenous TCR compared to wild type T cells such that they do not elicit an immune response upon administration (such as GVHD), but instead express a functional, non-TCR receptor that recognizes tumor cells, or express another polypeptide that does not appreciably, or at all, attack non-disease associated cells, e.g., normal (non-tumorigenic) cells that do not express the antigen or ligand recognized by the tumor specific receptor or which express said antigen or ligand at reduced levels relative to tumor cells. It is understood by those skilled in the art that certain tumor-associated antigens are expressed in non-cancerous tissues, but they are viable therapeutic targets in a tumor-bearing host. With respect thereto it is generally understood by those skilled in the art that certain non-TCR, tumor-specific receptors are expressed in non-cancerous tissues, but are viable therapeutic targets in a tumor-bearing host as they may be expressed at significantly reduced levels in normal than tumor cells.

While not necessary for most therapeutic usages of the subject TCR-deficient T cells, in some instances it may be desirable to remove some or all of the donor T cells from the host shortly after they have mediated their anti-tumor effect. This may be facilitated by engineering the T cells to express additional receptors or markers that facilitate their removal and/or identification in the host such as GFP and the like. While the present invention should substantially eliminate any possibility of GVHD or other adverse immune reaction in the recipient this may be desired in some individuals. This should not compromise efficacy as it has already been shown that donor T cells do not need to remain long in the host for a long-term anti-tumor effect to be initiated (Zhang, T., et al. 2007. Cancer Res. 67:11029-11036; Barber, A. et al. 2008. *J. Immunol.* 180:72-78).

In one embodiment of the invention, nucleic acid constructs introduced into engineered T cells further contains a suicide gene such as thymidine kinase (TK) of the HSV virus (herpesvirus) type I (Bonini, et al. (1997) Science 276:1719-1724), a Fas-based "artificial suicide gene" (Thomis, et al. (2001) Blood 97:1249-1257), or *E. coli* cytosine deaminase gene which are activated by gancyclovir, AP1903, or 5-fluorocytosine, respectively. The suicide gene is advantageously included in the nucleic acid construct of the present invention to provide for the opportunity to ablate the transduced T cells in case of toxicity and to destroy the chimeric construct once a tumor has been reduced or eliminated. The use of suicide genes for eliminating transformed or transduced cells is well-known in the art. For example, Bonini, et al. ((1997) Science 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) J. Gene Med. 6:704-711) describe the targeting of neuroblastoma with cytotoxic T lymphocyte clones genetically modified to express a chimeric scFvFc:zeta immunoreceptor specific for an epitope on L1-CAM, wherein the construct further expresses the hygromycin thymidine kinase (HyTK) suicide gene to eliminate the transgenic clones.

It is contemplated that the suicide gene can be expressed from the same promoter as the shRNA, minigene, or non-TCR receptor, or from a different promoter. Generally, however, nucleic acid sequences encoding the suicide protein and shRNA, minigene, or non-TCR receptor reside on the same construct or vector. Expression of the suicide gene from the same promoter as the shRNA, minigene, or non-TCR receptor can be accomplished using any well-known internal ribosome entry site (IRES). Suitable IRES sequences which can be used in the nucleic acid construct of the present invention include, but are not limited to, IRES from EMCV, c-myc, FGF-2, poliovirus and HTLV-1. By way of illustration only, a nucleic acid construct for expressing a chimeric receptor can have the following structure: promoter->chimeric receptor->IRES->suicidal gene. Alternatively, the suicide gene can be expressed from a different promoter than that of the chimeric receptor (e.g., promoter 1->chimeric receptor->promoter 2->suicidal gene).

Because of the broad application of T cells for cell therapies, and the improved nature of the T cells of the invention, the present invention encompasses any method or composition wherein T cells are therapeutically desirable. Such compositions and methods include those for reducing or ameliorating, or preventing or treating cancer, GVHD, transplantation rejection, infection, one or more autoimmune disorders, radiation sickness, or other diseases or conditions that are based on the use of T cells derived from an allogeneic source that lack expression of functional TCR.

As indicated, further embodiments of the invention embrace recombinant expression of receptors in said TCR-deficient T cells, such as chimeric NKG2D, chimeric Fv domains, NKG2D, or any other receptor to initiate signals to T cells, thereby creating potent, specific effector T cells. One of skill in the art can select the appropriate receptor to be expressed by the TCR-deficient T cell based on the disease to be treated. For example, receptors that can be expressed by the TCR-deficient T cell for treatment of cancer would include any receptor to a ligand that has been identified on cancer cells. Such receptors include, but are not limited to, NKG2D, NKG2A, NKG2C, NKG2F, LLT1, AICL, CD26, NKRP1, NKp30, NKp44, NKp46, CD244 (2B4), DNAM-1, and NKp80.

In another embodiment of the invention, such receptors include, but not limited to, chimeric receptors comprising a ligand binding domain obtained from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody such as anti-Her2neu or anti-EGFR, and a signaling domain obtained from CD3-zeta, Dap10, CD28, 41BB, and CD40L. An exemplary chimeric receptor is chNKG2D, in which the NKG2D is linked to the cytoplasmic domain of CD3zeta, and associates with Dap10 to provide both primary and secondary activation signals to T cells (Zhang, T. et al. 2006. *Cancer Res.* 66(11): 5927-5933). In one embodiment of the invention, the chimeric receptor binds MIC-A, MIC-B, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, RON, or one or more members of the ULBP/RAET1 family including ULBP1, ULBP2, ULBP3, ULBP4, ULBP5, and ULBP6.

In the methods of the present invention a patient suffering from cancer, GVHD, transplantation rejection, infection, one or more autoimmune disorders, or radiation sickness is administered a therapeutically effective amount of a composition comprising said TCR-deficient T cells. In another embodiment of the invention, a therapeutically effective amount of a composition comprising said TCR-deficient T cells is administered to prevent, treat, or reduce GVHD, transplantation rejection, or cancer.

Methods of Producing TCR-Deficient T-Cells

T cells stably lacking expression of a functional TCR according to the invention may be produced using a variety of approaches. T cells internalize, sort, and degrade the entire T cell receptor as a complex, with a half-life of about 10 hours in resting T cells and 3 hours in stimulated T cells (von Essen, M. et al. 2004. *J. Immunol.* 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

The methods of the present invention include expression of TCR-inhibitory Molecules (TIMs) in T cells to destabilize the TCR complex by blocking expression of essential components of the TCR complex and/or interrupting TCR expression or function. There are various classes of TIMs, including, but not limited to, small-hairpin RNAs (shRNAs) and dominant negative inhibitor proteins, e.g., truncated proteins that lack important signaling motifs; KIR-fusion proteins that promote inhibitory signals; and proteins with mutations that disrupt proper association with other TCR components and/or proper signaling. Generally, TIMs can be used to generate TCR-deficient T cells by preventing expression of any or very little functional TCR on the cell surface, and/or promote expression of a substantially impaired TCR on the cell surface.

As shown by the results in the experimental examples infra, the present inventor has demonstrated that TCR expression or function may be interrupted or eliminated using TIMs, e.g., shRNAs and/or dominant-negative inhibitors, thus producing TCR-deficient T cells. Such TCR-deficient cell lines are well-suited for use in T cell-based therapies for the treatment of cancer and other diseases and disorders, as described below.

In one embodiment of the invention, TCR expression is eliminated using small-hairpin RNAs (shRNAs) that target nucleic acids encoding specific TCRs (e.g., TCR-α and TCR-β) and/or CD3 chains (e.g., CD3 zeta) in primary T cells. By blocking expression of one or more of these proteins, the T cell will no longer produce one or more of the key components of the TCR complex, thereby destabilizing the TCR complex and preventing cell surface expression of a functional TCR. Even though some TCR complexes can be recycled to the cell surface, the shRNA will prevent new production of TCR proteins resulting in degradation and removal of the entire TCR complex, resulting in the production of a T cell having a stable deficiency in functional TCR expression.

Expression of shRNAs in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the shRNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3.

In a non-limiting embodiment of the invention, exemplary targeting shRNAs have been designed for key components of the TCR complex as set forth below (Table 1).

TABLE 1

| Target | Target base | shRNA Sequence | GC % | SEQ ID NO: |
|---|---|---|---|---|
| TCR-β | 18[a] | AGTGCGAGGAGATTCGGCAGCTTAT | 52 | 1 |
| | 21[a] | GCGAGGAGATTCGGCAGCTTATTTC | 52 | 2 |
| | 48[a] | CCACCATCCTCTATGAGATCTTGCT | 48 | 3 |
| | 54[a] | TCCTCTATGAGATCTTGCTAGGGAA | 44 | 4 |
| TCR-α | 3[b] | TCTATGGCTTCAACTGGCTAGGGTG | 52 | 5 |
| | 76[b] | CAGGTAGAGGCCTTGTCCACCTAAT | 52 | 6 |
| | 01[b] | GCAGCAGACACTGCTTCTTACTTCT | 48 | 7 |
| | 07[b] | GACACTGCTTCTTACTTCTGTGCTA | 44 | 8 |
| CD3-ε | 89[c] | CCTCTGCCTCTTATCAGTTGGCGTT | 52 | 9 |
| | 27[c] | GAGCAAAGTGGTTATTATGTCTGCT | 40 | 10 |
| | 62[c] | AAGCAAACCAGAAGATGCGAACTTT | 40 | 11 |
| | 45 | GACCTGTATTCTGGCCTGAATCAGA | 48 | 12 |
| | | GGCCTCTGCCTCTTATCAGTT | 52 | 13 |
| | | GCCTCTGCCTCTTATCAGTTG | 52 | 14 |
| | | GCCTCTTATCAGTTGGCGTTT | 48 | 15 |
| | | AGGATCACCTGTCACTGAAGG | 52 | 16 |
| | | GGATCACCTGTCACTGAAGGA | 52 | 17 |
| | | GAATTGGAGCAAAGTGGTTAT | 38 | 18 |
| | | GGAGCAAAGTGGTTATTATGT | 38 | 19 |
| | | GCAAACCAGAAGATGCGAACT | 48 | 20 |
| | | ACCTGTATTCTGGCCTGAATC | 48 | 21 |
| | | GCCTGAATCAGAGACGCATCT | 52 | 22 |
| | | CTGAAATACTATGGCAACACAATGATAAA | 31 | 23 |
| | | AAACATAGGCAGTGATGAGGATCACCTGT | 45 | 24 |
| | | ATTGTCATAGTGGACATCTGCATCACTGG | 45 | 25 |
| | | CTGTATTCTGGCCTGAATCAGAGACGCAT | 48 | 26 |
| CD3-δ [d] | | GATACCTATAGAGGAACTTGA | 38 | 27 |
| | | GACAGAGTGTTTGTGAATTGC | 43 | 28 |
| | | GAACACTGCTCTCAGACATTA | 43 | 29 |
| | | GGACCCACGAGGAATATATAG | 48 | 30 |
| | | GGTGTAATGGGACAGATATAT | 38 | 31 |
| | | GCAAGTTCATTATCGAATGTG | 38 | 32 |
| | | GGCTGGCATCATTGTCACTGA | 52 | 33 |
| | | GCTGGCATCATTGTCACTGAT | 48 | 34 |
| | | GCATCATTGTCACTGATGTCA | 43 | 35 |
| | | GCTTTGGGAGTCTTTCTGCTTT | 48 | 36 |
| | | TGGAACATAGCACGTTTCTCTCTGGCCTG | 52 | 37 |
| | | CTGCTCTCAGACATTACAAGACTGGACCT | 48 | 38 |
| | | ACCGTGGCTGGCATCATTGTCACTGATGT | 52 | 39 |
| | | TGATGCTCAGTACAGCCACCTTGGAGGAA | 52 | 40 |

TABLE 1-continued

| Target | Target base | shRNA Sequence | GC % | SEQ ID NO: |
|---|---|---|---|---|
| CD3-γ[e] | | GGCTATCATTCTTCTTCAAGG | 43 | 41 |
| | | GCCCAGTCAATCAAAGGAAAC | 48 | 42 |
| | | GGTTAAGGTGTATGACTATCA | 38 | 43 |
| | | GGTTCGGTACTTCTGACTTGT | 48 | 44 |
| | | GAATGTGTCAGAACTGCATTG | 43 | 45 |
| | | GCAGCCACCATATCTGGCTTT | 52 | 46 |
| | | GGCTTTCTCTTTGCTGAAATC | 43 | 47 |
| | | GCTTTCTCTTTGCTGAAATCG | 43 | 48 |
| | | GCCACCTTCAAGGAAACCAGT | 52 | 49 |
| | | GAAACCAGTTGAGGAGGAATT | 43 | 50 |
| | | GGCTTTCTCTTTGCTGAAATCGTCAGCAT | 45 | 51 |
| | | AGGATGGAGTTCGCCAGTCGAGAGCTTCA | 55 | 52 |
| | | CCTCAAGGATCGAGAAGATGACCAGTACA | 48 | 53 |
| | | TACAGCCACCTTCAAGGAAACCAGTTGAG | 48 | 54 |
| CD3-ζ [f.] | | TGCTGTTGACAGTGAGCGACCTCTTGCCAGG ATATTTATTTTAGTGAAGCCACAGATGTAAAT AAATATCCTGGCAAGAGGGTGCCTACTGCCT CGGA | | 68 |
| | | TGCTGTTGACAGTGAGCGACCCTCTTGCCAG GATATTTTATTAGTGAAGCCACAGATGTAATA AATATCCTGGCAAGAGGGCTGCCTACTGCCT CGGA | | 69 |
| | | TGCTGTTGACAGTGAGCGACCTCAGTATCCTG GATCTGAATAGTGAAGCCACAGATGTATTCA GATCCAGGATACTGAGGGTGCCTACTGCCTC GGA | | 70 |
| | | TGCTGTTGACAGTGAGCGCGGATGGAATCCT CTTCATCTATAGTGAAGCCACAGATGTATAG ATGAAGAGGATTCCATCCATGCCTACTGCCTC GGA | | 71 |

[a]With reference to Accession No. EU030678.
[b]With reference to Accession No. AY247834.
[c]With reference to Accession No. NM_000733.
[d] With reference to Accession No. NM_000732.
[e]With reference to Accession No. NM_000073.
[f.] With reference to Accession No. NM_000734.

TCR-alpha, TCR-beta, TCR-gamma, TCR-delta, CD3-gamma, CD3-delta, CD3-epsilon, or CD3-zeta mRNAs can be targeted separately or together using a variety of targeting shRNAs. The TCR-β and TCR-α chains are composed of variable and constant portions. Several targeting shRNAs have been designed for the constant portions of these TCR/CD3 sequences. One or a combination of shRNAs can be used for each molecular target to identify the most efficient inhibitor of TCR expression. Using established protocols, each shRNA construct is cloned into, e.g., a pLko.1 plasmid or pSMc2 vector, with expression controlled by a promoter routinely used in the art, e.g., the U6p promoter. The resulting construct can be screened and confirmed for accuracy by sequencing. The shRNA expression plasmid can then be transfected into any suitable host cell (e.g., 293T), together with a packaging plasmid and an envelope plasmid for packaging. Primary human peripheral blood mononuclear cells (PBMCs) are isolated from healthy donors and activated with low dose soluble anti-CD3 and, e.g., 25 U/ml to 50 U/ml, rhuIL-2 for 72 hours. Although it is not required to activate T cells for retroviral transduction, transduction works more efficiently and allows the cells to continue to expand in IL-2. The activated cells are washed and transduced, e.g., using a 1 hour spin-fection at 30° C., followed by a 7 hour resting period.

In another embodiment of the invention, over-expression of a dominant-negative inhibitor protein is capable of interrupting TCR expression or function. In this embodiment of the invention, a minigene that incorporates part, or all, of a polynucleotide encoding for one of the TCR components (e.g., TCR-alpha, TCR-beta, CD3-gamma, CD3-delta, CD3-epsilon, or CD3-zeta) is prepared, but is modified so that: (1) it lacks key signaling motifs (e.g., an ITAM) required for protein function; (2) is modified so it does not associate properly with its other natural TCR components; or (3) can associate properly but does not bind ligands (e.g., a truncated TCR beta minigene). In addition, the minigene may be altered to include an inhibitory signal motif, e.g., a cytoplasmic domain from a MR protein, which alters cell signaling and promotes inhibitory signals through the recruitment of phosphatases, e.g., SHP1 and SHP2.

These minigenes may also encode a portion of a protein that serves as a means to identify the over-expressed minigene. For example, polynucleotides encoding a truncated CD19 protein, which contains the binding site for anti-CD19 mAbs, can be operably linked to the minigene so that the resulting cell that expresses the minigene will express the encoded protein and can be identified with anti-CD19 mAbs. This identification enables one to determine the extent of minigene expression and isolate cells expressing this protein (and thus lack a functional TCR).

In one embodiment of the invention, over-expression of a minigene lacking a signaling motif(s) leads to a TCR complex that cannot signal properly when the TCR is engaged by its MHC-peptide ligand on an opposing cell. In a non-limiting embodiment of the invention, high expression of this minigene (and the encoded polypeptide) outcompetes the natural complete protein when the TCR components associate, resulting in a TCR complex that cannot signal. In another embodiment of the invention, the minigene comprises, or alternatively consists of, a polynucleotide encoding full or partial CD3-zeta, CD3-gamma, CD3-delta, or CD3-epsilon polypeptides lacking the ITAM motifs required for signaling. The CD3-zeta protein contains three ITAM motifs in the cytoplasmic portion, and in one embodiment of the invention, removal of all of these through truncation inhibits proper TCR signaling in any complexes where this modified protein is incorporated. See, e.g., TIM5-8 in Table 2, which correspond to SEQ ID NOS:72-79. The construct may incorporate ITIM or other signaling motifs, which are known to alter cell signaling and promote inhibitory signals through the recruitment of phosphatases such as SHP1 and SHP2. See, e.g., TIM9-13 in Table 2, which correspond to SEQ ID NOS:80-89.

In one embodiment of the invention, the minigene comprises a polynucleotide encoding full or partial CD3-zeta, CD3-gamma, CD3-delta, or CD3-epsilon polypeptides with mutations, e.g., a single nucleotide alteration, that result in a change of the amino acid codified by the polynucleotide. See, e.g., TIM14-19 in Table 2, which correspond to SEQ ID NOS: 90-101.

In another embodiment of the invention, over-expression of a minigene is modified so that the encoded polypeptide can associate with some, but not all, of its natural partners, creating competition with the normal protein for those associating proteins. In another non-limiting hypothesis of the invention, high level expression of the minigene (and the encoded polypeptide) outcompetes the natural partner proteins and prevents assembly of a functional TCR complex, which requires all components to associate in the proper ratios and protein-protein interactions. In another embodiment of the invention, minigenes comprise, or alternatively consist of, all or part of the polynucleotides encoding full-length proteins (e.g., TCR-alpha, TCR-beta, CD3-gamma, CD3-delta, CD3-epsilon, or CD3-zeta), but containing selected deletions in the sequence coding for amino acids in the transmembrane portion of the protein that are known to be required for assembly with other TCR/CD3 proteins.

In a preferred embodiment of the invention, selected deletions in the sequence coding for amino acids in the transmembrane portion of the protein known to be required for assembly with other TCR/CD3 proteins include, but are not limited to: the arginine residue at position 5 in the TCR-alpha transmembrane region; the lysine residue at position 10 in the TCR-alpha transmembrane region; the lysine residue at position 9 in the TCR-beta transmembrane region; the glutamic acid residue in the transmembrane region of CD3-gamma; the aspartic acid residue in the transmembrane region of CD3-delta-epsilon; the aspartic acid residue in the transmembrane region of CD3-epsilon; and the aspartic acid residue in the transmembrane region of CD3-zeta.

Figure 2:
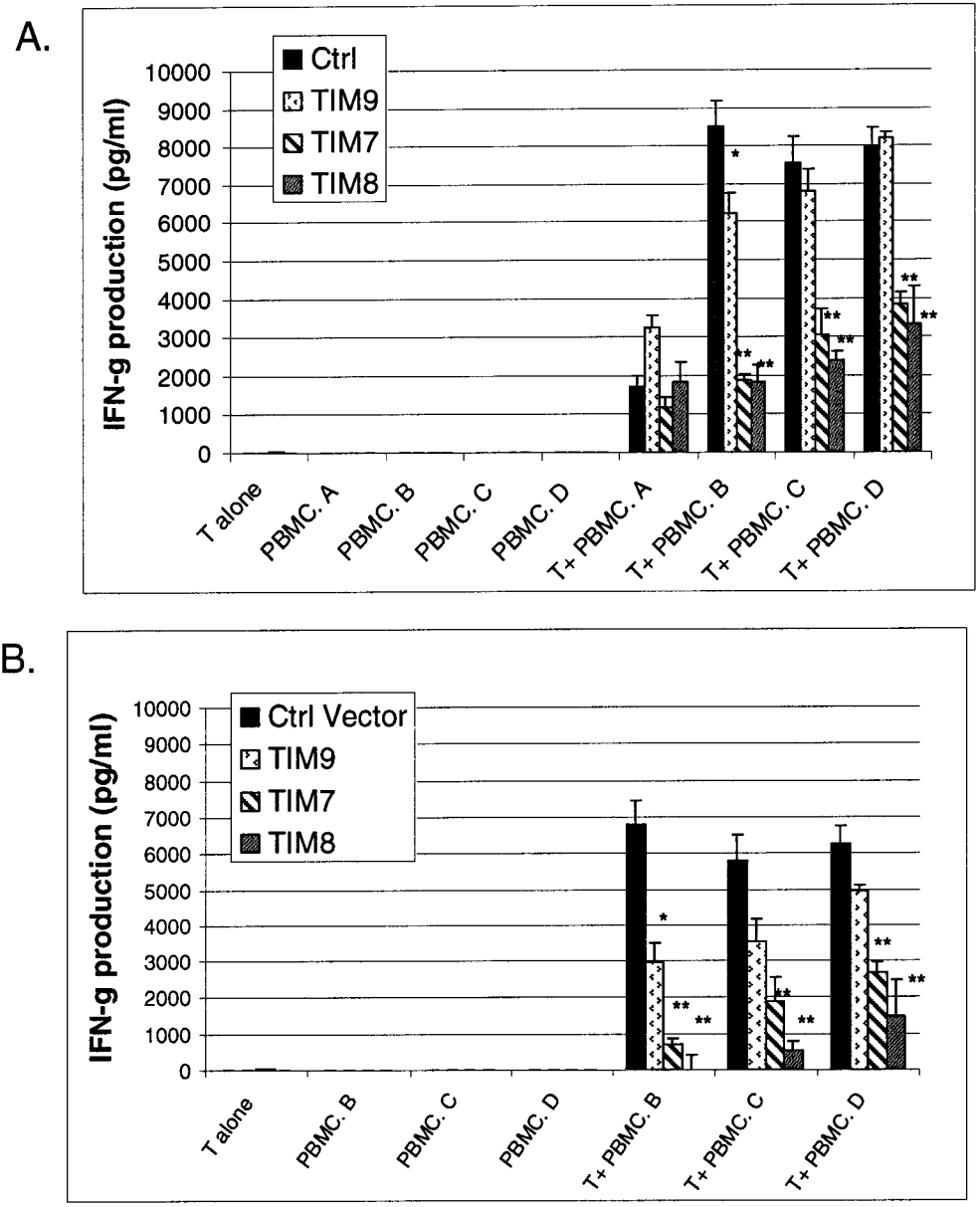
FIG. 2 illustrates that TIMs reduce TCR recognition and function in human T cells during culture with allogeneic PBMCs. Panel (A) shows that TIM-transduced T cells cultured with allogenic PMBCs have a reduction in IFN-γ production. Total IFN-γ production is shown. Panel (B) shows IFN-γ amounts after subtraction of the amount of autologous IFN-γ. This value represents the specific IFN-γ produced by recognition of the allogeneic PBMCs.

Over-expression of a truncated TCR-alpha, TCR-beta, TCR-gamma, or TCR-delta protein results in a TCR complex that cannot bind to MHC-peptide ligands, and thus will not function to activate the T cell. See, FIG. 2, panels (A) and (B). In another embodiment of the invention, minigenes comprise, or alternatively consist of, polynucleotides encoding the entire cytoplasmic and transmembrane portions of these proteins and portions of the extracellular region, but lacks polynucleotides encoding all or part of the first extracellular domain (i.e., the most outer domain containing the ligand binding site). In a preferred embodiment, said minigene polynucleotides do not encode Valpha and Vbeta polypeptides of the TCR-alpha and TCR-beta chains. In one embodiment, the minigene polynucleotides may be operably linked to polynucleotides encoding a protein epitope tag (e.g., CD19), thereby allowing mAb identification of cells expressing these genes.

In another embodiment, these minigenes can be expressed using a strong viral promoter, such as the 5'LTR of a retrovirus, or a CMV or SV40 promoter. Typically, this promoter is immediately upstream of the minigene and leads to a high expression of the minigene mRNA. In another embodiment, the construct encodes a second polynucleotide sequence under the same promoter (using for example an IRES DNA sequence between) or another promoter. This second polynucleotide sequence may encode for a functional non-TCR receptor providing specificity for the T cell. Examples of this polynucleotide include, but are not limited to, chimeric NKG2D, chimeric NKp30, chimeric NKp46, or chimeric anti-Her2neu. In a further embodiment, promoter-minigenes are constructed into a retroviral or other suitable expression plasmid and transfected or transduced directly into T cells using standard methods (Zhang, T. et al., (2006) Cancer Res., 66(11) 5927-5933; Barber, A. et al., (2007) Cancer Res., 67(10):5003-5008).

After viral transduction and expansion using any of the methods discussed previously, any T cells that still express TCR/CD3 are removed using anti-CD3 mAbs and magnetic beads using Miltenyi selection columns as previously described (Barber, A. et al., (2007) Cancer Res., 67(10):5003-5008). The T cells are subsequently washed and cultured in IL-2 (25 U/ml) for 3 to 7 days to allow expansion of the effector cells in a similar manner as for use of the cells in vivo.

The expression of TCR αβ and CD3 can be evaluated by flow cytometry and quantitative real-time PCR (qRT-PCR). Expression of TCR-α, TCR-β, CD3ε, CD3-ζ, and GAPDH (as a control) mRNA can be analyzed by qRT-PCR using an ABI7300 real-time PCR instrument and gene-specific TAQMAN® primers using methods similar to those used in Sentman, C. L. et al. ((2004) J. Immunol. 173:6760-6766). Changes in cell surface expression can be determined using antibodies specific for TCR-α, TCR-β, CDR3ε, CD8, CD4, CD5, and CD45.

It is possible that a single shRNA species may not sufficiently inhibit TCR expression on the cell surface. In this case, multiple TCR shRNAs may be used simultaneously to target multiple components of the TCR complex. Each component is required for TCR complex assembly at the cell surface, so a loss of one of these proteins can result in loss of TCR expression at the cell surface. While some or even all TCR expression may remain, it is the receptor function which determines whether the receptor induces an immune response. The functional deficiency, rather than complete cell surface absence, is the critical measure. In general, the lower the TCR expression, the less likely sufficient TCR cross-linking can occur to lead to T cell activation via the TCR complex. While particular embodiments embrace the targeting of TCR-alpha, TCR-beta, and CD3-epsilon, other components of the TCR complex, such as CD3-gamma, CD3-delta, or CD3-zeta, can also be targeted.

The primary aim of removing the TCR from the cell surface is to prevent the activation of the T cell to incompatible MHC alleles. To determine whether the reduction in TCR expression with each shRNA or minigene construct is sufficient to alter T cell function, the T cells can be tested for: (1) cell survival in vitro; (2) proliferation in the presence of mitomycin C-treated allogeneic PBMCs; and (3) cytokine production in response to allogeneic PBMCs, anti-CD3 mAbs, or anti-TCR mAbs.

To test cell survival, transduced T cells are propagated in complete RPMI medium with rhuIL-2 (e.g., 25 U/ml to 50

U/ml). Cells are plated at similar densities at the start of culture and a sample may be removed for cell counting and viability daily for 7 or more days. To determine whether the T cells express sufficient TCR to induce a response against allogeneic cells, transduced or control T cells are cultured with mitomycin C-treated allogeneic or syngeneic PBMCs, e.g., at a 4:1 ratio. The T cells are preloaded with CFSE, which is a cell permeable dye that divides equally between daughter cells after division. The extent of cell division can be readily determined by flow cytometry. Another hallmark of T cell activation is production of cytokines. To determine whether each shRNA construct inhibits T cell function, transduced T cells are cultured with different doses of anti-CD3 mAbs (1.6 to 5000 ng/ml). After 24 hours, cell-free supernatants are collected and the amount of IL-2 and/or IFN-γ produced is quantified by ELISA. PMA/ionomycin are used as a positive control to stimulate the T cells, and T cells alone are used as a negative control.

The effect of exemplary TIMs, e.g., shRNA, truncated dominant-negative proteins, KIR-fusion dominant-negative proteins, and dominant-negative proteins with altered amino acid sequence as a result of single nucleotide alterations, designed for key components of the TCR complex, e.g., CD3-epsilon or CD3-zeta, on effector T cell function was evaluated and the results are provided below in Table 2. These results demonstrate that TCR-deficient T cells may be produced using TIMs.

It is possible that removal of TCR-alpha or TCR-beta components may allow the preferential expansion of TCR-gamma/delta T cells. These T cells are quite rare in the blood, however the presence of these cells can be determined with anti-TCR-gamma/delta antibodies. If there is an outgrowth of these cells, the targeting of CD3-epsilon, which is required for cell surface expression of both TCR-alpha/beta and TCR-gamma/delta at the cell surface, can be used. Both IL-2 and IFN-γ are key effector cytokines that drive T cell expansion and macrophage activation. Therefore, lack of production of these cytokines is a sign of functional inactivation. It is also possible to measure changes in other cytokines, such as TNF-α. Any reduction in T cell survival upon elimination of TCR expression can be determined by culturing the TCR-deficient T cells with PBMCs, which better reflects the in vivo environment and provides support for T cell survival.

Methods of Producing TCR-Deficient T-Cells Expressing a Functional Non-T Cell Receptor In another embodiment of the invention, the T cells stably deficient in functional TCR expression express a functional, non-TCR receptor. In this embodiment, the removal of TCR function (as described previously) is further combined with expression of one or more exogenous non-TCR targeting receptors (such as, for example, chimeric NKG2D (chNKG2D) or Fv molecules). This embodiment provides "universal" cell products, which can be stored for future therapy of any patient with any type of cancer, provided a suitable targeting receptor is employed.

Further embodiments of the invention embrace recombinant expression of receptors in said TCR-deficient T cells, such as chNKG2D, chimeric Fv domains, NKG2D, or any other receptor to initiate signals to T cells, thereby creating potent, specific effector T cells. One of skill in the art can select the appropriate receptor to be expressed by the TCR-deficient T cell based on the disease to be treated. For example, receptors that can be expressed by the TCR-deficient T cell for treatment of cancer would include any receptor to a ligand that has been identified on cancer cells. Such receptors include, but are not limited to, NKG2D (GENBANK accession number BC039836), NKG2A (GENBANK accession number AF461812), NKG2C (GENBANK accession number AJ001684), NKG2F, LLT1, AICL, CD26, NKRP1, NKp30 (e.g., GENBANK accession number AB055881), NKp44 (e.g., GENBANK accession number AJ225109), NKp46 (e.g., GENBANK accession number AJ001383), CD244 (2B4), DNAM-1, and NKp80.

In another embodiment of the invention, such receptors include, but not limited to, chimeric receptors comprising a ligand binding domain obtained from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody, such as anti-Her2neu and anti-EGFR, and a signaling domain obtained from CD3-zeta (CD3ζ) (e.g., GENBANK accession number human NM_198053) (SEQ ID NO:62), Dap10 (e.g., GENBANK accession number AF072845), CD28, 41BB, and/or CD40L.

In a further embodiment of the invention, the chimeric receptor binds MIC-A, MIC-B, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, RON, or one or more members of the ULBP/RAET1 family including ULBP1, ULBP2, ULBP3, ULBP4, ULBP5, and ULBP6.

By way of illustration only, shRNAs or minigenes shown to eliminate cell surface expression of the TCR complex are co-expressed with the chNKG2D receptor via one or more viral vectors. To achieve co-expression in one vector, the shRNA can be driven by a U6 promoter and the chNKG2D receptor by a PGK promoter. In another embodiment, if an IRES sequence is used to separate the genetic elements, then only one promoter is used.

A C-type lectin-like NK cell receptor protein particularly suitable for use in the chimeric receptor includes a receptor expressed on the surface of natural killer cells, wherein upon binding to its cognate ligand(s) it alters NK cell activation. The receptor can work alone or in concert with other molecules. Ligands for these receptors are generally expressed on the surface of one or more tumor cell types, e.g., tumors associated with cancers of the colon, lung, breast, kidney, ovary, cervix, and prostate; melanomas; myelomas; leukemias; and lymphomas (Wu, et al. (2004) J. Clin. Invest. 114: 60-568; Groh, et al. (1999) Proc. Natl. Acad. Sci. USA 96:6879-6884; Pende, et al. (2001) Eur. J. Immunol. 31:1076-1086) and are not widely expressed on the surface of cells of normal tissues.

Examples of such ligands include, but are not limited to, MIC-A, MIC-B, heat shock proteins, ULBP binding proteins (e.g., ULPBs 1-4), and non-classical HLA molecules such as HLA-E and HLA-G, whereas classical MHC molecules such as HLA-A, HLA-B, or HLA-C and alleles thereof are not generally considered strong ligands of the C-type lectin-like NK cell receptor protein of the present invention. C-type lectin-like NK cell receptors which bind these ligands generally have a type II protein structure, wherein the N-terminal end of the protein is intracellular. In addition to any NK cell receptors previously listed above, further exemplary NK cell receptors of this type include, but are not limited to, Dectin-1 (GENBANK accession number AJ312373 or AJ312372), Mast cell function-associated antigen (GENBANK accession number AF097358), HNKR-P1A (GENBANK accession number U11276), LLT1 (GENBANK accession number AF133299), CD69 (GENBANK accession number NM_001781), CD69 homolog, CD72 (GENBANK accession number NM_001782), CD94 (GENBANK accession number NM_002262 or NM_007334), KLRF1 (GEN- BANK accession number NM_016523), Oxidised LDL receptor (GENBANK accession number NM_002543), CLEC-1, CLEC-2 (GENBANK accession number NM_016509), NKG2D (GENBANK accession number BC039836), NKG2C (GENBANK accession number AJ001684), NKG2A (GENBANK accession number AF461812), NKG2E (GENBANK accession number AF461157), WUGSC:H_DJ0701016.2, or Myeloid DAP12-associating lectin (MDL-1; GENBANK accession number AJ271684). In a preferred embodiment of the invention, the NK cell receptor is human NKG2D (SEQ ID NO:58) or human NKG2C (SEQ ID NO:59).

Similar type I receptors which would be useful in the chimeric receptor include NKp46 (GENBANK accession number AJ001383), NKp30 (GENBANK accession number AB055881), or NKp44 (GENBANK accession number AJ225109).

As an alternative to the C-type lectin-like NK cell receptor protein, a protein associated with a C-type lectin-like NK cell receptor protein can be used in the chimeric receptor protein. In general, proteins associated with C-type lectin-like NK cell receptor are defined as proteins that interact with the receptor and transduce signals therefrom. Suitable human proteins which function in this manner further include, but are not limited to, DAP10 (e.g., GENBANK accession number AF072845) (SEQ ID NO:60), DAP12 (e.g., GENBANK accession number AF019562) (SEQ ID NO:61) and FcR gamma.

To the N-terminus of the C-type lectin-like NK cell receptor is fused an immune signaling receptor having an immunoreceptor tyrosine-based activation motif (ITAM), (Asp/Glu)-Xaa-Xaa-Tyr*-Xaa-Xaa-(Ile/Leu)-Xaa$_{6-8}$-Tyr*-Xaa-Xaa-(Ile/Leu) (SEQ ID NOS: 55-57) which is involved in the activation of cellular responses via immune receptors. Similarly, when employing a protein associated with a C-type lectin-like NK cell receptor, an immune signaling receptor can be fused to the C-terminus of said protein (FIG. 1). Suitable immune signaling receptors for use in the chimeric receptor of the present invention include, but are not limited to, the zeta chain of the T-cell receptor, the eta chain which differs from the zeta chain only in its most C-terminal exon as a result of alternative splicing of the zeta mRNA, the delta, gamma and epsilon chains of the T-cell receptor (CD3 chains) and the gamma subunit of the FcR1 receptor. In particular embodiments, in addition to immune signaling receptors identified previously, the immune signaling receptor is CD3-zeta (CD3) (e.g., GENBANK accession number human NM_198053 and NM-000734) (SEQ ID NO:62 and SEQ ID NO:64, respectively), or human Fc epsilon receptor-gamma chain (e.g., GENBANK accession number M33195) (SEQ ID NO:63) or the cytoplasmic domain or a splicing variant thereof. In particular, for example, CD3-zeta has 2 alternatively spliced transcript variants encoding distinct isoforms, i.e., transcript variant 1 (SEQ ID NO:62) and transcript variant 2 (SEQ ID NO:64). The encoded isoform of variant 2 (SEQ ID NO:65) is missing an internal amino acid, as compared to variant 1.

In particular embodiments, a chimeric receptor of the present invention is a fusion between NKG2D and CD3-zeta, or Dap10 and CD3-zeta.

In the nucleic acid construct of the present invention, the promoter is operably linked to the nucleic acid sequence encoding the chimeric receptor of the present invention, i.e., they are positioned so as to promote transcription of the messenger RNA from the DNA encoding the chimeric receptor. The promoter can be of genomic origin or synthetically generated. A variety of promoters for use in T cells are well-known in the art (e.g., the CD4 promoter disclosed by Marodon, et al. (2003) Blood 101(9):3416-23). The promoter can be constitutive or inducible, where induction is associated with the specific cell type or a specific level of maturation. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld (2003) J. Immunol. 171(7):3612-9). Also, it may be further advantageous to use endogenous or exogenous non-coding regions to stabilize the mRNA.

For expression of a chimeric receptor of the present invention, the naturally occurring or endogenous transcriptional initiation region of the nucleic acid sequence encoding N-terminal component of the chimeric receptor can be used to generate the chimeric receptor in the target host. Alternatively, an exogenous transcriptional initiation region can be used which allows for constitutive or inducible expression, wherein expression can be controlled depending upon the target host, the level of expression desired, the nature of the target host, and the like.

Likewise, the signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of T cells so that the chimeric receptor is presented on the surface of the T cell.

Similarly, a termination region can be provided by the naturally occurring or endogenous transcriptional termination region of the nucleic acid sequence encoding the C-terminal component of the chimeric receptor. Alternatively, the termination region can be derived from a different source. For the most part, the source of the termination region is generally not considered to be critical to the expression of a recombinant protein and a wide variety of termination regions can be employed without adversely affecting expression.

As will be appreciated by one of skill in the art, in some instances, a few amino acids at the ends of the C-type lectin-like natural killer cell receptor (or protein associated therewith) or immune signaling receptor can be deleted, usually not more than 10, more usually not more than 5 residues. Also, it may be desirable to introduce a small number of amino acids at the borders, usually not more than 10, more usually not more than 5 residues. The deletion or insertion of amino acids will usually be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

The chimeric construct, which encodes the chimeric receptor can be prepared in conventional ways. Since, for the most part, natural sequences are employed, the natural genes are isolated and manipulated, as appropriate (e.g., when employing a Type II receptor, the immune signaling receptor component may have to be inverted), so as to allow for the proper joining of the various components. Thus, the nucleic acid sequences encoding for the N-terminal and C-terminal proteins of the chimeric receptor can be isolated by employing the polymerase chain reaction (PCR), using appropriate primers which result in deletion of the undesired portions of the gene. Alternatively, restriction digests of cloned genes can be used to generate the chimeric construct. In either case, the sequences can be selected to provide for restriction sites which are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to insure that the sequence encodes the desired chimeric receptor. The sequence can be screened by restriction analysis, sequencing, or the like.

It is contemplated that the chimeric construct can be introduced into T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the present invention are non-replicating in the subject's T cells. A large number of vectors are known which are based on viruses, where the copy number of the virus maintained in the cell is low enough to maintain the viability of the cell. Illustrative vectors include the pFB-neo vectors (STRATAGENE™) as well as vectors based on HIV, SV40, EBV, HSV or BPV. Once it is established that the transfected or transduced T cell is capable of expressing the chimeric receptor as a surface membrane protein with the desired regulation and at a desired level, it can be determined whether the chimeric receptor is functional in the host cell to provide for the desired signal induction (e.g., production of Rantes, Mip 1-alpha, GM-CSF upon stimulation with the appropriate ligand).

As described above, primary human PBMCs are isolated from healthy donors and activated with low-dose soluble anti-CD3 (e.g., 40 ng/ml) and rhuIL-2 (e.g., 50 U/ml), anti-CD3/anti-CD28 beads and rhuIL-2, or irradiated antigen presenting cells and rhuIL-2. The activated T cells are then washed and transduced with retrovirus, e.g., 1 hour spinoculation at 32° C., followed by a 7 hour resting period. Although it is not required to activate T cells for lentiviral transduction, transduction is more efficient and the cells continue to expand in IL-2. The activated cells are washed and transduced, as described herein, followed by a resting period and the submitted to selection, e.g., G418 for 3 days. After selection, the cells are washed and cultured in IL-2 for 2 to 7 days to allow expansion of the effector cells in a similar manner as for use of the cells in vivo. Changes in cell surface expression of receptors are analyzed using antibodies specific for CD3, CD4, NKG2D, or CD5. It is expected that expression of the exogenous, non-TCR receptor will be increased in cells that have been transduced to express that particular receptor, e.g., T cells transduced with chNKG2D-expressing retrovirus are expected to have increased surface expression level of chNKG2D.

The expression of TCRαβ, CD3, and NKG2D can be evaluated by flow cytometry and quantitative qRT-PCR as discussed herein. The number of CD4+ and CD8+ T cells can also be determined. Overall cell numbers and the percentage of TCR complex-deficient, TCR-competent, and chNKG2D-expressing T cells can be determined by flow cytometry. These numbers can be compared to PBMCs that have been transduced with the shRNA or chNKG2D genes alone (as controls). Vector-only transduced cells can also be included as controls.

After viral transduction and expansion, the TCR+ and TCR– cells can be separated by mAbs with magnetic beads over Miltenyi columns and TCR-deficient T cells expressing the chNKG2D receptor are identified and isolated. For example, chNKG2D expression can be verified by QRT-PCR using specific primers for the chNKG2D receptor (Zhang, T. et al. (2007) *Cancer Res.* 67:11029-11036; Barber, A. et al. (2008) *J. Immunol.* 180:72-78). Function of these TCR-deficient chNKG2D+ cells can be determined by culturing the cells with allogeneic PBMCs or tumor cells that express NKG2D ligands. T cell proliferation and cytokine production (e.g., IFN-γ and/or IL-2) can be determined by flow cytometry and ELISA, respectively. To determine whether the T cells that have lost TCR function and retained chNKG2D function, transduced or control T cells will be cultured with anti-CD3 (1.6 to 5000 ng/ml), mitomycin C-treated allogeneic PBMCs, or syngeneic PBMCs. Cell supernatants are collected, and the extent of cytokine production (e.g., IFN-γ and/or IL-2) is determined by ELISA. The T cells can be preloaded with CFSE, which is a cell permeable dye that divides equally between daughter cells after division. The extent of cell division can be readily determined by flow cytometry.

Another hallmark of T cell activation is production of cytokines. To determine whether TCR-deficient chNKG2D+ cells induce T cell activation, the T cells are cocultured with mitomycin C-treated allogeneic PBMCs, syngeneic PBMCs, or tumor cells: P815-MICA (a murine tumor expressing human MICA, a ligand for NKG2D), P815, A2008 (a human ovarian tumor cell, NKG2D ligand+), and U266 (a human myeloma cell line, NKG2D ligand+). After 24 hours, cell-free supernatants are collected and the amount of IL-2 and IFN-γ produced is quantified by ELISA. T cells alone and culture with syngeneic PBMCs are used as a negative controls. A greater than 40% reduction in IFN-γ production was observed in TIM7– and TIM8-expressing T cells that also co-expressed chNKG2D (results not shown in FIG. 3).

Subsequently, the transduced T cells are reintroduced or administered to the subject to activate anti-tumor responses in said subject. To facilitate administration, the transduced T cells according to the invention can be made into a pharmaceutical composition or made implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed which does not ineffectuate the cells expressing the chimeric receptor. Thus, desirably the transduced T cells can be made into a pharmaceutical composition containing a balanced salt solution, preferably Hanks' balanced salt solution, or normal saline.

Methods of Ameliorating or Reducing Symptoms of, or Treating, or Preventing, Diseases and Disorders Using TCR-deficient T-cells The invention is also directed to methods of reducing or ameliorating, or preventing or treating, diseases and disorders using the TCR-deficient T cells described herein, isolated populations thereof, or therapeutic compositions comprising the same. In one embodiment, the TCR-deficient T cells described herein, isolated populations thereof, or therapeutic compositions comprising the same are used to reduce or ameliorate, or prevent or treat, cancer, infection, one or more autoimmune disorders, radiation sickness, or to prevent or treat graft versus host disease (GVHD) or transplantation rejection in a subject undergoing transplant surgery.

The TCR-deficient T cells described herein, isolated populations thereof, or therapeutic compositions comprising the same are useful in altering autoimmune or transplant rejection because these effector cells can be grown in TGF-β during development and will differentiate to become induced T regulatory cells. In one embodiment, the functional non-TCR is used to give these induced T regulatory cells the functional specificity that is required for them to perform their inhibitory function at the tissue site of disease. Thus, a large number of antigen-specific regulatory T cells are grown for use in patients. The expression of FoxP3, which is essential for T regulatory cell differentiation, can be analyzed by flow cytometry, and functional inhibition of T cell proliferation by these T regulatory cells can be analyzed by examining decreases in T cell proliferation after anti-CD3 stimulation upon co-culture.

Another embodiment of the invention is directed to the use of TCR-deficient T cells described herein, isolated populations thereof, or therapeutic compositions comprising the same for the prevention or treatment of radiation sickness. One challenge after radiation treatment or exposure (e.g. dirty bomb exposure, radiation leak) or other condition that ablates bone marrow cells (certain drug therapies) is to reconstitute the hematopoietic system. In patients undergoing a bone marrow transplant, the absolute lymphocyte count on day 15 post-transplant is correlated with successful outcome. Those patients with a high lymphocyte count reconstitute well, so it is important to have a good lymphocyte reconstitution. The reason for this effect is unclear, but it may be due to lymphocyte protection from infection and/or production of growth factors that favors hematopoietic reconstitution.

In this embodiment, TCR-deficient T cells described herein, isolated populations thereof, or therapeutic compositions comprising the same result in the production of a large number of T cells that are unable to respond to allogeneic MHC antigens. Hence, these T cells may be used to reconstitute people and offer protection from infection, leading to faster self-reconstitution of people suffering from full or partial bone marrow ablation due to radiation exposure. In the event of a catastrophic or unexpected exposure to high doses of radiation, TCR-deficient T cells described herein having another functional receptor, isolated populations thereof, or therapeutic compositions comprising the same can be infused rapidly into patients to offer some reconstitution of their immune response and growth factor production for days to weeks until their own hematopoietic cells have reconstituted themselves, or until the person has been treated with an additional source of hematopoietic stem cells (e.g. a bone marrow transplant).

One of skill would understand how to treat cancer, infection, transplantation rejection, one or more autoimmune disorders, radiation sickness, or GVHD based on their experience with use of other types of T cells.

In addition to the illustrative TCR-deficient chNKG2D+ T cells described herein, it is contemplated that TCR-deficient T cells can be modified or developed to express other functional receptors useful in treatment of diseases such as cancer or infection as described previously. Briefly, the treatment methods of the invention contemplate the use of TCR-deficient T cells expressing functional non-TCR receptors, such as chNKG2D, chimeric Fv domains, NKG2D, or any other receptor to initiate signals to T cells, thereby creating potent, specific effector T cells. One of skill in the art can select the appropriate receptor to be expressed by the TCR-deficient T cell based on the disease to be treated. For example, receptors that can be expressed by the TCR-deficient T cell for treatment of cancer would include any receptor that binds to a ligand that has been identified on cancer cells. Such receptors include, but are not limited to, NKG2D, NKG2A, NKG2C, NKG2F, LLT1, AICL, CD26, NKRP1, NKp30, NKp44, NKp46, CD244 (2B4), DNAM-1, and NKp80.

In another embodiment of the invention, such receptors include, but not limited to, chimeric receptors comprising a ligand binding domain obtained from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody such as anti-Her2neu and anti-EGFR, and a signaling domain obtained from CD3zeta, Dap10, CD28, 41BB, and CD40L.

In a further embodiment of the invention, the chimeric receptor binds MIC-A, MIC-B, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, RON, or one or more members of the ULBP/RAET1 family including ULBP1, ULBP2, ULBP3, ULBP4, ULBP5, and ULBP6.

Also embraced by the present invention are TCR-deficient T cells that express a non-TCR pathogen-associated receptor and the use of the TCR-deficient T cells expressing the pathogen receptor to treat or prevent infectious disease. In this embodiment, the non-TCR receptor binds to virus antigen or viral-induced antigen found on the surface of an infected cell. The infection to be prevented or treated, for example may be caused by a virus, bacteria, protozoa, or parasite. Viruses which can be treated include, but are not limited to, HCMV, EBV, hepatitis type A, hepatitis type B (HBV), hepatitis type C(HCV), ebola virus, VSV, influenza, varicella, adenovirus, herpes simplex type I (HSV-1), herpes simplex type 2 (HSV-2), rinderpest, rhinovirus, echovirus, rotavirus, respiratory syncytial virus, papilloma virus, cytomegalovirus (CMV), echinovirus, arbovirus, hantavirus, coxsackie virus, mumps virus, measles virus, rubella virus, polio virus, and/or human immunodeficiency virus type 1 or type 2 (HIV-1, HIV-2). Non-viral infections which can be treated using the TCR-deficient T cells include, but are not limited to, infectious *Staphylococcus* sp., *Enterococcus* sp., *Bacillus anthracis, Lactobacillus* sp., *Listeria* sp., *Corynebacterium diphtheriae, Nocardia* sp., *Streptococcus* sp., *Pseudomonas* sp., *Gardnerella* sp., *Streptomyces* sp., *Thermoactinomyces vulgaris, Treponema* sp., *Camplyobacter* sp., *Raeruginosa* sp., *Legionella* sp., *N. gonorrhoeae*, N. meningitides, F. meningosepticum, F. odoraturn, *Brucella* sp., *B. pertussis*, *B. bronchiseptica*, *E. coli*, *Klebsiella*, *Enterobacter*, *S. marcescens*, *S. liquefaciens*, *Edwardsiella*, *P. mirabilis*, *P. vulgaris*, *Streptobacillus*, *R. fickettsfi*, *C. psittaci*, *C. trachornatis*, *M. tuberculosis*, *M. intracellulare*, *M. folluiturn*, *M. laprae*, *M. avium*, *M. Bovis*, *M. africanum*, *M. kansasii*, *M. lepraernurium*, *trypanosomes*, *Chlamydia*, or *rickettsia*.

Efficacy of the compositions of the present invention can be demonstrated in the most appropriate in vivo model system depending on the type of drug product being developed. The medical literature provides detailed disclosure on the advantages and uses of a wide variety of such models. For example, there are many different types of cancer models that are used routinely to examine the pharmacological activity of drugs against cancer such as xenograft mouse models (e.g., Mattern, J. et al. 1988. *Cancer Metastasis Rev.* 7:263-284; Macor, P. et al. 2008. Curr. Pharm. Des. 14:2023-2039) or even the inhibition of tumor cell growth in vitro. In the case of GVHD, there are models in mice of both acute GVHD (e.g., He, S. et al. 2008. *J. Immunol.* 181:7581-7592) and chronic GVHD (e.g., Xiao, Z. Y. et al. 2007. *Life Sci.* 81:1403-1410).

Once the compositions of the present invention have been shown to be effective in vivo in animals, clinical studies may be designed based on the doses shown to be safe and effective in animals. One of skill in the art can design such clinical studies using standard protocols as described in textbooks such as Spilker (2000. *Guide to Clinical Trials*. Lippincott Williams & Wilkins: Philadelphia).

Administration

In one embodiment of the invention, the TCR-deficient T cells are administered to a recipient subject at an amount of between about $10^6$ to $10^{11}$ cells. In a preferred embodiment of the invention, the TCR-deficient T cells are administered to a recipient subject at an amount of between $10^8$ to $10^9$ cells. In a preferred embodiment of the invention, the TCR-deficient T cells are administered to a recipient subject with a frequency of once every twenty-six weeks or less, such as once every sixteen weeks or less, once every eight weeks or less, or once every four weeks or less.

These values provide general guidance of the range of transduced T cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

A person of skill in the art would be able to determine an effective dosage and frequency of administration based on teachings in the art or through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins. The dosing schedule can be based on well-established cell-based therapies (see, e.g., Topalian and Rosenberg (1987) Acta Haematol. 78 Suppl 1:75-6; U.S. Pat. No. 4,690,915) or an alternate continuous infusion strategy can be employed.

In another embodiment of the invention, the TCR-deficient T cells are administered to a subject in a pharmaceutical formulation.

In one embodiment of the invention, the TCR-deficient T cells may be optionally administered in combination with one or more active agents. Such active agents include analgesic, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lornoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Nerve Growth Factor (NGF), Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib.

Antibiotics include Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Timidazole, Tobramycin, Trimethoprim, Trimethoprim-Sulfamethoxazole, Troleandomycin, Trovafloxacin, and Vancomycin.

Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a population of TCR-deficient T cells. In one embodiment of the invention, the active therapeutic agent is a population of TCR-deficient T cells expressing a functional, non-TCR receptor. The excipient generally does not provide any pharmacological activity to the formulation, though it may provide chemical and/or biological stability. Exemplary formulations can be found, for example, in Remington's Pharmaceutical Sciences, $19^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In a particularly preferred embodiment of the invention, appropriate carriers include, but are not limited to, Hank's Balanced Salt Solution (HBSS), Phosphate Buffered Saline (PBS), or any freezing medium having for example 10% DMSO and 90% human serum.

Pharmaceutical compositions typically must be sterile and stable under the conditions of manufacture and storage. The invention contemplates that the pharmaceutical composition is present in lyophilized form. The composition can be formulated as a solution. The carrier can be a dispersion medium containing, for example, water.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, liquids, solutions, suspensions, emulsions, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to T-cell receptor deficient T-cell compositions and methods of use thereof were disclosed in U.S. Provisional patent application No. 61/255,980, filed Oct. 29, 2009, the disclosure of which is herein incorporated by reference in its entirety.

Certain teachings related to the production of T cells expressing chimeric receptors and methods of use thereof were disclosed in U.S. patent application publication no. US 2010/0029749, published Feb. 4, 2010, the disclosure of which is herein incorporated by reference in its entirety.

Certain polynucleotide sequences useful in the production of T-cell receptor deficient T-cells of the invention are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1

Production of T Cell Receptor (TCR)-Deficient T Cells

Minigenes are encoded on a retrovirus expression plasmid (e.g. pFB-neo or pSFG) containing 5' and 3' LTR sequences. The plasmids are packaged in a retroviral packaging cell line, such as PT67 or PG13, and viral particles are collected once the packaging cells have grown to confluence. T cells are then activated by PHA, anti-CD3, or anti-CD3/28 mAbs for 1 to 3 days in complete medium (or serum free medium) plus rIL-2 (25 U/ml), and T cells are transduced by spinoculation at 32° C. in the presence of retronectin or polybrene. After resting for some 5 to 7 hours, the cells are washed and placed in fresh medium plus IL-2 for 2 to 7 days. Cells are counted periodically to avoid excessive cell concentration (i.e., >$2\times10^6$ cells/ml) and re-plated at $7\times10^5$ cells/ml. Selection medium to remove non-transduced T cells is optionally used after 2 days for a period of 3 to 5 days. Live cells are harvested by Lymphoprep™ (Sentinel, Milan, Italy) gradient and further expanded for 1 to 3 days.

Following incubation, cells are analyzed for expression and function of the TCR. Functional non-TCR receptor expression may also be analyzed at this time, if appropriate. Flow cytometry is used to test for TCR/CD3 expression using fluorochrome-labeled antibodies. Live cells are stained with antibodies against CD5, CD8, and CD4, in combination with an antibody against CD3ε, TCRα, TCRβ, TCRγ, or TCRδ. If the expression of either the CD3 or TCR genes is used, the expression of both TCR proteins and CD3 proteins should be severely reduced compared to control vector treated T cells. Isotype control antibodies are used to control for background fluorescence. To identify T cells, cells are gated on CD5, then expression of CD4, CD8, CD3, and TCR is determined. Multiple samples are used for each treatment and appropriate compensation of fluorochrome emission spectra is used. The expression of another receptor (e.g. chNKG2D) is determined using specific antibodies and flow cytometry, as previously described in the art (Zhang, T. et al., (2006) Cancer Res., 66(11) 5927-5933; Barber, A. et al., (2007) Cancer Res., 67(10):5003-5008).

To test for functional deficiency of the TCR, anti-CD3 stimulation of effector cells is used at the end of culture to measure interferon (IFN)-gamma production after 24 hours. T cells ($2 \times 10^5$) are cultured with soluble anti-CD3 (OKT3) mAbs in complete medium. After 24 hours, cell-free conditioned medium is collected and assayed by ELISA for IFN-gamma. Changes in TCR expression or function should be reflected in reduced IFN-gamma production.

To test for the function of the functional non-TCR, specific cytokine production by T cells incubated with tumor cells that do, or do not, express their specific ligand is used. For example, to test the function of chNKG2D, $10^5$ T cells are incubated with $10^5$ P815-MICA tumor cells (ligand+), $10^5$ P815 (ligand−) cells, $10^5$ RPMI8226 cells (ligand+) or T cells alone. After 24 hours, cell-free conditioned medium is collected and IFN-g measured by ELISA. Chimeric NKG2D T cells produce IFN-γ after culture with ligand-expressing tumor cells (Zhang, T. et al., (2006) Cancer Res., 66(11) 5927-5933; Barber, A. et al., (2007) Cancer Res., 67(10): 5003-5008). It is also possible to test cellular cytotoxicity against ligand+ tumor cells, as previously described in the art (Zhang, T. et al., (2006) Cancer Res., 66(11) 5927-5933). Specificity is shown using ligand-tumor cells or specific receptor blocking mAbs.

Example 2

Production of T Cell Receptor (TCR)-Deficient T Cells Expressing chNKG2D

In this example, simultaneous expression of a chNKG2D receptor and inhibition of endogenous TCR expression is performed. In this example, a murine chNKG2D receptor is used, composed of NKG2D in combination with a N-terminally attached CD3-zeta. The chNKG2D receptor is generated and expressed in murine T-cells. NKG2D is a type II protein, in which the N-terminus is located intracellularly (Raulet (2003) Nat. Rev. Immunol. 3:781-790), whereas the CD3-zeta chain is type I protein with the C-terminus in the cytoplasm (Weissman, et al. (1988) Proc. Natl. Acad. Sci. USA 85:9709-9713). To generate a chimeric NKG2D-CD3-zeta fusion protein, an initiation codon ATG is placed ahead of the coding sequence for the cytoplasmic region of the CD3-zeta chain (without a stop codon TAA) followed by a wild-type NKG2D gene. Upon expression, the orientation of the CD3-zeta portion is reversed inside the cells. The extracellular and transmembrane domains are derived from NKG2D. A second chimeric gene encoding the Dap10 gene followed by a fragment coding for the CD3-zeta cytoplasmic domain is also constructed. FIG. 1 presents the structures of the chimeric and wild-type receptors.

An shRNA is operably linked in a lentiviral vector with the chNKG2D receptor. To achieve expression of both genes, the shRNA is driven by a U6 promoter and the chNKG2D receptor by a PGK promoter. Primary human PBMCs are isolated from healthy donors and activated with low-dose soluble anti-CD3 and 25 U/ml rhuIL-2 for 48 hours. Although it is not required to activate T cells for lentiviral transduction, the transduction will work more efficiently and allow the cells to continue to expand in IL-2. The activated cells are washed and transduced using a 1 h spin-fection at 30° C., followed by a resting period for 7 h. The cells are washed and cultured in 25 U/ml IL-2 for 3 to 7 d to allow expansion of the effector cells in a similar manner as we do for use of the cells in vivo. The expression of TCRαβ, CD3, and NKG2D is evaluated by flow cytometry and quantitative realtime-PCR (QRT-PCR). The number of CD4+ and CD8+ T cells are determined by flow cytometry. Overall cell numbers and the percentage of TCR complex deficient and expressing T cells are determined by flow cytometry. These are compared to PBMCs that are transduced with the shRNA or chNKG2D genes alone (as controls). Vector-only transduced cells are also included as controls.

It is anticipated that those cells with no or little TCR expression at the cell surface will express higher amounts of cell surface NKG2D because of co-expression of the chNKG2D receptor.

As an alternative, transduction may occur with two viruses at the same time, one with the shRNA construct and one with the chNKG2D receptor. A larger amount of the chNKG2D virus is used to ensure high expression of chNKG2D in those T cells that lack TCR expression. TCR+ T cells that may remain are removed to obtain TCR−, chNKG2D+ T cells.

After viral transduction and expansion, the TCR+ and TCR− cells are separated by mAbs with magnetic beads over Miltenyi columns. Verification of chNKG2D expression is performed by QRT-PCR using specific primers for the chNKG2D receptor.

To determine whether the T cells have lost TCR function and retained chNKG2D function, transduced or control T cells are cultured with mitomycin C-treated allogeneic PBMCs or syngeneic PBMCs. The T cells are preloaded with CFSE, which is a cell permeable dye that divides equally between daughter cells after division. The extent of cell division can be easily determined by flow cytometry.

To determine whether the shRNA construct can inhibit TCR function and allow chNKG2D receptor function, transduced T cells are cultured with mitomycin C-treated allogeneic PBMCs, syngeneic PBMCs, or tumor cells: P815-MICA (a murine tumor expressing human MICA, a ligand for NKG2D), P815, A2008 (a human ovarian tumor cell, NKG2D ligand+), and U266 (a human myeloma cell line, NKG2D ligand+). After 48 hours, cell-free supernatants are collected and the amount of IL-2 and IFN-γ produced will be quantitated by ELISA. T cells alone are used as a negative control.

Example 3

In Vivo Administration of T Cell Receptor (TCR)-Deficient T Cells Expressing chNKG2D In this example, the TCR-deficient T cells expressing a murine chNKG2D receptor as produced in Example 2 are administered to mice to evaluate the in vivo therapeutic potential of said T cells on certain cancers. The chimeric NKG2D-bearing T cells ($10^6$) are co-injected with RMA/Rae-10 tumor cells ($10^5$) subcutaneously to C57BL/6 mice. Chimeric NKG2D-bearing, TCR-deficient T cell-treated mice that are tumor-free or have tumor-inhibited growth of RMA/Rae-1β tumors after 30 days reflects therapeutic anti-cancer activity in these mice.

In a second and more stringent model, transduced T cells ($10^7$) are adoptively transferred i.v. into B6 mice one day before RMA/Rae-1β s.c. tumor inoculation in the right flank. Suppression of the growth of the RMA/Rae-1β tumors (s.c.) compared with control vector-modified T cells reflects therapeutic anti-cancer activity in these mice. As for toxicity of treatment with chimeric NKG2D-modified T cells, it is anticipated that the animals will not show any overt evidence of inflammatory damage (i.e., ruffled hair, hunchback or diarrhea, etc.) when treated with chimeric NKG2D-bearing T cells, which would be reflective of a lack of overt toxicity.

In a more stringent model of established ovarian tumors (ID8), transduced chNKG2D T cells ($5 \times 10^6$ T cells, i.p.) are injected into mice bearing tumors for 5 weeks. Mice are further injected with T cells at 7 and 9 weeks following tumor challenge. Under these conditions, mice treated with chNKG2D T cells will remain tumor-free for more than 250 days, whereas mice treated on a similar schedule with control T cells will die from tumor growth within 100 days. As for toxicity of treatment with chimeric NKG2D-modified T cells, it is anticipated that the animals will not show any overt evidence of inflammatory damage (i.e., ruffled hair, hunchback or diarrhea, etc.) when treated with chimeric NKG2D-bearing T cells, which would be reflective of a lack of overt toxicity.

In a model of multiple myeloma, mice bearing 5T33mM tumor cells are treated on day 12 post tumor cell infusion with chNKG2D T cells ($5 \times 10^6$ cells, i.v.). This treatment will result in an increased life-span of all mice and about half of these mice will be long-term, tumor-free survivors. Mice treated with control T cells will succumb to their tumors within 30 days. No overt evidence of toxicity will be observed due to treatment with the chNKG2D T cells.

Because the immune system can select for tumor variants, the most effective immunotherapies for cancer are likely going to be those that induce immunity against multiple tumor antigens. In a third experiment, it is tested whether treatment with chimeric NKG2D-bearing T cells will induce host immunity against wild-type tumor cells. Mice that are treated with chimeric NKG2D-bearing T cells and 5T33MM tumor cells, and are tumor-free after 80 days, are challenged with 5T33MM tumor cells. Tumor-free surviving mice are resistant to a subsequent challenge of 5T33MM cells ($3 \times 10^5$), compared to control naïve mice which succumb to the tumor within an average of 27 days. However, tumor-free surviving mice are not resistant to a subsequent challenge of RMA-Rae1 tumor cells ($3 \times 10^5$), and succumb to the tumor in a similar time-span as naïve mice (20 days). This indicates that adoptive transfer of chimeric NKG2D-bearing T cells will allow hosts to generate tumor-specific T cell memory.

In this invention, four classes of TCR-inhibitory molecules (TIMs) that effect T cell function are provided. Table 2 is a summary of the effect of 19 different TIMs on effector T cell function either in response to soluble anti-CD3 (OKT3 (200 ng/ml)) stimulation (CD3), or culture with allogeneic PBMCs (Allo). Designations on the left refer to the class of TIM. Numerical values indicate percent reduction in TCR inhibition relative to control pFB vector transduced T cells. NI: no inhibition. ND: not done.

TABLE 2

Summary of TCR Inhibitory Molecules (TIM) effect on T cell function.

| Class of TIM | | CD3 | Allo |
|---|---|---|---|
| shRNA | TIM1* | 22.6 | ND |
| | TIM2* | ND | ND |
| | TIM3* | 14.9 | ND |
| | TIM4** | NI | ND |
| Truncated Proteins | TIM5*** | NI | NI |
| | TIM6** | NI | 56 |
| | TIM7** | 44 | 90 |
| | TIM8** | 58 | 100 |
| KIR-fusion Proteins | TIM9** | 32.7 | ND |
| | TIM10** | 28 | ND |
| | TIM11** | 32 | ND |
| | TIM12** | −12 | 40 |
| | TIM13** | ND | −26 |
| Mutations | TIM14** | NI | ND |
| | TIM15** | −6 | 35 |
| | TIM16** | 23.2 | 27 |
| | TIM17** | 8.2 | −9 |
| | TIM18** | −28 | 21 |
| | TIM19** | 33.9 | 8 |

Example 4

Production of T Cell Receptor (TCR)-Deficient T Cells Using shRNAs Targeting Nucleic Acids Encoding CD3-Epsilon or CD3-Zeta In this example, endogenous TCR expression was inhibited using shRNA sequences that target nucleic acids encoding CD3-epsilon or CD3-zeta.

shRNA sequences cloned into the retroviral vector pSM2c (Open Biosystems), with expression controlled by U6 promoter, were purchased. These shRNA constructs were used to block expression of the CD3-epsilon and/or CD3-zeta proteins, such that the T cell no longer produced one of the key components of the TCR complex. Consequently, the TCR complex was destabilized and cell surface expression of a functional TCR was prevented, resulting in reduced T cell function via the TCR complex. The sequence of shRNAs against CD3-epsilon or CD3-zeta are described in Table 1, which correspond to SEQ ID NOS:9-26 and 68-71, respectively To determine whether the shRNAs altered TCR function, IFN-gamma production was measured in response to (i) soluble anti-CD3 stimulation (CD3), or (ii) in response to culture with allogeneic PBMCs (Allo). In particular, T cells treated with TIM1 or TIM3 had a 22.6% or 14.9% reduction in TCR inhibition, respectively, following stimulation with 200 ng/ml of anti-CD3 monoclonal antibody. See Table 2 supra.

Example 4

Production of T Cell Receptor (TCR)-Deficient T Cells Using a Dominant Negative Inhibitor of CD3-zeta In this example, over-expression of a dominant-negative inhibitor protein, i.e., a TIM, interrupted TCR expression and function. Endogenous TCR expression was inhibited using a dominant negative inhibitor protein comprising CD3-zeta altered to include an inhibitory signal from KIR2DL1, and the resulting T cell were not activated in response to TCR stimulation.

Minigene constructs that incorporated all, or part of, a modified polynucleotide encoding for CD3-zeta were generated by PCR using CD3-zeta and KIR2DL1 cDNA templates, corresponding to SEQ ID NO: 64 and SEQ ID NO:66, respectively, purchased from Open Biosystems (Huntsville, Ala.). All PCRs were done using High-Fidelity DNA Polymerase Phusion (New England Biolabs, Ipswich, Mass.), and primers were synthesized by Integrated DNA Technologies (Coralville, Iowa). Using established protocols, each construct was cloned into the retroviral vector pFB-neo (Stratagene), with expression controlled by the 5' LTR. The resulting constructs were screened and confirmed for accuracy by sequencing and analyzed by DNA dynamo (Blue Tractor Software Ltd). The DNA sequences and their predicted protein sequences correspond to SEQ ID NOS: 68-101.

The TIMs were expressed in primary T cells using a retroviral expression system. Two different packaging cell lines were used to produce viruses with either a low or high titer. Low titer virus was produced by GP2-293T cells that were transiently transfected with the packaging plasmid and an envelope plasmid. After 72 hours, viral supernatant was harvested and titers were measured by infecting NIH-3T3 cells following selection with G418. The titers of the viruses produced by this system were between $5 \times 10^5$ and $1 \times 10^7$ CFU/ml. To produce high titer viruses, virus was produced by the GP2-293T system to transduce PT67 packaging cells. PT67 cells infected with viral particles were selected under treatment with G418 for 5 days. TIM-expressing PT67 cells were expanded and used for virus production. 72 hours after cells reached confluence, viral supernatant was harvested and titers were measured in NIH-3T3. The titers of the viruses obtained by this system were in the range of $7 \times 10^7$ to $2 \times 10^8$ CFU/ml.

To transduce human T cells, primary human PBMCs were isolated from healthy donors and activated with 40 ng/ml of soluble anti-CD3 and 50 U/ml rhuIL-2 for 72 hours. The activated T cells were washed and transduced with retrovirus produced by either low or high titer viruses using 1 hour spin-infection at 32° C., followed by a 6 hour resting period. The cells were washed and cultured in 50 U/ml IL-2 for 48 hours, and then submitted to selection for 3 days. After selection, live cells were isolated using Lymphoprep (Mediatech), and the effector cells were expanded in 50 U/ml IL-2 for 48 hours when the cells were used for functional assays. The endogenous cell expression of CD3-epsilon and CD3-zeta in cells transduced with shRNAs, and the decrease in expression of the genes by shRNA, were analyzed by quantitative real time PCR (qRT-PCR). Briefly, RNA was extracted from transduced T cells, and 0.5-1 ug of total RNA was reverse transcribed using QuantiTect Rev. Transcription Kit (Qiagen). The resulting cDNA was used with SYBR green (Applied Biosystems) for qRT-PCR analysis, and the data normalized to glyceraldehyde-3-phosphate dehydrogenase (GAPDH) levels. The changes in cell surface expression were analyzed using antibodies specific for CD3, CD8, CD4, and CD5, and no difference in the expression of these cell surface molecules was observed in TIM-expressing T cells compared to vector control.

To determine whether the reduction in TCR expression with each shRNA or minigene construct (which removed or disrupted the TCR on the cell surface) was sufficient to prevent the activation of the T cell to TCR stimulation, the T cells were tested for: (1) cell survival in vitro; and (2) cytokine production in response to allogeneic PBMCs and/or anti-CD3 mAb.

To test cell survival, transduced T cells were propagated in complete RPMI medium with rhuIL-2 (50 U/ml). Cells were plated at similar densities at the start of culture, and a sample was removed for cell counting and viability daily for 7 or more days. No difference was observed in the growth of TIM-expressing T cells compared the correspondent vector control-expressing T cells. To determine whether the T cells expressed sufficient TCR to induce a response against allogeneic cells, transduced or control T cells were cultured with allogeneicor autologous PBMCs at a ratio of 4:1. After 24 hours, cell-free supernatants were collected and the amount of IFN-γ produced was quantified by ELISA. T cells alone, including PBMCs and transduced cells, were used as negative controls. Among the TCR-inhibitory molecules analyzed, two minigenes (TIM7 and TIM8) were identified that were able to significantly reduce the TCR function in T cells. See, FIG. 2. The allogeneic assay was performed using 19 different donors expressing TIM7 or TIM8, where each donor was cultured with 3 different allogeneic PBMCs. An average reduction in IFN-γ production of 49% was observed in TIM7-expressing T cells, and an average reduction of 60% was observed in TIM8-expressing T cells.

To determine whether each TIM inhibited T cell function by direct antibody stimulation of the TCR complex, TIM-transduced T cells were treated with a range of different concentrations of anti-CD3 mAbs (1.6 to 5000 ng/ml). After 24 hours, cell-free supernatants are collected and the amount of IFN-γ produced was quantified by ELISA. T cells alone were used as a negative control. When the cells were stimulated with 200 ng/ml of anti-CD3 mAb for 24 hrs, a maximum reduction in IFN-γ production of 44% and 58% was observed in T cells expressing TIM7 and TIM8, respectively. Collectively, this indicates that a reduction in TCR expression, e.g., using TIMs to remove or disrupt the TCR, is sufficient to alter T cell function.

Example 5

Production of T Cell Receptor (TCR)-Deficient T Cells Expressing chNKG2D

In this example, simultaneous over-expression of a dominant-negative TCR inhibitor protein, i.e., a TIM, and expression of a chimeric tumor targeting receptor was performed. In particular, endogenous TCR expression was inhibited using a TIM and the chNKG2D chimeric receptor, i.e., NKG2D linked to the cytoplasmic domain of CD3-zeta, was expressed. NKG2D associates with Dap10 to provide both primary and secondary activation signals to T cells. See, Zhang, T. et al. 2006. Cancer Res. 66(11): 5927-5933. The ligands for NKG2D are expressed by most human tumor cells, but not on most normal cells.

In order to test the expression of both of a TIM and a chimeric tumor targeting receptor, primary human PBMCs were isolated from healthy donors and activated with 40 ng/ml of soluble anti-CD3 and 50 U/ml rhuIL-2 for 72 hours. The activated T cells were washed and transduced with high-titer retroviruses using 1 hour spinoculation at 32° C., followed by a 7 hour resting period. Equal amounts of TIM and chNKG2D virus were used for transduction. The cells were washed and cultured in 50 U/ml IL-2 for 48 hours, and then submitted to G418 selection for 3 days. After selection, live cells were isolated using Lymphoprep (Mediatech), and the effector cells were expanded in 50 U/ml IL-2 for 48 hours when the cells were used for functional assays. The changes in cell surface expression were analyzed using antibodies specific for CD3, CD4, NKG2D and CD5. No significant difference was observed in the expression of these cell surface molecules in TIM-expressing T cells compared to vector control, except for a higher expression of NKG2D receptor in cells transduced with the chNKG2D virus, as expected.

To determine whether TIM+ chNKG2D+ cells would have a reduced response to allogeneic cells, but an increased response to tumor cells, T cells were co-cultured with allogeneic PBMCs, syngeneic PBMCs, or tumor cells: RPMI8226 (a human myeloma cell line, NKG2D ligand+), PANC-1 (a human pancreatic cell line, NKG2D+), or NIH-3T3 (a normal mouse fibroblast cell line, NKG2D ligand−), as a negative control. After 24 hours, cell-free supernatants were collected and the amount of IFN-γ produced was quantified by ELISA. T cells alone and culture with syngeneic PBMCs were used as a negative control.

Figure 3:
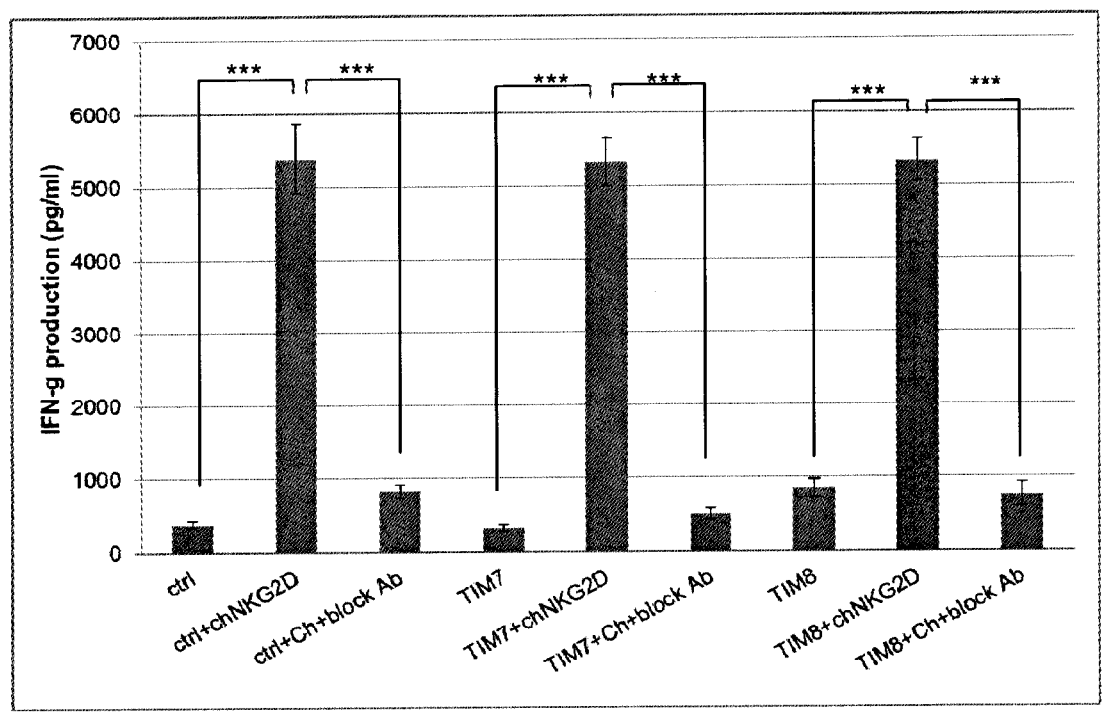
FIG. 3 illustrates activation of TIM-expressing T cells using a recombinant targeting receptor for cancer. TIM-expressing T cells that co-expressed a chimeric NKG2D receptor (chNKG2D), which recognizes specific ligands on many types of tumor cells, produced an increased amount of IFN-γ upon coculture with RPMI8226 myeloma tumor cells. In some wells, a blocking NKG2D mAb was included to prevent the chNKG2D from recognizing its ligands on the tumor cells, and this demonstrates the specific response of the chNKG2D receptor in these T cells.

On the allogeneic assay, a 45% reduction in IFN-γ production was observed in TIM7-expressing T cells, and a 44% reduction in IFN-γ production was observed in TIM8-expressing T cells that had co-expression of chNKG2D compared to cells expressing the vector control. When cultured with tumor cells, a significant increase in the amount of IFN-γ production was observed in response to tumor cells in TIM+ chNKG2D+ cells, compared to cells expressing TIM only, when the tumor cells expressed NKG2D ligands (RPMI8226 and PANC-1), but not when cultured with ligand-deficient tumor cells (NIH-3T3). See FIG. 3 showing a representative experiment using RPMI8226. The same experiment also demonstrated that higher IFN-γ production was NKG2D-dependent, because incubation with a blocking mAb for NKG2D resulted in no increased in IFN-γ production.

What is claimed is:

1. A method of producing one or more, modified primary human T cells, which modified primary human T cells are derived from primary human T cells isolated from a human donor that (i) are modified to reduce expression of the endogenous T cell receptor (TCR), and (ii) are further modified to express at least one functional exogenous non-TCR that comprises a chimeric receptor comprising a ligand binding domain and a signaling domain, said method including the following:

(a) introducing into one or more primary human T cells isolated from a human donor at least one small-hairpin RNA (shRNA) which each target a nucleic acid that encodes a component of a functional TCR that is endogenously expressed by an unmodified primary human T cell isolated from said human donor, wherein expression of said at least one shRNA reduces the expression of the endogenous TCR by blocking or inhibiting the expression of at least one targeted component of said endogenous TCR, and (b) further introducing into said one or more primary human T cells isolated from a human donor at least one nucleic acid that results in the expression of a functional exogenous non-TCR receptor that comprises a chimeric receptor comprising a ligand binding domain and a signaling domain;

wherein the one or more cells obtained by steps (a) and (b) are suitable for use in human therapy, and further wherein the cells obtained by steps (a) and (b) elicit no or a reduced graft-versus-host disease (GVHD) response in a histoincompatible human recipient as compared to the GVHD response elicited by a primary human T cell or primary human T cells isolated from the same human donor either of which are only modified as in (b).

2. The method of claim 1, which further comprises determining whether the resultant modified primary human T cells comprise reduced expression of the targeted TCR component by at least one of: (a) detecting the level of expression of said targeted TCR component in the resultant modified primary human T cell or cells; (b) detecting whether the resultant modified primary human T cell or cells elicit a GVHD response in a human subject;

and (c) comparing the level of gamma interferon produced by cells modified as in steps (a) and (b) of claim 1 in response to allogeneic cells compared to the level of gamma interferon produced by a primary human T cell or cells isolated from the same donor but only modified as in step (b) of claim 1 in response to allogeneic cells.

3. The method of claim 1, which further comprises purifying or enriching the primary human T cells obtained by steps (a) and (b) by removing human primary T cells that retain moderate to high expression of the targeted TCR component.

4. The method of claim 1, wherein step (a) comprises introducing multiple shRNAs that target the same TCR component or different TCR components.

5. The method of claim 1, wherein said shRNAs target one or more TCR components selected from TCR-α, TCR-β, CD3-γ, CD3-δ, and CD3-ε.

6. The method of claim 1, wherein the at least one functional exogenous non-TCR comprises a ligand binding domain obtained from an anti-tumor chimeric antigen receptor or anti-tumor antibody.

7. The method of claim 1, wherein the ligand binding domain of the at least one functional exogenous non-TCR comprises a pathogen-associated receptor and the resultant modified primary human T cell or cells can be used to treat infectious disease.

8. The method of claim 7, wherein said infectious disease to be treated is caused by a CMV, HIV-1, HIV-2, HBV, HCV, or hantavirus infection.

9. The method of claim 1, wherein the chimeric receptor comprises a NKG2D, NKG2A, NKG2C, NKG2F, LLT1, AICL, CD26, or NKRP1 polypeptide.

10. The method of claim 1, wherein the chimeric receptor comprises a receptor that binds to MIC-A, MIC-B, estrogen, progesterone, RON, or one or more members of the ULBP/RAET1 family.

11. The method of claim 1, wherein the chimeric receptor comprises a NKG2D ligand binding domain and a CD3-ζ signaling domain.

12. The method of claim 1, wherein the resultant modified human primary T cells are suitable for use in treating cancer.

13. The method of claim 1, which further comprises formulating the resultant modified primary human T cells with at least one pharmaceutically acceptable carrier in order to obtain a composition suitable for human therapy.

14. The method of claim 1, which further comprises administering to a human subject having cancer a therapeutically effective amount of the resultant modified primary human T cells.

15. A method of producing one or more modified primary human T cells, which modified primary human T cells are derived from primary human T cells isolated from a human donor that (i) are modified to functionally impair or to reduce expression of the endogenous T cell receptor (TCR), and (ii) are further modified to express at least one functional exogenous non-TCR that comprises a chimeric receptor comprising a ligand binding domain and a signaling domain, said method including the following:

(a) introducing into one or more primary human T cells isolated from a human donor at least one nucleic acid that encodes a dominant-negative inhibitor protein that is capable of interrupting expression or function of the endogenous TCR, wherein said nucleic acid comprises a polynucleotide that encodes a variant of a polypeptide component of a functional TCR complex endogenously expressed by an unmodified primary T human cell isolated from said human donor, wherein said variant polypeptide TCR component is modified, compared to the unmodified polypeptide TCR component, by one or more of the following: (1) the variant polypeptide TCR component lacks key signaling motifs required for function of the unmodified polypeptide TCR component; (2) the variant polypeptide TCR component is modified such that it does not associate properly with other endogenous TCR components; or (3) the variant polypeptide TCR component is modified such that it is still capable of associating properly with other endogenous TCR components, but the resultant TCR complex containing the variant polypeptide TCR component is incapable of binding to ligands; and (b) further introducing into said one or more primary human T cells isolated from a human donor at least one nucleic acid that results in the expression of a functional exogenous non-TCR receptor that comprises a chimeric receptor comprising a ligand binding domain and a signaling domain;

wherein the one or more cells obtained by steps (a) and (b) are suitable for use in human therapy, and further wherein the cells obtained by steps (a) and (b) elicit no or a reduced graft-versus-host disease (GVHD) response in a histoincompatible human lrecipient as compared to the GVHD response elicited by a primary human T cell or primary human T cells isolated from the same human donor either of which are only modified as in (b).

16. The method of claim 15, wherein said variant polypeptide TCR component is derived from a TCR component selected from TCR-α, TCR-β, TCR-γ, TCR-δ, CD3-γ, CD3-δ, CD3-ε, and CD3-ζ.

17. The method of claim 15, wherein said modified primary human T cells express more than one variant of a TCR component selected from TCR-α, TCR-β, TCR-γ, TCR-δ, CD3-γ, CD3-δ, CD3-ε, and CD3-ζ.

18. The method of claim 15, wherein said variant polypeptide TCR component comprises deletions in the transmembrane portion of the TCR component that are required for TCR assembly.

19. The method of claim 15, wherein said variant polypeptide TCR component comprises one of the following: (i) a modified TCR-α lacking an arginine residue at position 5 in the TCR-α transmembrane region; (ii) a modified TCR-α lacking a lysine residue at position 10 in the TCR-α transmembrane region; (iii) a modified TCR-β lacking a lysine residue at position 9 in the TCR-β transmembrane region; (iv) a modified CD3-γ lacking a glutamic acid residue in the transmembrane region of CD3-γ; (v) a modified CD3-δ or CD3-ε lacking an aspartic acid residue in the transmembrane region of CD3-δ or CD3-ε; and (vi) a modified CD3-ζ lacking an aspartic acid residue in the transmembrane region of CD3-ζ.

20. The method of claim 15, which further comprises determining whether the resultant modified primary human T cells comprise a functionally impaired TCR or reduced expression of the endogenous TCR by at least one of: (a) detecting the level of expression of said variant polypeptide TCR component in the resultant modified primary human T cell or cells; (b) detecting whether the resultant modified cells elicit a GVHD response in a human subject; and (c) comparing the level of gamma interferon produced by said primary human T cell or cells obtained by steps (a) and (b) of claim 15 in response to allogeneic cells compared to the level of gamma interferon produced by a primary human T cell or cells isolated from the same donor but only modified as in (ii) step (b) of claim 15 in response to allogeneic cells.

21. The method of claim 15, which further comprises purifying or enriching the primary human T cells obtained by steps (a) and (b) to by removing the human primary T cells that retain moderate to high expression of the targeted TCR component.

22. The method of claim 15, wherein the at least one functional exogenous non-TCR comprises a ligand binding domain obtained from an anti-tumor chimeric antigen receptor or anti-tumor antibody.

23. The method of claim 15, wherein the ligand binding domain of the at least one functional exogenous non-TCR comprises a pathogen-associated receptor and the resultant modified primary human T cell or cells can be used to treat infectious disease.

24. The method of claim 23, wherein said infectious disease to be treated is caused by a CMV, HIV-1, HIV-2, HBV, HCV, or hantavirus infection.

25. The method of claim 15, wherein the chimeric receptor comprises a NKG2D, NKG2A, NKG2C, NKG2F, LLT1, AICL, CD26, or NKRP1 polypeptide.

26. The method of claim 15, wherein the chimeric receptor comprises a receptor that binds to MIC-A, MIC-B, estrogen, progesterone, RON, or one or more members of the ULBP/RAET1 family.

27. The method of claim 15, wherein the chimeric receptor comprises a NKG2D ligand binding domain and a CD3-ζ signaling domain.

28. The method of claim 15, wherein the resultant modified human primary T cells are suitable for use in treating cancer.

29. The method of claim 15, which further comprises formulating the resultant modified primary human T cells with at least one pharmaceutically acceptable carrier in order to obtain a composition suitable for human therapy.

30. The method of claim 15, which further comprises administering to a human subject having cancer a therapeutically effective amount of the resultant modified primary human T cells.

* * * * *